(12) United States Patent
Dennis et al.

(10) Patent No.: US 10,022,452 B2
(45) Date of Patent: Jul. 17, 2018

(54) ANTI-MESOTHELIN ANTIBODIES AND IMMUNOCONJUGATES

(71) Applicant: Genentech, Inc., South San Francisco, CA (US)

(72) Inventors: Mark Dennis, San Carlos, CA (US); Suzanna J. Scales, San Mateo, CA (US); Susan D. Spencer, Tiburon, CA (US); Yin Zhang, Fremont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/486,832

(22) Filed: Apr. 13, 2017

(65) Prior Publication Data

US 2017/0281792 A1    Oct. 5, 2017

Related U.S. Application Data

(62) Division of application No. 14/539,197, filed on Nov. 12, 2014, now Pat. No. 9,719,996, which is a division of application No. 13/330,414, filed on Dec. 19, 2011, now Pat. No. 8,911,732.

(60) Provisional application No. 61/459,962, filed on Dec. 20, 2010.

(51) Int. Cl.
| | |
|---|---|
| *A61K 51/10* | (2006.01) |
| *C07K 16/30* | (2006.01) |
| *A61K 31/7068* | (2006.01) |
| *A61K 45/06* | (2006.01) |
| *A61K 39/395* | (2006.01) |
| *A61K 38/08* | (2006.01) |
| *A61K 47/48* | (2006.01) |
| *A61K 39/00* | (2006.01) |

(52) U.S. Cl.
CPC .... *A61K 47/48438* (2013.01); *A61K 31/7068* (2013.01); *A61K 38/08* (2013.01); *A61K 39/39558* (2013.01); *A61K 45/06* (2013.01); *A61K 47/48569* (2013.01); *A61K 47/48638* (2013.01); *C07K 16/30* (2013.01); *A61K 2039/507* (2013.01); *C07K 2317/24* (2013.01); *C07K 2317/33* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,320,956 A | 6/1994 | Willingham et al. | |
| 5,525,337 A | 6/1996 | Willingham et al. | |
| 5,723,318 A | 3/1998 | Yamaguchi et al. | |
| 5,817,313 A | 10/1998 | Willingham et al. | |
| 6,083,502 A | 7/2000 | Pastan et al. | |
| 6,153,430 A | 11/2000 | Pastan et al. | |
| 6,770,445 B1 | 8/2004 | Scholler et al. | |
| 6,809,184 B1 | 10/2004 | Pastan et al. | |
| 7,081,518 B1 | 7/2006 | Pastan et al. | |
| 7,368,110 B2 | 5/2008 | Pastan et al. | |
| 7,375,183 B1 | 5/2008 | Pastan et al. | |
| 7,521,054 B2 | 4/2009 | Pastan et al. | |
| 7,592,426 B2 | 9/2009 | Ebel et al. | |
| 7,659,241 B2 | 2/2010 | Senter et al. | |
| 7,709,252 B2 | 5/2010 | Pastan et al. | |
| 7,745,159 B2 | 6/2010 | Scholler et al. | |
| 7,745,394 B2 | 6/2010 | Doronina et al. | |
| 7,829,531 B2 | 11/2010 | Senter et al. | |
| 7,851,437 B2 | 12/2010 | Senter et al. | |
| 7,964,566 B2 | 6/2011 | Doronina et al. | |
| 8,206,710 B2 | 6/2012 | Ebel et al. | |
| 8,268,970 B2 | 9/2012 | Terrett et al. | |
| 8,383,779 B2 | 2/2013 | Terrett et al. | |
| 8,399,623 B2 | 3/2013 | Terrett et al. | |
| 8,425,904 B2 | 4/2013 | Terrett et al. | |
| 8,911,732 B2 | 12/2014 | Dennis et al. | |
| 2002/0132237 A1 | 9/2002 | Algate et al. | |
| 2003/0087250 A1 | 5/2003 | Monahan et al. | |
| 2004/0142396 A1 | 7/2004 | Scholler et al. | |
| 2004/0180387 A1 | 9/2004 | O'Shannessy | |
| 2005/0054056 A1 | 3/2005 | Ebel et al. | |
| 2005/0106644 A1 | 5/2005 | Cairns et al. | |
| 2005/0107595 A1 | 5/2005 | Cairns et al. | |
| 2005/0123536 A1 | 6/2005 | Law et al. | |
| 2005/0214831 A1 | 9/2005 | Monahan et al. | |
| 2005/0232929 A1 | 10/2005 | Kadkhodayan et al. | |
| 2005/0238649 A1 | 10/2005 | Doronina et al. | |
| 2005/0256030 A1 | 11/2005 | Feng | |
| 2005/0276812 A1 | 12/2005 | Ebens et al. | |
| 2006/0014211 A1 | 1/2006 | O'Shannessy et al. | |
| 2006/0014221 A1 | 1/2006 | O'Shannessy et al. | |

(Continued)

FOREIGN PATENT DOCUMENTS

| | | |
|---|---|---|
| EP | 2096168 A1 | 9/2009 |
| TW | I477513 B | 3/2015 |

(Continued)

OTHER PUBLICATIONS

Bergan et al., "Development and in vitro validation of anti-mesothelin biobodies that prevent CA125/Mesothelin-dependent cell attachment", Cancer Letters, 255:263-274 (2007).

Beyer et al., "MESOMARK™: A potential Test for Malignant Pleural Mesothelioma", Clinical Chemistry, 53(4):666-672 (2007).

Bowie et al., "Deciphering the message in protein sequences: tolerance to amino acid substitutions", Science, 247:1306-1310 (1990).

(Continued)

*Primary Examiner* — Brian J Gangle
*Assistant Examiner* — Andrea K McCollum
(74) *Attorney, Agent, or Firm* — Jessica L. Richardson

(57) ABSTRACT

The invention provides anti-mesothelin antibodies and immunoconjugates and methods of using the same.

26 Claims, 32 Drawing Sheets

(56) References Cited

U.S. PATENT DOCUMENTS

| | | |
|---|---|---|
| 2006/0074008 A1 | 4/2006 | Senter et al. |
| 2006/0182751 A1 | 8/2006 | Gazzard et al. |
| 2007/0092940 A1 | 4/2007 | Eigenbrot et al. |
| 2007/0134243 A1 | 6/2007 | Gazzard et al. |
| 2008/0014208 A1 | 1/2008 | Reiter et al. |
| 2008/0125363 A1 | 5/2008 | Filpula et al. |
| 2008/0171040 A1 | 7/2008 | Ebens, et al. |
| 2008/0213289 A1 | 9/2008 | Francisco et al. |
| 2008/0226657 A1 | 9/2008 | Doronina et al. |
| 2008/0248051 A1 | 10/2008 | Doronina et al. |
| 2008/0248053 A1 | 10/2008 | Doronina et al. |
| 2009/0041791 A1 | 2/2009 | Feng |
| 2009/0047211 A1 | 2/2009 | Pastan et al. |
| 2009/0047296 A1 | 2/2009 | Doronina et al. |
| 2009/0175865 A1 | 7/2009 | Eigenbrot et al. |
| 2009/0202536 A1 | 8/2009 | Ebens et al. |
| 2009/0226465 A1 | 9/2009 | Jackson |
| 2009/0280556 A1 | 11/2009 | Pastan et al. |
| 2009/0324621 A1 | 12/2009 | Senter et al. |
| 2010/0003766 A1 | 1/2010 | Eigenbrot et al. |
| 2010/0034837 A1 | 2/2010 | Beria et al. |
| 2010/0062008 A1 | 3/2010 | Senter et al. |
| 2010/0111852 A1 | 5/2010 | Yoshida |
| 2010/0111856 A1 | 5/2010 | Gill et al. |
| 2010/0221176 A1 | 9/2010 | Gill et al. |
| 2011/0027268 A1 | 3/2011 | Kahnert et al. |
| 2011/0064753 A1 | 3/2011 | Senter et al. |
| 2011/0076287 A1 | 3/2011 | Cohen et al. |
| 2011/0104675 A1 | 5/2011 | Scholler et al. |
| 2011/0137017 A1 | 6/2011 | Eigenbrot et al. |
| 2011/0256157 A1 | 10/2011 | Howard et al. |
| 2011/0301334 A1 | 12/2011 | Bhakta et al. |
| 2012/0003247 A1 | 1/2012 | Doronina et al. |
| 2012/0003248 A1 | 1/2012 | Doronina et al. |
| 2012/0027783 A1 | 2/2012 | Doronina et al. |
| 2012/0027784 A1 | 2/2012 | Doronina et al. |
| 2012/0034246 A1 | 2/2012 | Doronina et al. |
| 2012/0121615 A1 | 5/2012 | Flygare et al. |
| 2012/0130059 A1 | 5/2012 | Beria et al. |
| 2012/0141508 A1 | 6/2012 | Doronina et al. |
| 2012/0141509 A1 | 6/2012 | Doronina et al. |
| 2012/0141510 A1 | 6/2012 | Doronina et al. |
| 2012/0148608 A1 | 6/2012 | Doronina et al. |
| 2012/0148610 A1 | 6/2012 | Doronina et al. |
| 2012/0189644 A1 | 7/2012 | Kahnert et al. |
| 2012/0315645 A1 | 12/2012 | Kaur et al. |
| 2013/0028917 A1 | 1/2013 | Howard et al. |
| 2013/0216475 A1 | 8/2013 | Gill et al. |
| 2013/0266595 A1 | 10/2013 | Flygare et al. |

FOREIGN PATENT DOCUMENTS

| | | |
|---|---|---|
| WO | 94/10312 | 5/1994 |
| WO | 1999/028471 A2 | 6/1999 |
| WO | 1999/028471 A3 | 6/1999 |
| WO | 01/92581 | 12/2001 |
| WO | 02/101075 A | 12/2002 |
| WO | 02/102235 | 12/2002 |
| WO | 2003/014322 | 2/2003 |
| WO | 03/043583 A2 | 5/2003 |
| WO | 03/043583 A3 | 5/2003 |
| WO | 03/101283 | 12/2003 |
| WO | 2004/006837 | 1/2004 |
| WO | 2004/010957 A2 | 2/2004 |
| WO | 2004/010957 A3 | 2/2004 |
| WO | 2005/081711 A2 | 9/2005 |
| WO | 2005/082023 | 9/2005 |
| WO | 2005/101017 | 10/2005 |
| WO | 2005/117986 A2 | 12/2005 |
| WO | 2006/002114 | 1/2006 |
| WO | 2006/034488 A2 | 3/2006 |
| WO | 2006/060533 | 6/2006 |
| WO | 2006/099141 | 9/2006 |
| WO | 2007/064345 | 6/2007 |
| WO | 2007/100385 | 9/2007 |
| WO | 2007/112047 | 10/2007 |
| WO | 2008/068906 | 6/2008 |
| WO | 2008/072723 A1 | 6/2008 |
| WO | 2008/085266 A2 | 7/2008 |
| WO | 2008/141044 A2 | 11/2008 |
| WO | 2009/045957 | 4/2009 |
| WO | 2009/068204 | 6/2009 |
| WO | 2009/099741 A1 | 8/2009 |
| WO | 2009/120769 | 10/2009 |
| WO | 2010/009124 | 1/2010 |
| WO | 2010/099273 | 9/2010 |
| WO | 2010/111282 | 9/2010 |
| WO | 2010/124797 A1 | 11/2010 |
| WO | 2011/056983 A1 | 5/2011 |
| WO | 2011/130598 | 10/2011 |
| WO | 2011/156328 A1 | 12/2011 |
| WO | 2012/074757 | 6/2012 |
| WO | 2012/106587 | 8/2012 |
| WO | 2012/55019 | 11/2012 |
| WO | 2013/055987 A1 | 4/2013 |

OTHER PUBLICATIONS

Brinkmann et al., "Cloning and Expression of the Recombinant FAb Fragment of Monoclonal Antibody K1 that Reacts with Mesothelin Present on Mesotheliomas and Ovarian Cancers", Int.J. Cancer, 71:638-644 (1997).

Brown et al., "Tolerance of single, but not multiple, amino acid replacements in antibody VH CDR 2: a means of minimizing B cell wastage from somatic hypermutation?", The Journal of Immunology, 156(9):3285-3291 (1996).

Burgess et al., "Possible dissociation of the heparin-binding and mitogenic activities of heparin-binding (Acidic Fibroblast) growth factor-1 from its receptor-binding activities by site-directed mutagenesis of a single lysine residue", Journal of Cell Biology, 111:2129-2138 (2010).

Chang et al., "Characterization of the Antigen (CAK1) Recognized by Monoclonal Antibody K1 Present on Ovarian Cancers and Normal Mesothelium", Cancer Research, 52: 181-186 (1992).

Chang et al., "Isolation and Characterization of a Monoclonal Antibody, K1, Reactive with Ovarian Cancers and Normal Mesothelium", Int. J. Cancer, 50:373-381 (1992).

Chang et al., "Molecular cloning of mesothelin, a differentiation antigen present on mesothelium, mesotheliomas, and ovarian cancers", Proc. Natl. Acad. Sci. USA, 93:136-140 (1996).

Chowdhury et al. et al., "Improving Antibody Affinity by Mimicking Somatic Hypermutation in Vitro", Nat Biotechnol, 17:568-572 (Jun. 1999).

Chowdhury et al., "Isolation of a high-affinity stable single-chain Fv specific for mesothelin from DNA-immunized mice by phage display and construction of a recombinant immunotoxin with anti-tumor activity", Proc. Natl. Acad. Sci. USA, 95:669-674 (1998).

Chowdhury et al., "Isolation of Anti-Mesothelin Antibodies From a Phage Display Library", Molecular Immunology, 34(1):9-20 (1997).

Co et al., "Properties and pharmacokinetics of two humanized antibodies specific for L-selectin", Immunotechnology, 4:253-266 (1999).

International Search Report for counterpart PCT Application No. PCT/US2011/065895.

Ducry et al., "Antibody—Drug Conjugates: Linking Cytotoxic Payloads to Monoclonal Antibodies", Bioconjugate Chem., 21:5-13 (2010).

Einama et al., "Co-Expression of Mesothelin and CA125 Correlates with Unfavorable Patient Outcome in Pancreatic Ductal Adenocarcinoma", Pancreas, 40(8):1276-1282 (2011).

Feng et al., "A novel human monoclonal antibody that binds with high affinity to mesothelin-expressing cells and kills them by antibody-dependent cell-mediated cytotoxicity", Molecular Cancer Therapeutics, 8:1113-1118 (2009).

GenBank: AAB24132.1 (May 8, 1993).

GenBank: AAF21960.1 (Jan. 1, 2000).

Giusti et al., "Somatic diversification of S107 from an antiphosphocholine to an anti-DNA autoantibody is due to a single

(56) References Cited

OTHER PUBLICATIONS base change in its heavy chain variable region", Proc. Nati. Acad. Sci. USA, 84:2926-2930 (1987).
Gubbels et al., "Mesothelin-MUC16 binding is a high affinity, N-glycan dependent interaction that facilitates peritoneal metastasis of ovarian tumors", Molecular Cancer, 5:50 (2006).
Hassan et al., "Anti-Mesothelin Immunotoxin SS1P in Combination with Gemcitabine Results in Increased Activity against Mesothelin-Expressing Tumor Xenografts", Clinical Cancer Research, 13:7166-7171 (2007).
Hassan et al., "Antitumor Activity of SS(dsFv) PE38 and SS1(dsFv)PE38, Recombinant Antimesothelin Immunotoxins against Human Gynecologic Cancers Grown in Organotypic Culture in Vitro", Clinical Cancer Research, 8:3520-3526 (2002).
Hassan et al., "Detection and Quantitation of Serum Mesothelin, a Tumor Marker for Patients with Mesothelioma and Ovarian Cancer", Clinical Cancer Research, 12:447-453 (2006).
Hassan et al., "Mesothelin targeted cancer immunotherapy", Eur J Cancer, 44(1):46-53 (2008).
Hassan et al., "Mesothelin: A New Target for Immunotherapy", Clinical Cancer Research, 10:3937-3942 (2004).
Hassan et al., "Phase I Clinical Trial of the Chimeric Anti-Mesothelin Monoclonal Antibody MORAb-009 in Patients with Mesothelin-Expressing Cancers", Clinical Cancer Research, 16:6132-6138 (2010).
Hassan et al., "Phase I Study of SS1P, A Recombinant Anti-Mesothelin Immunotoxin Given as a Bolus I.V. Infusion to Patients with Mesothelin-Expressing Mesothelioma, Ovarian, and Pancreatic Cancer", Clinical Cancer Research, 13:5144-5149 (2007).
Hassan et al., "Preclinical evaluation of MORAb-009, a chimeric antibody targeting tumor-associated mesothelin", Cancer Immunity, 7:20 (2007).
Hellstrom et al., "Mesothelin Variant 1 Is Released from Tumor Cells as a Diagnostic Marker", Cancer Epidemiology Biomarkers Prevention, 15:1014-1020 (2006).
Ho et al., "Humoral Immune Response to Mesothelin in Mesothelioma and Ovarian Cancer Patients", Clinical Cancer Research, 11:3814-3820 (2005).
Ho et al., "Mesothelin Expession in Human Lung Cancer", Clinical Cancer Research, 13:1571-1575 (2007).
International Preliminary Report on Patentability issued in International Application No. PCT/US2011/065895, dated Jun. 25, 2013, in 12 pages.
International Search Report issued in International Application No. PCT/UA2011/065895, dated Jul. 4, 2012, in 9 pages.
Ishikawa et al., "Establishment of novel mAb to human ERC/mesothelin useful for study and diagnosis of ERC/mesothelin-expressing cancers", Pathology International, 59:161-166 (2009).
Jefferis et al., "Evaluation of monoclonal antibodies having specific city for human IgG subclasses: results of the 2nd IUIS/WHO collaborative study", Immunology Letters, Elsevier 31(2):143-168 (Feb. 1, 1992).
Kaneko et al., "A Binding Domain on Mesothelin for CA125/MUC16", J. Biol. Chem, 284(6):3739-3749 (2009).
Kojima et al., "Molecular Cloning and Expression of Megakaryocyte Potentiating Factor cDNA", Journal of Biological Chemistry, 270:21984-21990 (1995).
Lazar et al., "Transforming growth factor alpha: mutation of aspartic acid 47 and leucine 48 results in different biological activities", Mol Cell Biol., 8:1247-1252 (1988).
Li et al., "Cytotoxic Activity of the Recombinant Anti-mesothelin Immunotoxin, SS1 (dsFv) PE38, Towards Tumor Cell Lines Established from Ascites of Patients with Peritoneal Mesotheliomas", Anticancer Research, 24:1327-1336 (2004).
Li et al., "Mesothelin is a malignant factor and therapeutic vaccine target for pancreatic cancer", Molecular Cancer Therapeutics, 7:286-296 (2008).
McCarty et al., "Use of Monoclonal Anti-Estrogen Receptor Antibody in the Immunohistochemical Evaluation of Human Tumors", Cancer Research, 46(8):4244s-4248s (1986).

Muminova et al., "Characterization of human mesothelin transcripts in ovarian and pancreatic cancer", BMC Cancer, 4:19 (2004).
Office Action issued in Japanese Patent Application No. 2013-544871, dated Oct. 4, 2016 with English translation (total in 5 pages).
Office Action issued in Malaysian Patent Application No. PI 2013002192, dated Aug. 15, 2016 (in 4 pages).
Onda et al., "Megakaryocyte Potentiation Factor Cleaved from Mesothelin Precursor Is a Useful Tumor Marker in the Serum of Patients with Mesothelioma", Clinical Cancer Research, 12(14):4225-4231 (2006).
Onda et al., "New Monoclonal Antibodies to Mesothelin Useful for Immunohistochemistry, Fluorescence-Activated Cell Sorting, Western Blotting, and ELISA", Clinical Cancer Research, 11(16):5840-5846 (2005).
Ordonez et al., "Application of Mesothelin Immunostaining in Tumor Diagnosis", Am J Surg Pathol, 27(11):1418-1428 (2003).
Pass et al., "Soluble Mesothelin-Related Peptide Level Elevation in Mesothelioma Serum and Pleural Effusions", Ann. Thorac. Surg., 85:265-272 (2008).
Reiter et al., "Stabilization of the Fv Fragments in Recombinant Immunotoxins by Disulfide Bonds Engineered into Conserved Framework Regions", Biochemistry, 33:5451-5459 (1994).
Rodrigues et al., "Engineering a Humanized Bispecific F(ab')2 Fragment for Improved Binding TOT Cells", Int. J. Cancer, 7:45-50 (1992).
Rudikoff et al., "Single amino acid substitution altering antigen-binding specificity", P Natl Acad Sci USA, 79:1979-1983 (Mar. 1982).
Rump et al. et al., "Binding of Ovarian Cancer Antigen CA125/MUC16 to Mesothelin Mediates Cell Adhesion", J Biol Chem, 279(10):9190-9198 (2004).
Sandeck et al., "Re-evaluation of histological diagnoses of malignant mesothelioma by immunohistochemistry", Diagnostic Pathology, 5:47 (2010).
Scales et al., "An Antimesothelin-Monomethyl Auristatin E Conjugate with Potent Antitumor Activity in Ovarian, Pancreatic, Mesothelioma Models", Mol Cancer Ther, 13(11):2630-2640 (Nov. 2014).
Schildbach et al., "Contribution of a single heavy chain residue to specificity of an anti-digoxin monoclonal antibody", Protein Science, 3:737-749 (1994).
Scholler et al., "Development of a CA125-mesothelin cell adhesion assay as a screening tool for biologics discovery", Cancer Letters, 247:130-136 (2007).
Scholler et al., "Soluble member(s) of the mesothelin/megakaryocyte potentiating factor family are detectable in sera from patients with ovarian carcinoma", Proc. Natl. Acad. Sci. USA, 96:11531-11536 (1999).
Search Report issued in ROC (Taiwan) Patent Application No. 103146178, dated May 3, 2016, with English translation, total in 3 pages.
Steinbach et al., "Mesothelin, a possible target for immunotherapy, is expressed in primary AML cells", European Journal of Haematology, 79:281-286 (2007).
Toki, "Cures and regressions of established tumor xenografts with monoclonal antibody auristatin E", Slides 223rd ACS Meeting, Orlando Fl., Apr. 7-11, 2002, Abstract 147.
Vajdos et al., "Comprehensive Functional Maps of the Antigenbinding Site of an Anti-ErbB2 Antibody Obtained with Shotgun Scanning Mutagenesis", J. Mol. Biol., 320:415-428 (2002).
Written Opinion of International Searching Authority issued in International Application No. PCT/US2011/065895, dated Jul. 4, 2012, in 11 pages.
Xiang et al., "Study of B72.3 combining sites by molecular modeling and site-directed mutagenesis", Protein Engineering, 13(5):339-344 (2000).
Yamaguchi et al., "A Novel Cytokine Exhibiting Megakaryocte Potentiating Activity From a Human Pancreatic Tumor Cell Line HPC-Y5"Journal of Biological Chemistry, 269(2):805-808 (1994).
Yen et al., "Diffuse Mesothelin Expression Correlates with Prolonged Patient Survival in Ovarian Serous Carcinoma", Clin Cancer Res, 12:827-831 (2006).

(56) References Cited

OTHER PUBLICATIONS

Yokokawa et al., "Identification of Novel Human CTL Epitopes and Their Agonist Epitopes of Mesothelin", Clinical Cancer Research, 11:6342-6351 (2005).

Anti-mesothelin Monoclonal Antibodies

| mAb | Isotype | Epitope Group | Epitope Region | Blocks muc16 Binding? | Kd (nM) Biacore |
|---|---|---|---|---|---|
| 7D9 | G1 | A | 152-175 | Enhances | 0.23 |
| 19C3 | G2b | C | 1-70 | YES | 0.06 |
| 2E5 | G2 | C | 1-70 | YES | 0.49 |
| 8B11 | G1 | B1 | 71-131 | No | 138 |
| 17A5 | G1 | B1 | 71-131 | No | n.d. |
| 11H8 | G2b | B1 | 71-131 | No | n.d. |
| 16D5 | G2a | B2 | 71-131 | Enhances | 2.21 |
| 18D12 | G2b | B3 | 131-178 | No | n.d. |
| 3H2 | G1 | B | 71-131 | Enhances | n.d. |
| 22A10 | G2a | D | 209-212 | Enhances | 4.25 |
| 15F7 | G2a | E | 1-131 | No | n.d. |
| 12F6 | G2a | E | n.d. | n.d. | 780 |

Chimeric and Humanized Variants of 7D9

| | LC | HC | KD (nM) Over Human MSLN |
|---|---|---|---|
| Chimeric 7D9 | Chimeric | Chimeric | 1.84 |
| 7D9.v1 | $V_{kI}$ Graft | $VH_{ATA}$ Graft | 3.98 |
| 7D9.v2 | Y36F, Y87F | V48I, F67A, I69L, K75S, N76S and L80M | 1.78 |
| 7D9.v3 | Y36F, Y87F | $VH_{ATA}$ Graft | 1.9 |
| 7D9.v4 | $V_{kI}$ Graft | V48I, F67A, I69L, K75S, N76S and L80M | 3.01 |
| 7D9.v5 | Y36F | $VH_{ATA}$ Graft | 3.49 |
| 7D9.v6 | Y87F | $VH_{ATA}$ Graft | 4.08 |

Scatchard Analysis of Humanized 22A10 Variants on gD-Mesothelin BJAB Stable Cells

| Panned On | - | | Cyno | | Cyno+Hu | | Cyno | |
|---|---|---|---|---|---|---|---|---|
| h22A10 Version | Graft nM | Graft Sites | v1 nM | v1 Sites | v17 nM | v17 Sites | v83 nM | v83 Sites |
| Cyno BJAB | 1.0 | 25000 | 1.0 | 21000 | 1.0 | 25000 | 1.3 | 45000 |
| Human BJAB | 1.6 | 18000 | 1.9 | 16000 | 1.7 | 17000 | 1.8 | 31000 |
| Rat BJAB | 1.9 | 22400 | 2.8 | 15000 | 3.9 | 24000 | 2.7 | 31000 |

| Humanized Antibody 7D9 Region | Sequence | SEQ ID NO: |
|---|---|---|
| h7D9.v1, h7D9.v3 HVR-L1 | KSSQSVLYSSNQKNYLA | 17 |
| h7D9.v1, h7D9.v3 HVR-L2 | WASTRES | 18 |
| h7D9.v1, h7D9.v3 HVR-L3 | HQYLSSYT | 19 |
| h7D9.v1, h7D9.v3 HVR-H1 | GYTFTTYWMH | 20 |
| h7D9.v1, h7D9.v3 HVR-H2 | GYIRPSTGYTEYNQKFKD | 21 |
| h7D9.v1, h7D9.v3 HVR-H3 | ARSRWLLDY | 22 |
| h7D9.v1, h7D9.v3 VL-FR1 | DIQMTQSPSSLSASVGDRVTITC | 23 |
| h7D9.v1 VL-FR2 | WYQQKPGKAPKLLIY | 24 |
| h7D9.v3 VL-FR2 | WFQQKPGKAPKLLIY | 25 |
| h7D9.v1 VL-FR3 | GVPSRFSGSGSGTDFTLTISSLQPEDFATYYC | 26 |
| h7D9.v3 VL-FR3 | GVPSRFSGSGSGTDFTLTISSLQPEDFATYFC | 27 |
| h7D9.v1, h7D9.v3 VL-FR4 | FGQGTKVEIKR | 28 |
| h7D9.v1, h7D9.v3 VH-FR1 | EVQLVESGGGLVQPGGSLRLSCAAS | 29 |
| h7D9.v1, h7D9.v3 VH-FR2 | WVRQAPGKGLEWV | 30 |
| h7D9.v1, h7D9.v3 VH-FR3 | RFTISADTSKNTAYLQMNSLRAEDTAVYYC | 31 |
| h7D9.v1, h7D9.v3 VH-FR4 | WGQGTLVTVS | 32 |

*FIG. 10A*

| Humanized Antibody 22A10 Region | Sequence | SEQ ID NO: |
|---|---|---|
| h22A10graft, h22A10.v83 HVR-L1 | RASQDISNYLN | 33 |
| h22A10graft, h22A10.v83 HVR-L2 | YTSRLHS | 34 |
| h22A10graft, h22A10.v83 HVR-L3 | QQGNTLPYT | 35 |
| h22A10graft, h22A10.v83 HVR-H1 | GFTFSDYFMS | 36 |
| h22A10graft, h22A10.v83 HVR-H2 | ATISNGGTYTYYPDSVKG | 37 |
| h22A10graft HVR-H3 | ARFDGYYFDY | 38 |
| h22A10.v83 HVR-H3 | ARFDGYIFDY | 39 |
| h22A10graft, h22A10.v83 VL-FR1 | DIQMTQSPSSLSASVGDRVTITC | 23 |
| h22A10graft, h22A10.v83 VL-FR2 | WYQQKPGKAPKLLIY | 24 |
| h22A10graft, h22A10.v83 VL-FR3 | GVPSRFSGSGSGTDFTLTISSLQPEDFATYYC | 26 |
| h22A10graft, h22A10.v83 VL-FR4 | FGQGTKVEIKR | 28 |
| h22A10graft, h22A10.v83 VH-FR1 | EVQLVESGGGLVQPGGSLRLSCAAS | 29 |
| h22A10graft, h22A10.v83 VH-FR2 | WVRQAPGKGLEWV | 30 |
| h22A10graft, h22A10.v83 VH-FR3 | RFTISRDNSKNTLYLQMNSLRAEDTAVYYC | 40 |
| h22A10graft, h22A10.v83 VH-FR4 | WGQGTLVTVSS | 41 |

Anti-mesothelin Antibody Affinities
Scatchard Analysis on Mesothelin Stably Transfected and Endogenous Cell Lines:

|  | h7D9.v3 Kd (nM) | Copy # | h22A10.v83 Kd (nM) | Copy # |
|---|---|---|---|---|
| Human BJAB | 0.25 | 20000 | 1.8 | 45000 |
| Cyno BJAB | n.d. |  | 1.3 | 31000 |
| Rat BJAB | n.d. |  | 2.7 | 31000 |
| Human 293 | 0.2 | n.d. | 2.7 | 80500 |
| Cyno 293 | n.b. |  | 4.3 | 356000 |
| Rat 293 | n.d. |  | 7.3 | 81000 |
| Human HT1080 | 0.97 | 130000 | 6.2 | 38000 |
| Cyno HT1080 | n.d. |  | 6.4 | 113000 |
| Rat 4/4-RM4 | n.d. |  | 6.2 | 171000 |
| OvCar3 | 0.53 | 14178 | 9.2 | 5516 |
| OvCar3x2.1 | 0.56 | 39963 | 9 | 15294 |
| HPAC | 1 | 2600 | 9.4 | 7300 |
| Capan2 | 0.63 | 10000 | 4.2 | 11250 |
| AsPC1 | 0.58 | 2300 | 9.3 | 7100 |
| HPAF-II | 0.41 | 4200 | 10.45 | 6400 |

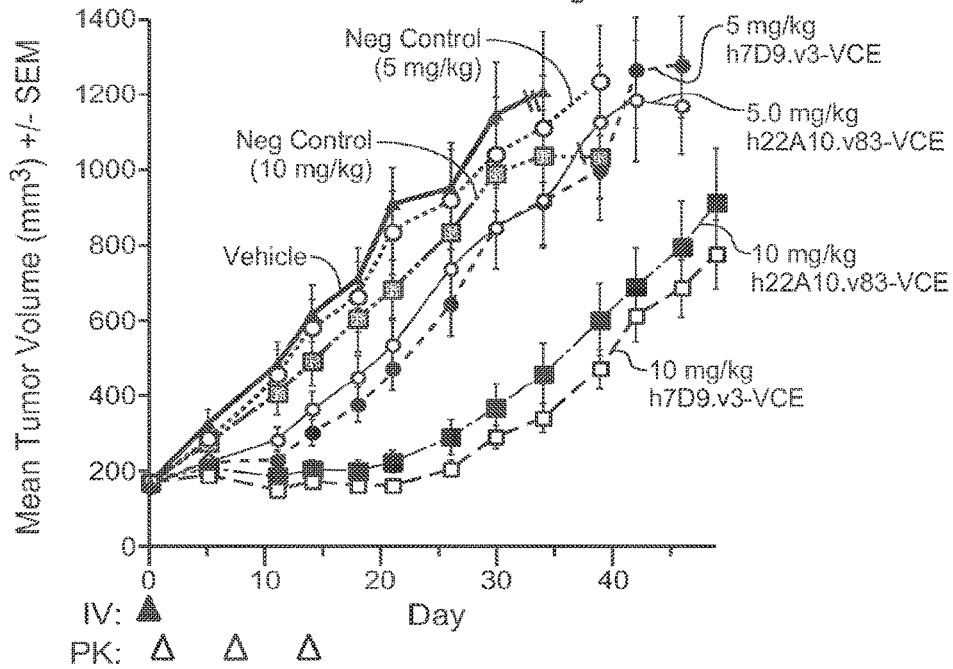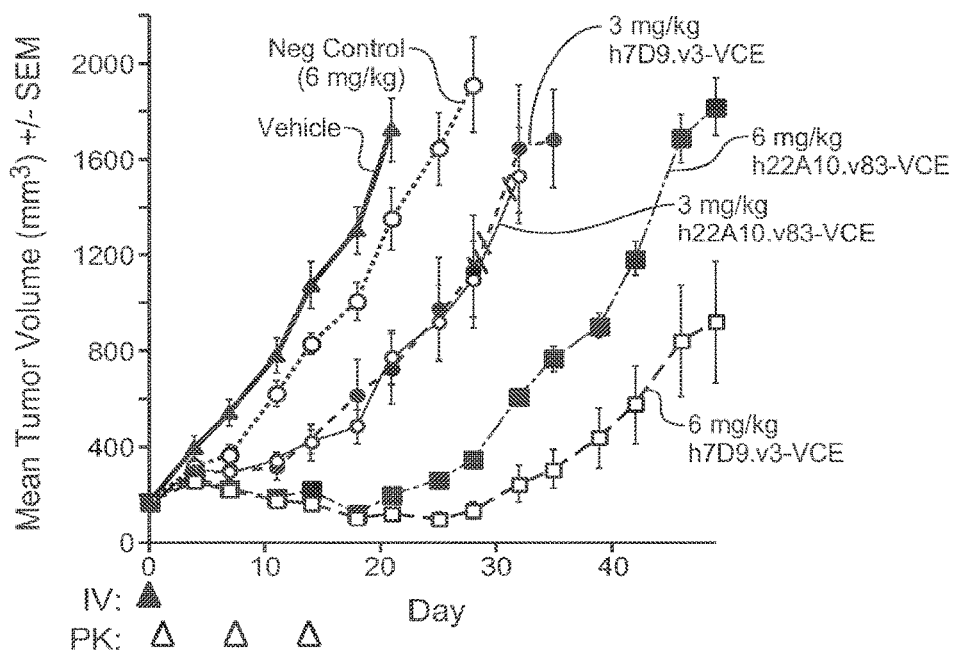
FIG. 31

ANTI-MESOTHELIN ANTIBODIES AND IMMUNOCONJUGATES

RELATED APPLICATIONS

This application is a division of U.S. patent application Ser. No. 14/539,197, filed Nov. 12, 2014, which is a division of U.S. patent application Ser. No. 13/330,414, filed Dec. 19, 2011, which claims the benefit under 35 USC 119(e) of U.S. Provisional Application No. 61/459,962 filed 20 Dec. 2010, the contents of which are incorporated herein by reference in their entireties.

SEQUENCE LISTING

The present application contains a Sequence Listing which has been submitted in ASCII format via EFS-Web and is hereby incorporated by reference in its entirety. Said ASCII copy, created on Feb. 14, 2017, is named Seq-Listing_P04532-US-3.txt and is 53,210-bytes in size.

FIELD OF THE INVENTION

The present invention relates to anti-mesothelin antibodies and immunoconjugates and methods of using the same.

BACKGROUND

Mesothelin is a cell surface glycoprotein with expression normally restricted to mesothelia (peritoneum, pericardium, and pleura). However, mesothelin is significantly overexpressed in a variety of tumor types. Mesothelin interacts with Mucin 16 (MUC16 (also called CA125)), a mucin-like glycoprotein previously identified as an ovarian tumor antigen. MUC16 has an extracellular domain comprising at least 14,000 residues and characterized by tandem repeats of 156 amino acids each, referred to as mucin repeats. (See, e.g., O'Brien et al., *Tumour Biol.* 22:348-366 (2001); Yin et al., *J. Biol. Chem.* 276:27371-27375 (2001).) The interaction between mesothelin and MUC16 is thought to play a role in heterotypic cell adhesion and metastasis. (See, e.g., Rump et al., *J. Biol. Chem.* 279:9190-9198 (2004).)

Mesothelin is synthesized as a 71 kDa precursor protein, the mature portion of which is expressed on the cell surface. That precursor protein is proteolytically cleaved by furin into a 31 kDa shed component (referred to as megakaryocyte potentiating factor, or MPF) and a 40 kDa mesothelin component. The latter component may remain associated with the cell surface via a glycosylphosphatidylinisotol (GPI) linkage but may also be shed through a proteolytic mechanism.

There is a need in the art for agents that target mesothelin for the diagnosis and treatment of mesothelin-associated conditions, such as cancer. The invention fulfills that need and provides other benefits.

SUMMARY

The invention provides anti-mesothelin antibodies and immunoconjugates and methods of using the same.

In one aspect, an isolated antibody that binds to mesothelin is provided, wherein the antibody is selected from: (i) an antibody that binds an epitope of SEQ ID NO:43 comprising E153 and D174 and that optionally has one or more of the following characteristics: (a) does not exhibit reduced binding to glycosylated forms of mesothelin; (b) does not block binding of mesothelin to MUC16; and (c) binds mesothelin with an affinity of ≤5 nM; (ii) an antibody that binds an epitope of SEQ ID NO:43 comprising E211 and that optionally has one or more of the following characteristics: (a) does not block binding of mesothelin to MUC16; and (b) binds mesothelin with an affinity of ≤5 nM; and (iii) an antibody that binds to an epitope within amino acids 1-131 of SEQ ID NO:43 and binds mesothelin with an affinity of ≤5 nM. In certain embodiments, the antibody is a monoclonal antibody. In certain embodiments, the antibody is a human, humanized, or chimeric antibody. In certain embodiments, the antibody is an antibody fragment that binds mesothelin. In certain embodiments, the mesothelin is human mesothelin of SEQ ID NO:43.

In certain embodiments, the antibody comprises: (a) (i) HVR-H3 comprising the amino acid sequence of SEQ ID NO:22, (ii) HVR-L3 comprising the amino acid sequence of SEQ ID NO: 19, and (iii) HVR-H2 comprising the amino acid sequence of SEQ ID NO:21; (b) (i) HVR-H3 comprising the amino acid sequence of SEQ ID NO:39, (ii) HVR-L3 comprising the amino acid sequence of SEQ ID NO:35, and (iii) HVR-H2 comprising the amino acid sequence of SEQ ID NO:37; or (c) HVR-H3, HVR-L3, and HVR-H2 of the antibody produced by hybridoma 19C3 having ATCC Accession No. PTA-11464. In certain embodiments, the antibody comprises (a) (i) HVR-H1 comprising the amino acid sequence of SEQ ID NO:20, (ii) HVR-H2 comprising the amino acid sequence of SEQ ID NO:21, and (iii) HVR-H3 comprising the amino acid sequence of SEQ ID NO:22; (b) (i) HVR-H1 comprising the amino acid sequence of SEQ ID NO:36, (ii) HVR-H2 comprising the amino acid sequence of SEQ ID NO:37, and (iii) HVR-H3 comprising the amino acid sequence of SEQ ID NO:39; or (c) HVR-H1, HVR-H2, and HVR-H3 of the antibody produced by hybridoma 19C3 having ATCC Accession No. PTA-11464. In one such embodiment, the antibody comprises (a) (i) HVR-H1 comprising the amino acid sequence of SEQ ID NO:20, (ii) HVR-H2 comprising the amino acid sequence of SEQ ID NO:21, (iii) HVR-H3 comprising the amino acid sequence of SEQ ID NO:22, (iv) HVR-L1 comprising the amino acid sequence of SEQ ID NO: 17, (v) HVR-L2 comprising the amino acid sequence of SEQ ID NO: 18, and (vi) HVR-L3 comprising the amino acid sequence of SEQ ID NO: 19; (b) (i) HVR-H1 comprising the amino acid sequence of SEQ ID NO:36, (ii) HVR-H2 comprising the amino acid sequence of SEQ ID NO:37, (iii) HVR-H3 comprising the amino acid sequence of SEQ ID NO:39, (iv) HVR-L1 comprising the amino acid sequence of SEQ ID NO:33, (v) HVR-L2 comprising the amino acid sequence of SEQ ID NO:34, and (vi) HVR-L3 comprising the amino acid sequence of SEQ ID NO:35; or (c) HVR-H1, HVR-H2, HVR-H3, HVR-L1, HVR-L2 and HVR-L3 of the antibody produced by hybridoma 19C3 having ATCC Accession No. PTA-11464. In a further embodiment, the antibody comprises (i) HVR-H1 comprising the amino acid sequence of SEQ ID NO:20, (ii) HVR-H2 comprising the amino acid sequence of SEQ ID NO:21, (iii) HVR-H3 comprising the amino acid sequence of SEQ ID NO:22, (iv) HVR-L1 comprising the amino acid sequence of SEQ ID NO: 17, (v) HVR-L2 comprising the amino acid sequence of SEQ ID NO: 18, and (vi) HVR-L3 comprising the amino acid sequence of SEQ ID NO: 19, and further comprising a light chain variable domain comprising a framework FR2 sequence of SEQ ID NO:25 and an FR3 sequence of SEQ ID NO:27.

In certain embodiments, the antibody comprises (a) (i) HVR-L1 comprising the amino acid sequence of SEQ ID NO: 17, (ii) HVR-L2 comprising the amino acid sequence of SEQ ID NO: 18, and (iii) HVR-L3 comprising the amino acid sequence of SEQ ID NO: 19; (b) (i) HVR-L1 comprising the amino acid sequence of SEQ ID NO:33, (ii) HVR-L2 comprising the amino acid sequence of SEQ ID NO:34, and (iii) HVR-L3 comprising the amino acid sequence of SEQ ID NO:35; or (c) HVR-L1, HVR-L2 and HVR-L3 of the antibody produced by hybridoma 19C3 having ATCC Accession No. PTA-11464. In one such embodiment, the antibody comprises HVR-L1 comprising the amino acid sequence of SEQ ID NO: 17, HVR-L2 comprising the amino acid sequence of SEQ ID NO: 18, and HVR-L3 comprising the amino acid sequence of SEQ ID NO: 19, and further comprises a light chain variable domain comprising a framework FR2 sequence of SEQ ID NO:25 and an FR3 sequence of SEQ ID NO:27.

In certain embodiments, the antibody comprises (a) a VH sequence having at least 95% sequence identity to the amino acid sequence of SEQ ID NO: 8; (b) a VL sequence having at least 95% sequence identity to the amino acid sequence of SEQ ID NO:4; (c) a VH sequence as in (a) and a VL sequence as in (b); (d) a VH sequence having at least 95% sequence identity to the amino acid sequence of SEQ ID NO: 16; (e) a VL sequence having at least 95% sequence identity to the amino acid sequence of SEQ ID NO: 12; (f) a VH sequence as in (d) and a VL sequence as in (e); (g) a VH sequence having at least 95% sequence identity to the amino acid sequence of the VH sequence of the antibody produced by hybridoma 19C3 having ATCC Accession No. PTA-11464; (h) a VL sequence having at least 95% sequence identity to the amino acid sequence of the VL sequence of the antibody produced by hybridoma 19C3 having ATCC Accession No. PTA-11464; or (i) a VH sequence as in (g) and a VL sequence as in (h). In one such embodiment, the antibody comprises a VH sequence of SEQ ID NO:8, a VH sequence of SEQ ID NO: 16, or a VH sequence of the antibody produced by hybridoma 19C3 having ATCC Accession No. PTA-11464. In another such embodiment, the antibody comprises a VL sequence of SEQ ID NO:4, a VL sequence of SEQ ID NO: 12, or a VL sequence of the antibody produced by hybridoma 19C3 having ATCC Accession No. PTA-11464.

In a further aspect, the invention provides an antibody comprising (a) a VH sequence of SEQ ID NO:8 and a VL sequence of SEQ ID NO:4; (b) a VH sequence of SEQ ID NO:16 and a VL sequence of SEQ ID NO: 12; (c) a VH sequence and a VL sequence of the antibody produced by hybridoma 19C3 having ATCC Accession No. PTA-11464; or (d) the antibody produced by hybridoma 19C3 having ATCC Accession No. PTA-11464.

In certain embodiments, an antibody according to any of the above embodiments is an IgG1, IgG2a or IgG2b antibody.

In a further aspect, the invention provides an isolated nucleic acid encoding an antibody according to any of the above embodiments. In one embodiment, a host cell comprising the nucleic acid is provided. In another embodiment, a method of producing an antibody is provided, the method comprising culturing the host cell so that the antibody is produced.

In a further aspect, An immunoconjugate having the formula Ab-(L-D)p is provided, wherein:

(a) Ab is an antibody as in any of the above embodiment;

(b) L is a linker;

(c) D is a drug of formula $D_E$

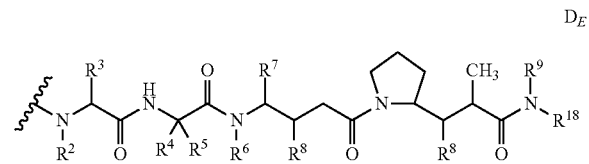

and wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl; and (d) p ranges from 1-8.

In one embodiment, the drug is an auristatin. In one such embodiment, the drug is monomethyl auristatin E (MMAE). In another embodiment, the linker is cleavable by a protease. In one such embodiment, the linker comprises a val-cit dipeptide.

In a further embodiment, the immunoconjugate has the formula:

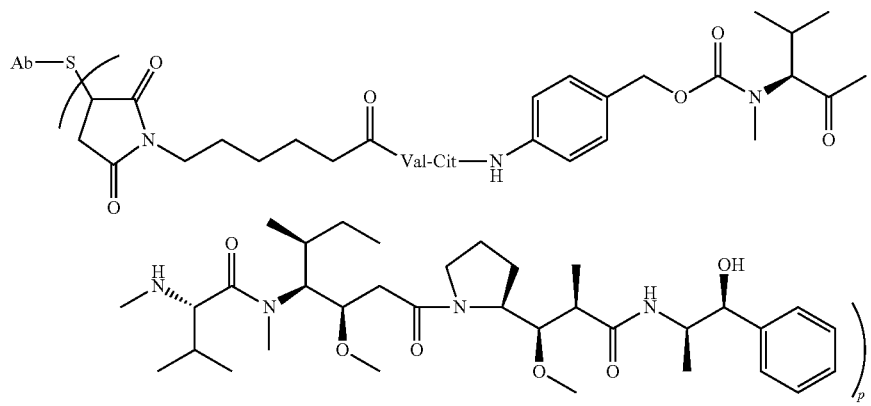

wherein S is a sulfur atom. In one such embodiment, p ranges from 2-5. In another such embodiment, the antibody comprises (i) HVR-H1 comprising the amino acid sequence of SEQ ID NO:20, (ii) HVR-H2 comprising the amino acid sequence of SEQ ID NO:21, (iii) HVR-H3 comprising the amino acid sequence of SEQ ID NO:22, (iv) HVR-L1 comprising the amino acid sequence of SEQ ID NO: 17, (v)

HVR-L2 comprising the amino acid sequence of SEQ ID NO: 18, and (vi) HVR-L3 comprising the amino acid sequence of SEQ ID NO: 19. In another such embodiment, the antibody comprises (i) HVR-H1 comprising the amino acid sequence of SEQ ID NO:36, (ii) HVR-H2 comprising the amino acid sequence of SEQ ID NO:37, (iii) HVR-H3 comprising the amino acid sequence of SEQ ID NO:39, (iv) HVR-L1 comprising the amino acid sequence of SEQ ID NO:33, (v) HVR-L2 comprising the amino acid sequence of SEQ ID NO:34, and (vi) HVR-L3 comprising the amino acid sequence of SEQ ID NO:35. In another such embodiment, the antibody comprises (a) a VH sequence of SEQ ID NO:8 and a VL sequence of SEQ ID NO:4. In another such embodiment, the antibody comprises (b) a VH sequence of SEQ ID NO: 16 and a VL sequence of SEQ ID NO: 12.

In a further aspect, the invention provides a pharmaceutical formulation comprising an immunoconjugate as in any of the above embodiments and a pharmaceutically acceptable carrier. In one embodiment, the pharmaceutical formulation further comprises an additional therapeutic agent. In one such embodiment, the additional therapeutic agent is gemcitabine. In another such embodiment, the additional therapeutic agent is an anti-MUC16 antibody conjugated to a cytotoxic agent.

In a further aspect, the invention provides an immunoconjugate as in any of the above embodiments for use as a medicament. In certain embodiments, the invention provides an immunoconjugate as in any of the above embodiments for use in treating a mesothelin-positive cancer. In one such embodiment, the mesothelin-positive cancer is selected from pancreatic cancer, ovarian cancer, lung cancer, endometrial cancer, and mesothelioma. In another such embodiment, the mesothelin-positive cancer is a dual-positive cancer.

In a further aspect, the invention provides for use of an immunoconjugate as in any of the above embodiments in the manufacture of a medicament. In one embodiment, the medicament is for treatment of a mesothelin-positive cancer. In one such embodiment, the mesothelin-positive cancer is selected from pancreatic cancer, ovarian cancer, lung cancer, endometrial cancer and mesothelioma. In another such embodiment, the mesothelin-positive cancer is a dual-positive cancer.

In another aspect, a method of treating an individual having a mesothelin-positive cancer is provided, the method comprising administering to the individual an effective amount of an immunoconjugate as in any of the above embodiments. In one embodiment, the mesothelin-positive cancer is selected from pancreatic cancer, ovarian cancer, lung cancer, endometrial cancer, and mesothelioma. In another embodiment, the mesothelin-positive cancer is a dual-positive cancer. In another embodiment, the method further comprises administering an additional therapeutic agent to the individual. In one such embodiment, the additional therapeutic agent is gemcitabine. In another such embodiment, the additional therapeutic agent is an anti-MUC16 antibody conjugated to a cytotoxic agent.

In another aspect, a method of inhibiting proliferation of a mesothelin-positive cell is provided, the method comprising exposing the cell to an immunoconjugate as in any of the above embodiments under conditions permissive for binding of the immunoconjugate to mesothelin on the surface of the cell, thereby inhibiting proliferation of the cell. In one embodiment, the cell is a pancreatic, ovarian, lung, mesothelioma, or endometrial cell. In another embodiment, the cell is a dual-positive cell.

In another aspect, the invention provides an antibody as in any of the above embodiments, wherein the antibody is conjugated to a label. In one embodiment, the label is a positron emitter. In one such embodiment, the positron emitter is $^{89}$Zr.

In another aspect, a method of detecting human mesothelin in a biological sample is provided, the method comprising contacting the biological sample with an anti-mesothelin antibody as in any of the above embodiments under conditions permissive for binding of the anti-mesothelin antibody to a naturally occurring human mesothelin, and detecting whether a complex is formed between the anti-mesothelin antibody and a naturally occurring human mesothelin in the biological sample. In one embodiment, the anti-mesothelin antibody comprises (a) HVR-H1, HVR-H2, HVR-H3, HVR-L1, HVR-L2 and HVR-L3 of the antibody produced by hybridoma 19C3 having ATCC Accession No. PTA-11464; (b) a VH sequence and a VL sequence of the antibody produced by hybridoma 19C3 having ATCC Accession No. PTA-11464; or (d) the antibody produced by hybridoma 19C3 having ATCC Accession No. PTA-11464. In another embodiment, the biological sample is a pancreatic cancer sample, ovarian cancer sample, lung cancer sample, endometrial cancer sample, or mesothelioma sample. In another embodiment, the method comprises performing immunohistochemistry on a tissue section. In another embodiment, the biological sample is serum.

In a further aspect, a method for detecting a mesothelin-positive cancer is provided, the method comprising administering a labeled anti-mesothelin antibody, wherein the anti-mesothelin antibody is as in any of the above embodiments, to a subject having or suspected of having a mesothelin-positive cancer, and detecting the labeled anti-mesothelin antibody in the subject, wherein detection of the labeled anti-mesothelin antibody indicates a mesothelin-positive cancer in the subject. In one embodiment, the labeled anti-mesothelin antibody comprises an anti-mesothelin antibody conjugated to a positron emitter. In one such embodiment, the positron emitter is $^{89}$Zr.

BRIEF DESCRIPTION OF THE FIGURES

FIG. 3 shows properties of anti-mesothelin monoclonal antibodies isolated as described in Example B.

FIG. 4 shows an alignment of the variable light chain region sequences of murine antibody 7D9 (mu7D9) and humanized variants thereof (7D9.v1 and 7D9.v3).

FIG. 5 shows an alignment of the variable heavy chain region sequences of murine antibody 7D9 (mu7D9) and humanized variants thereof (7D9.v1 and 7D9.v3).

FIG. 6 shows properties of chimeric and humanized variants of 7D9, as described in Example C.

FIG. 7 shows an alignment of the variable light chain region sequences of murine antibody 22A10 (22A10) and humanized variants thereof (hu22A10graft and 22A10.v83).

FIG. 8 shows an alignment of the variable heavy chain region sequences of murine antibody 22A10 (22A10) and humanized variants thereof (hu22A10graft and 22A10.v83).

FIG. 9A shows Scatchard analysis of humanized variants of 22A10 on stably mesothelin-transfected BJAB cells, as described in Example C.

FIG. 9B shows immunoprecipitation of mesothelin by humanized variants of 22A10 from the same stably transfected BJAB cells, as described in Example C.

FIG. 10A shows the sequences of hypervariable and framework regions of humanized variants of 7D9.

FIG. 10B shows the sequences of hypervariable and framework regions of humanized variants of 22A10.

FIG. 11 shows sequence homology among mesothelin from different species, as described in Example D. FIG. 11 discloses SEQ ID NOS 43 and 46-48, respectively, in order of appearance.

FIG. 15 discloses "EVEK," "DAEQ," and "DVER" as SEQ ID NOS 51-53, respectively.

FIG. 17 discloses "EVEK" as SEQ ID NO: 51; "Human132-212," "Cyno132-212," "Rat132-212," and "Mouse132-212" as SEQ ID NOS 54-57, respectively; human and mouse "MUT1," "MUT3," "MUT6," "MUT7," "MUT9," "MUT10," "MUT13," and "MUT15," as SEQ ID NOS 58-73, respectively; and "STKD" and "SVKD" as SEQ ID NOS 73 and 74, respectively.

FIG. 19 discloses SEQ ID NOS 54-57, respectively, in order of appearance.

FIG. 31 shows that the efficacy of the immunoconjugate h7D9.v3-vcMMAE is similar to that of the immunoconjugate h22A10.v83-vcMMAE in mesothelioma and ovarian tumor models, as described in Example P.

DETAILED DESCRIPTION OF EMBODIMENTS OF THE INVENTION

I. Definitions

Figure 1:
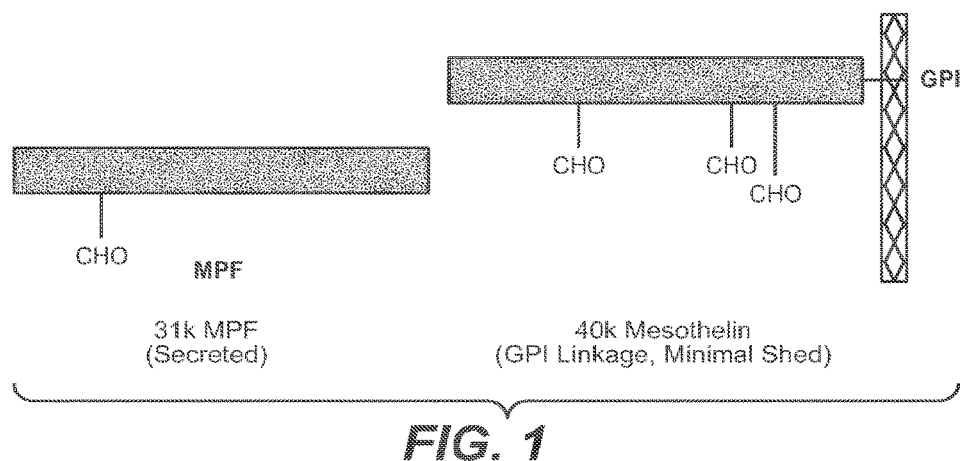
FIG. 1 shows that mesothelin is generated by proteolytic cleavage of a precursor protein into a 31 kDa shed component (referred to as megakaryocyte potentiating factor, or MPF) and a 40 kDa mesothelin component. The latter component may remain associated with the cell surface but may also be shed. "CHO" represent the four glycosylation sites, one in MPF and three in mesothelin.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-mesothelin antibody" and "an antibody that binds to mesothelin" refer to an antibody that is capable of binding mesothelin with sufficient affinity such that the antibody is useful as a diagnostic and/or therapeutic agent in targeting mesothelin. In one embodiment, the extent of binding of an anti-mesothelin antibody to an unrelated, non-mesothelin protein is less than about 10% of the binding of the antibody to mesothelin as measured, e.g., by a radioimmunoassay (RIA). In certain embodiments, an antibody that binds to mesothelin has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$M to $10^{-13}$ M). In certain embodiments, an anti-mesothelin antibody binds to an epitope of mesothelin that is conserved among mesothelin from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{31}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

The term "dual-positive cancer" refers to a cancer comprising cells that are both mesothelin- and MUC16-positive.

The term "dual-positive cell" refers to a cell that expresses both mesothelin and MUC16 on its surface.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of mesothelin" refers to naturally occurring forms of mesothelin that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-mesothelin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "mesothelin," as used herein, refers to any native, mature mesothelin which results from processing of a mesothelin precursor protein in a cell. The term includes mesothelin from any vertebrate source, including mammals such as primates (e.g. humans and cynomolgus monkeys) and rodents (e.g., mice and rats), unless otherwise indicated. The term also includes naturally occurring variants of mesothelin, e.g., splice variants or allelic variants. The amino acid sequence of an exemplary human mesothelin precursor protein is shown in SEQ ID NO:42, and an exemplary human mesothelin is shown in SEQ ID NO:43. Further exemplary mesothelin sequences are described herein.

The term "mesothelin-positive cancer" refers to a cancer comprising cells that express mesothelin on their surface.

The term "mesothelin-positive cell" refers to a cell that expresses mesothelin on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "MUC16-positive cancer" refers to a cancer comprising cells that express MUC16 on their surface.

The term "MUC16-positive cell" refers to a cell that expresses MUC16 on its surface.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on antibodies that bind to mesothelin and immunoconjugates comprising such antibodies. Antibodies and immunoconjugates of the invention are useful, e.g., for the diagnosis or treatment of mesothelin-positive cancers.

A. Exemplary Anti-Mesothelin Antibodies

In one aspect, the invention provides isolated antibodies that bind to mesothelin. Naturally occurring mesothelin results from cleavage of a mesothelin precursor protein in a cell, generating mesothelin and megakaryocyte potentiating factor (MPF), as shown in FIG. 1. Mesothelin contains a C-terminal truncation relative to the precursor protein. Such truncation may allow for attachment of a GPI anchor. Mesothelin may remain associated with the cell surface, e.g., via the GPI anchor, or mesothelin may be released from the cell (e.g., the GPI anchor may be cleaved by an as yet unidentified enzyme) to produce shed mesothelin in cell culture or animal serum.

An exemplary naturally occurring human mesothelin precursor protein sequence is provided in SEQ ID NO:42, and the corresponding mesothelin sequence is shown in SEQ ID NO:43 (corresponding to amino acids 296-580 of SEQ ID NO:42). An alternative mesothelin sequence corresponds to amino acids 296-598 of SEQ ID NO:42. SEQ ID NO:44 is a naturally occurring variant of SEQ ID NO:42, the processing of which results in a mesothelin having the sequence of SEQ ID NO:45. SEQ ID NO:45 contains an eight amino acid insertion at amino acid 116 relative to SEQ ID NO:43. The variant form of mesothelin shown in SEQ ID NO:45 appears to comprise ~5% of mesothelin transcripts in tumor cell lines.

In certain embodiments, an anti-mesothelin antibody has at least one or more of the following characteristics, in any combination:
  (a) binds to an epitope of SEQ ID NO:43 comprising (i) E153 and D174 or (ii) E211;
  (b) exhibits or does not exhibit altered or reduced binding to different glycosylated forms of mesothelin;
  (c) blocks or does not block binding of mesothelin to MUC16;
  (d) binds mesothelin with an affinity of ≤5 nM, or alternatively ≤1 nM, or alternatively ≤0.5 nM, or alternatively ≤0.1 nM, and optionally ≥0.0001 nM.

In any of the above embodiments, an antibody that does not block binding of mesothelin to MUC16 is an antibody that enhances binding of mesothelin to MUC16.

In another embodiment, an anti-mesothelin antibody binds to an epitope of SEQ ID NO:43 comprising E153 and D174. In one such embodiment, the anti-mesothelin antibody further has one or more of the following characteristics, in any combination:
  (a) does not exhibit reduced binding to glycosylated forms of mesothelin;
  (b) does not block binding of mesothelin to MUC16;
  (c) binds mesothelin with an affinity of ≤5 nM, or alternatively ≤1 nM, or alternatively ≤0.5 nM, and optionally ≥0.0001 nM.

In such embodiments, an antibody that does not block binding of mesothelin to MUC16 enhances binding of mesothelin to MUC16 and/or the antibody binds with an affinity of ≤1 nM. An exemplary antibody having the above characteristics is 7D9 and humanized variants thereof, such as h7D9.v3, disclosed herein. In any of the above embodiments, the mesothelin to which an anti-mesothelin antibody binds is human mesothelin.

In another embodiment, an anti-mesothelin antibody binds to an epitope of SEQ ID NO:43 comprising E211. In one such embodiment, the anti-mesothelin antibody further has one or more of the following characteristics:
  (a) does not block binding of mesothelin to MUC16;
  (b) binds mesothelin with an affinity of ≤5 nM, or alternatively ≤1 nM, or alternatively ≤0.5 nM, and optionally ≥0.0001 nM.

In such embodiments, an antibody that does not block binding of mesothelin to MUC16 enhances binding of mesothelin to MUC16, and/or the antibody binds with an affinity of ≤1 nM. An exemplary antibody having the above characteristics is 22A10 and humanized variants thereof, such as 22A10.v83, disclosed herein. In any of the above embodiments, the mesothelin to which an anti-mesothelin antibody binds is human mesothelin, cynomolgus monkey mesothelin, and/or rat mesothelin.

In another embodiment, an anti-mesothelin antibody:
  (a) binds to an epitope within amino acids 1-131 of SEQ ID NO:43; and
  (b) binds mesothelin with an affinity of ≤5 nM, or alternatively ≤1 nM, or alternatively ≤0.5 nM, or alternatively ≤0.1 nM, and optionally ≥0.0001 nM.

In one such embodiment, the antibody blocks binding of mesothelin to MUC16 and/or binds to an epitope within amino acids 1-64 or 1-70 of SEQ ID NO:43. In one such embodiment, the antibody displaces MUC16 bound to mesothelin. An exemplary antibody having the above characteristics is 19C3, disclosed herein. In any of the above embodiments, the mesothelin to which an anti-mesothelin antibody binds is human mesothelin.

Assays

To determine whether an anti-mesothelin antibody "binds to an epitope of SEQ ID NO:43 comprising E153 and D174," or "binds to an epitope of SEQ ID NO:43 comprising E211," those residues are mutated in a polypeptide comprising SEQ ID NO:43, and binding of the antibody to the mutated polypeptide expressed in 293 cells is tested by FACS as described in Example G, wherein a substantial reduction (≥70% reduction) or elimination of binding of the antibody to the mutated polypeptide indicates that the antibody binds to an epitope of SEQ ID NO:43 comprising E153 and D174, or comprising E211.

To determine whether an anti-mesothelin antibody "does not exhibit reduced binding to glycosylated forms of mesothelin," tagged human mesothelin is expressed in CHO cells, purified (by way of the tag) and further separated according to charge on a Mono S column into fractions with high (fraction A11), medium (A12), low (B1) and low-to-none (B5) glycosylation of mesothelin, as described in Example H. Each fraction is flowed over a chip with prebound anti-mesothelin antibody, and the on- and off-rates are measured for each fraction. If the affinities for each fraction are within 25% of one another, that indicates that the antibody does not exhibit reduced binding to glycosylated forms of mesothelin.

To determine whether an anti-mesothelin antibody "blocks binding of mesothelin to MUC16," "does not block binding of mesothelin to MUC16," or "enhances binding of mesothelin to MUC16," a MUC16 binding assay is performed, as follows. Specifically, a biotinylated fragment of MUC16 (encompassing three of the mucin repeats) is incubated with A431 cells stably expressing mesothelin in the presence or absence of anti-mesothelin antibody, and the level of MUC16-biotin binding to the cells is determined by FACS with streptavidin-PE. The MUC16 binding site of mesothelin has been tentatively mapped to the first 64 amino acids of mesothelin (Kaneko et al., *J. Biol Chem.* 284:3739-49 (2009)). Conversely, PC3 cells stably expressing MUC16 are incubated with purified mesothelin-his8 ("his8" disclosed as SEQ ID NO: 49) preincubated with anti-mesothelin antibodies, and binding of purified mesothelin-his8:antibody complexes to the MUC16-expressing cells is detected by FACS using an Alexa-647 conjugated anti-His6 antibody ("His6" disclosed as SEQ ID NO: 50). If in either of the above assays, the FACS signal is ≥50% lower in the presence of anti-mesothelin antibody than in the absence, then that antibody is considered to block binding of mesothelin to MUC16. If in either of the above assays, the FACS signal is not decreased by ≥50% in the presence of anti-mesothelin antibody, then that antibody is considered to not block binding of mesothelin to MUC16. If in the latter of the above assays, the FACS signal is increased in the presence of anti-mesothelin antibody than in the absence, then that antibody is considered to enhance binding of mesothelin to MUC16.

Whether an anti-mesothelin antibody "binds with an affinity of ≤5 nM, or alternatively ≤1 nM, or alternatively ≤0.5 nM, or alternatively ≤0.1 nM" affinity is determined according to a Biacore assay as described herein in Section II.A. 1. Specifically, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. The antigen to be used is mesothelin generated and isolated from *E. coli* as described in Example B. The antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

Antibody 7D9 and Other Embodiments

In one aspect, the invention provides an anti-mesothelin antibody comprising at least one, two, three, four, five, or six HVRs selected from (a) HVR-H1 comprising the amino acid sequence of SEQ ID NO:20; (b) HVR-H2 comprising the amino acid sequence of SEQ ID NO:21; (c) HVR-H3 comprising the amino acid sequence of SEQ ID NO:22; (d) HVR-L1 comprising the amino acid sequence of SEQ ID NO: 17; (e) HVR-L2 comprising the amino acid sequence of SEQ ID NO: 18; and (f) HVR-L3 comprising the amino acid sequence of SEQ ID NO: 19.

In one aspect, the invention provides an antibody comprising at least one, at least two, or all three VH HVR sequences selected from (a) HVR-H1 comprising the amino acid sequence of SEQ ID NO:20; (b) HVR-H2 comprising the amino acid sequence of SEQ ID NO:21; and (c) HVR-H3 comprising the amino acid sequence of SEQ ID NO:22. In one embodiment, the antibody comprises HVR-H3 comprising the amino acid sequence of SEQ ID NO:22. In another embodiment, the antibody comprises HVR-H3 comprising the amino acid sequence of SEQ ID NO:22 and HVR-L3 comprising the amino acid sequence of SEQ ID NO: 19. In a further embodiment, the antibody comprises HVR-H3 comprising the amino acid sequence of SEQ ID NO:22, HVR-L3 comprising the amino acid sequence of SEQ ID NO: 19, and HVR-H2 comprising the amino acid sequence of SEQ ID NO:21. In a further embodiment, the antibody comprises (a) HVR-H1 comprising the amino acid sequence of SEQ ID NO:20; (b) HVR-H2 comprising the amino acid sequence of SEQ ID NO:21; and (c) HVR-H3 comprising the amino acid sequence of SEQ ID NO:22.

In another aspect, the invention provides an antibody comprising at least one, at least two, or all three VL HVR sequences selected from (a) HVR-L1 comprising the amino acid sequence of SEQ ID NO: 17; (b) HVR-L2 comprising the amino acid sequence of SEQ ID NO: 18; and (c) HVR-L3 comprising the amino acid sequence of SEQ ID NO: 19. In one embodiment, the antibody comprises (a) HVR-L1 comprising the amino acid sequence of SEQ ID NO: 17; (b) HVR-L2 comprising the amino acid sequence of SEQ ID NO: 18; and (c) HVR-L3 comprising the amino acid sequence of SEQ ID NO: 19.

In another aspect, an antibody of the invention comprises (a) a VH domain comprising at least one, at least two, or all three VH HVR sequences selected from (i) HVR-H1 comprising the amino acid sequence of SEQ ID NO:20, (ii) HVR-H2 comprising the amino acid sequence of SEQ ID NO:21, and (iii) HVR-H3 comprising an amino acid sequence selected from SEQ ID NO:22; and (b) a VL domain comprising at least one, at least two, or all three VL HVR sequences selected from (i) HVR-L1 comprising the amino acid sequence of SEQ ID NO: 17, (ii) HVR-L2 comprising the amino acid sequence of SEQ ID NO: 18, and (c) HVR-L3 comprising the amino acid sequence of SEQ ID NO: 19.

In another aspect, the invention provides an antibody comprising (a) HVR-H1 comprising the amino acid sequence of SEQ ID NO:20; (b) HVR-H2 comprising the amino acid sequence of SEQ ID NO:21; (c) HVR-H3 comprising the amino acid sequence of SEQ ID NO:22; (d) HVR-L1 comprising the amino acid sequence of SEQ ID NO: 17; (e) HVR-L2 comprising the amino acid sequence of SEQ ID NO: 18; and (f) HVR-L3 comprising the amino acid sequence of SEQ ID NO:19.

In any of the above embodiments, an anti-mesothelin antibody is humanized. In one embodiment, an anti-mesothelin antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_{ATA}$, which differs from the human VH subgroup III consensus ($VH_{III}$) at 3 positions: R71A, N73T, and L78A (Carter et al., Proc. Natl. Acad. Sci. USA 89:4285 (1992)). In another embodiment, an anti-mesothelin antibody comprises HVRs as in any of the above embodiments, and further comprises a light chain variable domain comprising a framework FR2 sequence of SEQ ID NO:25 and an FR3 sequence of SEQ ID NO:27. In one such embodiment, the light chain variable domain framework is a modified human VL kappa I consensus ($VL_{KI}$) framework having FR2 sequence of SEQ ID NO:25 and an FR3 sequence of SEQ ID NO:27.

In another aspect, an anti-mesothelin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:8. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in SEQ ID NO:8. In certain embodiments, substitutions, insertions, or deletions occur in regions outside the HVRs (i.e., in the FRs). Optionally, the anti-mesothelin antibody comprises the VH sequence of SEQ ID NO:8, including post-translational modifications of that sequence. In a particular embodiment, the VH comprises one, two or three HVRs selected from: (a) HVR-H1 comprising the amino acid sequence of SEQ ID NO:20, (b) HVR-H2 comprising the amino acid sequence of SEQ ID NO:21, and (c) HVR-H3 comprising the amino acid sequence of SEQ ID NO:22.

In another aspect, an anti-mesothelin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:4. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in SEQ ID NO:4. In certain embodiments, the substitutions, insertions, or deletions occur in regions outside the HVRs (i.e., in the FRs). Optionally, the anti-mesothelin antibody comprises the VL sequence of SEQ ID NO:4, including post-translational modifications of that sequence. In a particular embodiment, the VL comprises one, two or three HVRs selected from (a) HVR-L1 comprising the amino acid sequence of SEQ ID NO: 17; (b) HVR-L2 comprising the amino acid sequence of SEQ ID NO:18; and (c) HVR-L3 comprising the amino acid sequence of SEQ ID NO:19.

In another aspect, an anti-mesothelin antibody is provided, wherein the antibody comprises a VH as in any of the embodiments provided above, and a VL as in any of the embodiments provided above. In one embodiment, the antibody comprises the VH and VL sequences in SEQ ID NO: 8 and SEQ ID NO:4, respectively, including post-translational modifications of those sequences.

In a further aspect, the invention provides an antibody that binds to the same epitope as an anti-mesothelin antibody provided herein. For example, in certain embodiments, an antibody is provided that binds to the same epitope as an anti-mesothelin antibody comprising a VH sequence of SEQ ID NO:8 and a VL sequence of SEQ ID NO:4. In certain embodiments, an antibody is provided that binds to an epitope of SEQ ID NO:43 from, within, or overlapping amino acids 152-175. In certain embodiments, an antibody is provided that binds to an epitope of SEQ ID NO:43 comprising E153 and D174. In certain such embodiments, the antibody binds to amino acid residues E153 and D174.

In a further aspect of the invention, an anti-mesothelin antibody according to any of the above embodiments is a monoclonal antibody, including a chimeric, humanized or human antibody. In one embodiment, an anti-mesothelin antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-mesothelin antibody according to any of the above embodiments may incorporate any of the features, singly or in combination, as described in Sections 1-7 below:

Antibody 22A10 and Other Embodiments

In one aspect, the invention provides an anti-mesothelin antibody comprising at least one, two, three, four, five, or six HVRs selected from (a) HVR-H1 comprising the amino acid sequence of SEQ ID NO:36; (b) HVR-H2 comprising the amino acid sequence of SEQ ID NO:37; (c) HVR-H3 comprising the amino acid sequence of SEQ ID NO:38 or 39; (d) HVR-L1 comprising the amino acid sequence of SEQ ID NO:33; (e) HVR-L2 comprising the amino acid sequence of SEQ ID NO:34; and (f) HVR-L3 comprising the amino acid sequence of SEQ ID NO:35.

In one aspect, the invention provides an antibody comprising at least one, at least two, or all three VH HVR sequences selected from (a) HVR-H1 comprising the amino acid sequence of SEQ ID NO:36; (b) HVR-H2 comprising the amino acid sequence of SEQ ID NO:37; and (c) HVR-H3 comprising the amino acid sequence of SEQ ID NO:38 or 39. In one embodiment, the antibody comprises HVR-H3 comprising the amino acid sequence of SEQ ID NO:38 or 39. In another embodiment, the antibody comprises HVR-H3 comprising the amino acid sequence of SEQ ID NO:38 or 39, and HVR-L3 comprising the amino acid sequence of SEQ ID NO:35. In a further embodiment, the antibody comprises HVR-H3 comprising the amino acid sequence of SEQ ID NO:38 or 39, HVR-L3 comprising the amino acid sequence of SEQ ID NO:35, and HVR-H2 comprising the amino acid sequence of SEQ ID NO:37. In a further embodiment, the antibody comprises (a) HVR-H1 comprising the amino acid sequence of SEQ ID NO:36; (b) HVR-H2 comprising the amino acid sequence of SEQ ID NO:37; and (c) HVR-H3 comprising the amino acid sequence of SEQ ID NO:38 or 39.

In another aspect, the invention provides an antibody comprising at least one, at least two, or all three VL HVR sequences selected from (a) HVR-L1 comprising the amino acid sequence of SEQ ID NO:33; (b) HVR-L2 comprising the amino acid sequence of SEQ ID NO:34; and (c) HVR-L3 comprising the amino acid sequence of SEQ ID NO:35. In one embodiment, the antibody comprises (a) HVR-L1 comprising the amino acid sequence of SEQ ID NO:33; (b)

HVR-L2 comprising the amino acid sequence of SEQ ID NO:34; and (c) HVR-L3 comprising the amino acid sequence of SEQ ID NO:35.

In another aspect, an antibody of the invention comprises (a) a VH domain comprising at least one, at least two, or all three VH HVR sequences selected from (i) HVR-H1 comprising the amino acid sequence of SEQ ID NO:36, (ii) HVR-H2 comprising the amino acid sequence of SEQ ID NO:37, and (iii) HVR-H3 comprising the amino acid sequence of SEQ ID NO:38 or 39; and (b) a VL domain comprising at least one, at least two, or all three VL HVR sequences selected from (i) HVR-L1 comprising the amino acid sequence of SEQ ID NO:33, (ii) HVR-L2 comprising the amino acid sequence of SEQ ID NO:34, and (c) HVR-L3 comprising the amino acid sequence of SEQ ID NO:35.

In another aspect, the invention provides an antibody comprising (a) HVR-H1 comprising the amino acid sequence of SEQ ID NO:36; (b) HVR-H2 comprising the amino acid sequence of SEQ ID NO:37; (c) HVR-H3 comprising the amino acid sequence of SEQ ID NO:38 or 39; (d) HVR-L1 comprising the amino acid sequence of SEQ ID NO:33; (e) HVR-L2 comprising the amino acid sequence of SEQ ID NO:34; and (f) HVR-L3 comprising an amino acid sequence selected from SEQ ID NO:35.

In any of the above embodiments, an anti-mesothelin antibody is humanized. In one embodiment, an anti-mesothelin antibody comprises HVRs as in any of the above embodiments, and further comprises an acceptor human framework, e.g. a human immunoglobulin framework or a human consensus framework. In certain embodiments, the human acceptor framework is $VL_{KI}$ and/or $VH_{III}$ acceptor framework.

In another aspect, an anti-mesothelin antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:16. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in SEQ ID NO: 16. In certain embodiments, substitutions, insertions, or deletions occur in regions outside the HVRs (i.e., in the FRs). Optionally, the anti-mesothelin antibody comprises the VH sequence of SEQ ID NO: 16, including post-translational modifications of that sequence. In a particular embodiment, the VH comprises one, two or three HVRs selected from: (a) HVR-H1 comprising the amino acid sequence of SEQ ID NO:36, (b) HVR-H2 comprising the amino acid sequence of SEQ ID NO:37, and (c) HVR-H3 comprising the amino acid sequence of SEQ ID NO:38 or 39.

In another aspect, an anti-mesothelin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 12. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in SEQ ID NO: 12. In certain embodiments, the substitutions, insertions, or deletions occur in regions outside the HVRs (i.e., in the FRs). Optionally, the anti-mesothelin antibody comprises the VL sequence of SEQ ID NO: 12, including post-translational modifications of that sequence. In a particular embodiment, the VL comprises one, two or three HVRs selected from (a) HVR-L1 comprising the amino acid sequence of SEQ ID NO:33; (b) HVR-L2 comprising the amino acid sequence of SEQ ID NO:34; and (c) HVR-L3 comprising the amino acid sequence of SEQ ID NO:35.

In another aspect, an anti-mesothelin antibody is provided, wherein the antibody comprises a VH as in any of the embodiments provided above, and a VL as in any of the embodiments provided above. In one embodiment, the antibody comprises the VH and VL sequences in SEQ ID NO: 16 and SEQ ID NO: 12, respectively, including post-translational modifications of those sequences.

In a further aspect, the invention provides an antibody that binds to the same epitope as an anti-mesothelin antibody provided herein. For example, in certain embodiments, an antibody is provided that binds to the same epitope as an anti-mesothelin antibody comprising a VH sequence of SEQ ID NO:16 and a VL sequence of SEQ ID NO:12. In certain embodiments, an antibody is provided that binds to an epitope of SEQ ID NO:43 from, within, or overlapping amino acids 211-327. In certain embodiments, an antibody is provided that binds to an epitope of SEQ ID NO:43 comprising E211. In certain such embodiments, the antibody binds to amino acid residue E211.

In a further aspect of the invention, an anti-mesothelin antibody according to any of the above embodiments is a monoclonal antibody, including a chimeric, humanized or human antibody. In one embodiment, an anti-mesothelin antibody is an antibody fragment, e.g., a Fv, Fab, Fab', scFv, diabody, or $F(ab')_2$ fragment. In another embodiment, the antibody is a substantially full length antibody, e.g., an IgG2a antibody or other antibody class or isotype as defined herein.

In a further aspect, an anti-mesothelin antibody according to any of the above embodiments may incorporate any of the features, singly or in combination, as described in Sections 1-7 below:

Antibody 19C3 and Other Embodiments

In one aspect, the invention provides an anti-mesothelin antibody comprising at least one, two, three, four, five, or six HVRs of the antibody produced by hybridoma 19C3 having ATCC Accession No. PTA-11464. For purposes of this section, HVRs are delineated by the amino acid ranges corresponding to CDRs, as defined herein.

In one aspect, the invention provides an antibody comprising at least one, at least two, or all three VH HVR sequences of the antibody produced by hybridoma 19C3 having ATCC Accession No. PTA-11464. In one embodiment, the antibody comprises HVR-H3 of the antibody produced by hybridoma 19C3 having ATCC Accession No. PTA-11464. In another embodiment, the antibody comprises HVR-H3 and HVR-L3 of the antibody produced by hybridoma 19C3 having ATCC Accession No. PTA-11464. In a further embodiment, the antibody comprises HVR-H3, HVR-L3, and HVR-H2 of the antibody produced by hybridoma 19C3 having ATCC Accession No. PTA-11464. In a further embodiment, the antibody comprises HVR-H1, HVR-H2, and HVR-H3 of the antibody produced by hybridoma 19C3 having ATCC Accession No. PTA-11464.

In another aspect, the invention provides an antibody comprising at least one, at least two, or all three VL HVR sequences of the antibody produced by hybridoma 19C3 having ATCC Accession No. PTA-11464. In one embodiment, the antibody comprises HVR-L1, HVR-L2, and HVR-L3 of the antibody produced by hybridoma 19C3 having ATCC Accession No. PTA-11464.

In another aspect, an antibody of the invention comprises (a) a VH domain comprising at least one, at least two, or all three VH HVR sequences of the antibody produced by hybridoma 19C3 having ATCC Accession No. PTA-11464; and (b) a VL domain comprising at least one, at least two, or all three VL HVR sequences of the antibody produced by hybridoma 19C3 having ATCC Accession No. PTA-11464.

In another aspect, the invention provides an antibody comprising HVR-H1, HVR-H2, HVR-H3, HVR-L1, HVR-L2, and HVR-L3 of the antibody produced by hybridoma 19C3 having ATCC Accession No. PTA-11464.

In any of the above embodiments, an anti-mesothelin antibody is humanized. In one such embodiment, the antibody is a humanized form of the antibody produced by hybridoma 19C3 having ATCC Accession No. PTA-11464. In a further embodiment, an anti-mesothelin antibody comprises HVRs as in any of the above embodiments, and further comprises an acceptor human framework, e.g. a human immunoglobulin framework or a human consensus framework.

In another aspect, an anti-mesothelin antibody comprises a heavy chain variable domain (VH) sequence having at least 90%, 91%, 92%, 93%, 94%, 95%, 96%, 97%, 98%, 99%, or 100% sequence identity to the VH of the antibody produced by hybridoma 19C3 having ATCC Accession No. PTA-11464. In certain embodiments, a VH sequence containing substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in the VH of the antibody produced by hybridoma 19C3 having ATCC Accession No. PTA-11464. In certain embodiments, substitutions, insertions, or deletions occur in regions outside the HVRs (i.e., in the FRs). Optionally, the anti-mesothelin antibody comprises the VH sequence of the antibody produced by hybridoma 19C3 having ATCC Accession No. PTA-11464, including post-translational modifications of that sequence. In a particular embodiment, the VH comprises one, two, or three HVRs selected from HVR-H1, HVR-H2, and HVR-H3 of the antibody produced by hybridoma 19C3 having ATCC Accession No. PTA-11464.

In another aspect, an anti-mesothelin antibody is provided, wherein the antibody comprises a light chain variable domain (VL) having at least 90%, 91%, 92%, 93%, 94%, 95%, 96%, 97%, 98%, 99%, or 100% sequence identity to the VL of the antibody produced by hybridoma 19C3 having ATCC Accession No. PTA-11464. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-mesothelin antibody comprising that sequence retains the ability to bind to mesothelin. In certain embodiments, a total of 1 to 10 amino acids have been substituted, inserted and/or deleted in the VL of the antibody produced by hybridoma 19C3 having ATCC Accession No. PTA-11464. In certain embodiments, the substitutions, insertions, or deletions occur in regions outside the HVRs (i.e., in the FRs). Optionally, the anti-mesothelin antibody comprises the VL sequence of the antibody produced by hybridoma 19C3 having ATCC Accession No. PTA-11464, including post-translational modifications of that sequence. In a particular embodiment, the VL comprises one, two or three HVRs selected from HVR-L1, HVR-L2, and HVR-L3 of the antibody produced by hybridoma 19C3 having ATCC Accession No. PTA-11464.

In another aspect, an anti-mesothelin antibody is provided, wherein the antibody comprises a VH as in any of the embodiments provided above, and a VL as in any of the embodiments provided above. In one embodiment, the antibody comprises the VH and VL sequences of the antibody produced by hybridoma 19C3 having ATCC Accession No. PTA-11464, respectively, including post-translational modifications of those sequences.

In a further aspect, the invention provides an antibody that binds to the same epitope as an anti-mesothelin antibody provided herein. For example, in certain embodiments, an antibody is provided that binds to the same epitope as the antibody produced by hybridoma 19C3 having ATCC Accession No. PTA-11464.

In a further aspect of the invention, an anti-mesothelin antibody according to any of the above embodiments is a monoclonal antibody, including a chimeric, humanized or human antibody. In one embodiment, an anti-mesothelin antibody is an antibody fragment, e.g., a Fv, Fab, Fab', scFv, diabody, or F(ab')$_2$ fragment. In another embodiment, the antibody is a substantially full length antibody, e.g., an IgG2b antibody or other antibody class or isotype as defined herein.

In a further aspect, an anti-mesothelin antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20 T; Packard) is added, and the plates are counted on a TOP- COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $106 M^{-1} s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact human antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for mesothelin and the other is for any other antigen. In certain embodiments, bispecific antibodies may bind to two different epitopes of mesothelin. Bispecific antibodies may also be used to localize cytotoxic agents to cells which express mesothelin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to mesothelin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No.

6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-mesothelin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-mesothelin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-mesothelin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gemgross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-mesothelin antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, FACS or Western blot.

In another aspect, competition assays may be used to identify an antibody that competes with any of the antibodies described herein for binding to mesothelin. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized mesothelin is incubated in a solution comprising a first labeled antibody that binds to mesothelin (e.g., any of the antibodies described herein) and a second unlabeled antibody that is being tested for its ability to compete with the first antibody for binding to mesothelin. The second antibody may be present in a hybridoma supernatant. As a control, immobilized mesothelin is incubated in a solution comprising the first labeled antibody but not the second unlabeled antibody. After incubation under conditions permissive for binding of the first antibody to mesothelin, excess unbound antibody is removed, and the amount of label associated with immobilized mesothelin is measured. If the amount of label associated with immobilized mesothelin is substantially reduced in the test sample relative to the control sample, then that indicates that the second antibody is competing with the first antibody for binding to mesothelin. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-mesothelin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and monomethyl auristatin F (MMAF)) (see U.S. Pat. Nos. 5,635,483 and 5,780,588, and 7,498,298); a dolastatin; a calicheamicin or derivative thereof (see U.S. Pat. Nos. 5,712,374, 5,714, 586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF. (See U.S. Pat. Nos. 7,659,241, 7,498,298, and 7,745,394.)

A peptidic drug moiety may be selected from Formulas $D_E$ and $D_F$ below:

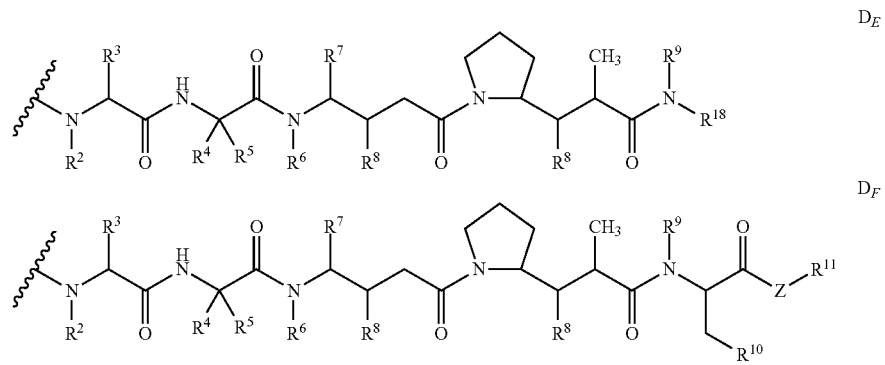

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —$(CR^aR^b)_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —$(R^{13}O)_m$—$R^{14}$, or —$(R^{13}O)_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of $R^{15}$ is independently H, COOH, —$(CH_2)_n$—$N(R^{16})_2$, —$(CH_2)_n$—$SO_3H$, or —$(CH_2)_n$—$SO_3$—$C_1$-$C_8$ alkyl;

each occurrence of $R^{16}$ is independently H, $C_1$-$C_8$ alkyl, or —$(CH_2)_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

The immunuoconjugates or ADCs herein expressly contemplate, but are not limited to such conjugates prepared with cross-linker reagents including, but not limited to, BMPS (3-Maleimidopropionic acid N-hydroxysuccinimide ester), EMCS (6-Maleimidohexanoic acid N-hydroxysuccinimide ester), GMBS (N-[Gamma-Maleimidobutyryloxy] succinimide ester), HBVS (1,6-Hexane-bis-vinylsulfone), LC-SMCC (Succinimidyl 4-(N-maleimidomethyl)cyclohexane-1-carboxy-(6-amidocaproate)), MBS (m-Maleimidobenzoyl-N-hydroxysuccinimide ester), MPBH (4-(4-N-Maleimidophenyl)butyric acid hydrazide-HCl), SBAP (Succinimidyl 3-(bromoacetamido)propionate), SIA (Succinimidyl iodoacetate), SIAB (Succinimidyl (4-iodoacetyl) aminobenzoate), SMCC (Succinimidyl-4-(N-maleimidomethyl)cyclohexane-1-carboxylate), SMPB (Succinimidyl 4-(p-maleimidophenyl)butyrate), SMPH (Succinimidyl 6-[(beta-maleimidopropionamido)hexanoate]), sulfo-EMCS (N-epsilon-Maleimidocaproyl-oxysulfosuccinimide ester), sulfo-GMBS (N-(gamma-Maleimidobutyryl-oxy) sulfosuccinimide ester), sulfo-KMUS (N-(kappa-Maleimidoundecanoyloxy) sulfosuccinimide ester), sulfo-MBS (m-Maleimidobenzoyl-N-hydroxysulfosuccinimide ester), sulfo-SIAB (Sulfosuccinimidyl (4-iodoacetyl)aminobenzoate), sulfo-SMCC (Sulfosuccinimidyl-4-(N-maleimidomethyl) cyclohexane-1-carboxylate), and sulfo-SMPB (Sulfosuccinimidyl 4-(p-maleimidophenyl)butyrate), and SVSB (succinimidyl-(4-vinylsulfone)benzoate) which are commercially available (e.g., from Pierce Biotechnology, Inc., Rockford, Ill., U.S.A).

Immunoconjugates Comprising Auristatins and Dolastatins

In some embodiments, an immunoconjugate comprises an antibody of the invention conjugated to dolastatin or a dolastatin peptidic analog or derivative, e.g., an auristatin (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —OCH$_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —OCH$_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —CH($R^{15}$)$_2$, wherein $R^{15}$ is —(CH$_2$)$_n$—N($R^{16}$)$_2$, and $R^{16}$ is —C$_1$-C$_8$ alkyl or —(CH$_2$)$_n$—COOH.

In another embodiment, when Z is —NH, $R^{11}$ is —CH($R^{15}$)$_2$, wherein $R^{15}$ is —(CH$_2$)$_n$—SO$_3$H.

An exemplary auristatin embodiment of formula D$_E$ is MMAE (monomethyl auristatin E), wherein the wavy line indicates the covalent attachment to a linker of an antibody-drug conjugate:

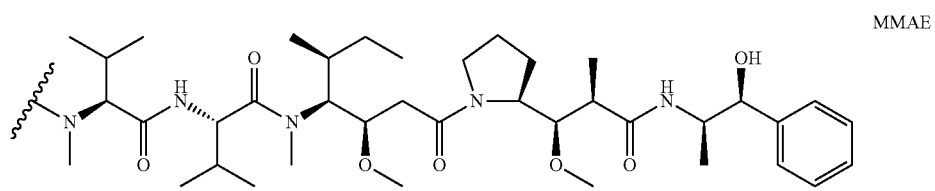 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

MMAE

An exemplary auristatin embodiment of formula D$_F$ is MMAF (monomethyl auristatin F, a variant of auristatin E (MMAE) with a phenylalanine at the C-terminus of the drug), wherein the wavy line indicates the covalent attachment to a linker of an antibody-drug conjugate (see US 2005/0238649 and Doronina et al. (2006) *Bioconjugate Chem.* 17:114-124):

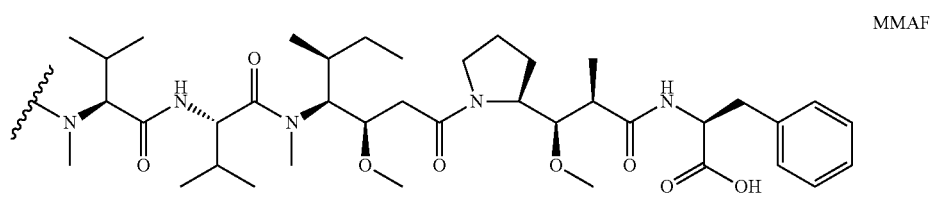 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

MMAF

In one aspect, hydrophilic groups including but not limited to, triethylene glycol esters (TEG), as shown above, can be attached to the drug moiety at $R^{11}$. Without being bound by any particular theory, the hydrophilic groups assist in the internalization and non-agglomeration of the drug moiety.

Exemplary embodiments of ADCs comprising an auristatin/dolastatin or derivative thereof are described in US 2005/0238649 A1 and Doronina et al. (2006) *Bioconjugate Chem.* 17:114-124, which is expressly incorporated herein by reference. Exemplary embodiments of ADCs comprising MMAE or MMAF and various linker components have the following structures and abbreviations (wherein "Ab" is an antibody; p is the drug load (average number of drug moieties per antibody) and ranges from about 1 to about 8; "vc" is "val-cit," i.e., a valine-citrulline dipeptide; and "S" is a sulfur atom:

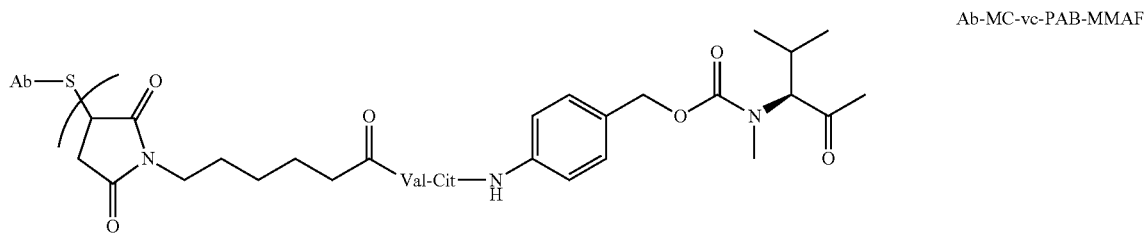

Ab-MC-vc-PAB-MMAF

-continued

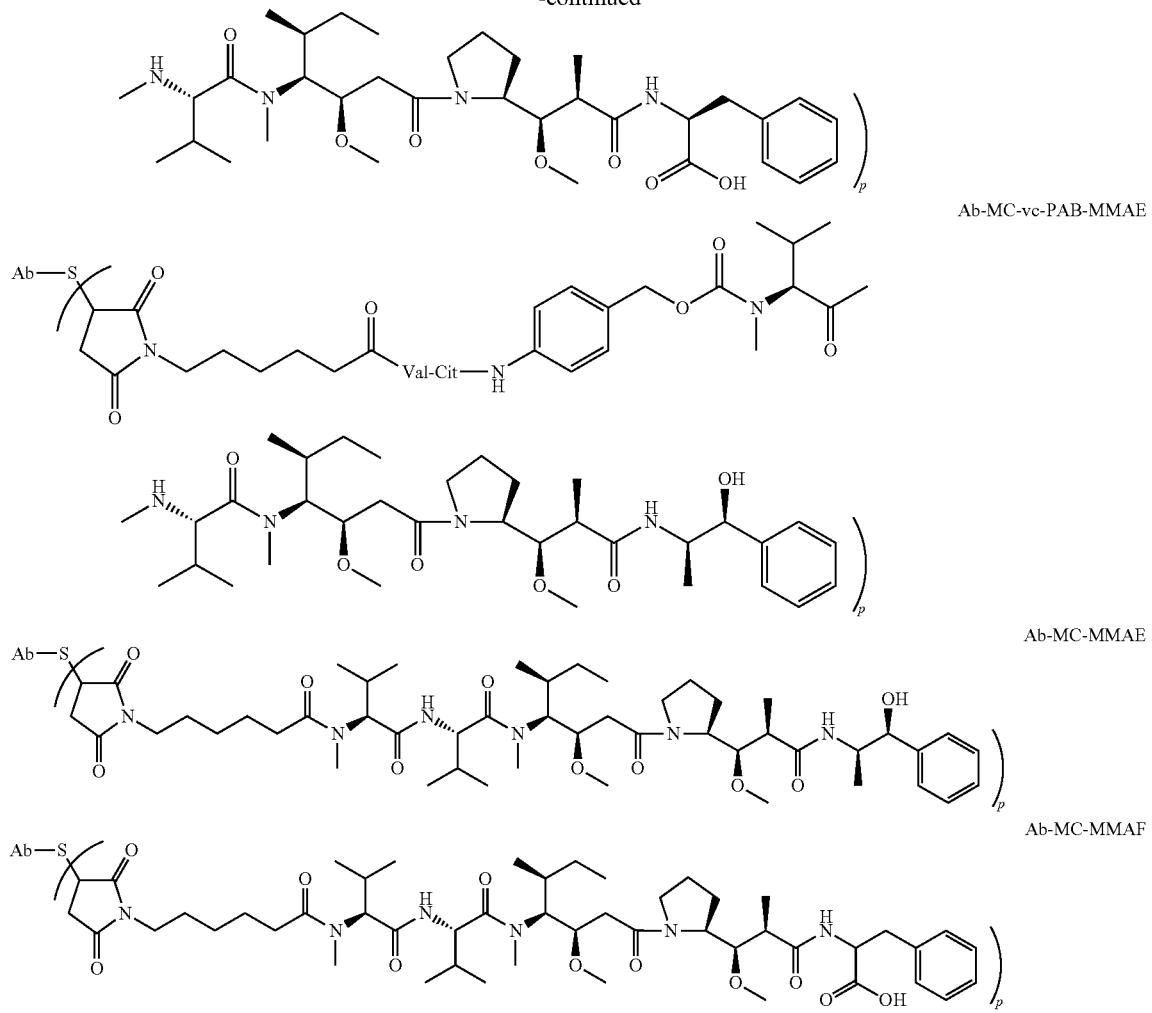

Exemplary embodiments of ADCs comprising MMAF and various linker components further include Ab-MC-PAB-MMAF and Ab-PAB-MMAF. Interestingly, immunoconjugates comprising MMAF attached to an antibody by a linker that is not proteolytically cleavable have been shown to possess activity comparable to immunoconjugates comprising MMAF attached to an antibody by a proteolytically cleavable linker. See, Doronina et al. (2006) *Bioconjugate Chem.* 17:114-124. In such instances, drug release is believed to be effected by antibody degradation in the cell. Id.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. Auristatin/dolastatin drug moieties may be prepared according to the methods of: US 2005/0238649 A1; U.S. Pat. No. 5,635,483; U.S. Pat. No. 5,780,588; Pettit et al (1989) *J. Am. Chem. Soc.* 111: 5463-5465; Pettit et al (1998) *Anti-Cancer Drug Design* 13:243-277; Pettit, G. R., et al. *Synthesis*, 1996, 719-725; Pettit et al (1996) *J. Chem. Soc. Perkin Trans.* 1 5:859-863; and Doronina (2003) *Nat. Biotechnol.* 21(7):778-784.

In particular, auristatin/dolastatin drug moieties of formula $D_F$, such as MMAF and derivatives thereof, may be prepared using methods described in US 2005/0238649 A1 and Doronina et al. (2006) *Bioconjugate Chem.* 17:114-124. Auristatin/dolastatin drug moieties of formula $D_E$, such as MMAE and derivatives thereof, may be prepared using methods described in Doronina et al. (2003) *Nat. Biotech.* 21:778-784. Drug-linker moieties MC-MMAF, MC-MMAE, MC-vc-PAB-MMAF, and MC-vc-PAB-MMAE may be conveniently synthesized by routine methods, e.g., as described in Doronina et al. (2003) *Nat. Biotech.* 21:778-784, and Patent Application Publication No. US 2005/0238649 A1, and then conjugated to an antibody of interest.

E. Methods and Compositions for Diagnostics and Detection

In certain embodiments, any of the anti-mesothelin antibodies provided herein is useful for detecting the presence of mesothelin in a biological sample. The term "detecting" as used herein encompasses quantitative or qualitative detection. A "biological sample" comprises, e.g., a cell or tissue (e.g., biopsy material, including cancerous or potentially cancerous pancreatic, ovarian, lung, or endometrial tissue, or mesothelioma), or serum.

In one embodiment, an anti-mesothelin antibody for use in a method of diagnosis or detection is provided. In a further aspect, a method of detecting the presence of mesothelin in a biological sample is provided. In certain embodiments, the method comprises contacting the biological sample with an anti-mesothelin antibody as described herein under conditions permissive for binding of the anti-mesothelin antibody to mesothelin, and detecting whether a complex is formed between the anti-mesothelin antibody and mesothelin in the biological sample. Such method may be an in vitro or in vivo method. In one embodiment, an anti-mesothelin antibody is used to select subjects eligible for therapy with an anti-mesothelin antibody, e.g. where mesothelin is a biomarker for selection of patients. In a further embodiment, the biological sample is serum, e.g., wherein mesothelin that has been shed from cancer cells into the serum is detected.

In a further embodiment, an anti-mesothelin antibody is used in vivo to detect, e.g., by in vivo imaging, a mesothelin-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a mesothelin-positive cancer in a subject, the method comprising administering a labeled anti-mesothelin antibody to a subject having or suspected of having a mesothelin-positive cancer, and detecting the labeled anti-mesothelin antibody in the subject, wherein detection of the labeled anti-mesothelin antibody indicates a mesothelin-positive cancer in the subject. In certain of such embodiments, the labeled anti-mesothelin antibody comprises an anti-mesothelin antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-mesothelin antibody immobilized to a substrate with a biological sample to be tested for the presence of mesothelin, exposing the substrate to a second anti-mesothelin antibody, and detecting whether the second anti-mesothelin is bound to a complex between the first anti-mesothelin antibody and mesothelin in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous pancreatic, ovarian, lung or endometrial tissue, or mesothelioma), or serum, i.e., serum in which mesothelin has been shed. In certain embodiments, the first or second anti-mesothelin antibody is any of the antibodies described herein. In such embodiments, the second anti-mesothelin antibody may be 19C3 or antibodies derived from 19C3 as described herein.

Exemplary disorders that may be diagnosed or detected according to any of the above embodiments include mesothelin-positive cancers, such as mesothelin-positive pancreatic cancer (including pancreatic ductal adenocarcinoma), mesothelin-positive ovarian cancer (including ovarian serous adenocarcinoma), mesothelin-positive lung cancer (including non-small cell lung carcinoma (NSCLC)), mesothelioma, and mesothelin-positive endometrial cancer. In one embodiment, a mesothelin-positive cancer is a cancer that receives an anti-mesothelin immunohistochemistry (IHC) score greater than "0," which corresponds to very weak or no staining in >90% of tumor cells, under the conditions described herein in Example J. In another embodiment, a mesothelin-positive cancer expresses mesothelin at a 1+, 2+ or 3+ level, as defined under the conditions described herein in Example J. A mesothelin-positive cancer according to any of the above embodiments may be a dual-positive cancer.

In certain embodiments, labeled anti-mesothelin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 0-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-mesothelin antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, it may be desirable to further provide gemcitabine, e.g., for the treatment of mesothelin-positive cancer such as mesothelin-positive pancreatic cancer (pancreatic adenocarcinoma). In another example, it may be desirable to further provide an anti-MUC16 antibody conjugated to a cytotoxic agent, e.g., for the treatment of mesothelin-positive cancer or dual-positive cancer such as mesothelin-positive ovarian cancer (ovarian serous adenocarcinoma) or dual-positive ovarian cancer. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-mesothelin antibodies or immunoconjugates provided herein may be used in methods, e.g., therapeutic methods.

In one aspect, an anti-mesothelin antibody or immunoconjugate provided herein is used in a method of inhibiting proliferation of a mesothelin-positive cell, the method comprising exposing the cell to the anti-mesothelin antibody or immunoconjugate under conditions permissive for binding of the anti-mesothelin antibody or immunoconjugate to mesothelin on the surface of the cell, thereby inhibiting the proliferation of the cell. In certain embodiments, the method is an in vitro or an in vivo method. In further embodiments, the cell is a pancreatic, ovarian, lung, mesothelioma, or endometrial cell. In further embodiments, the cell is a dual-positive cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-mesothelin antibody or immunoconjugate for use as a medicament is provided. In further aspects, an anti-mesothelin antibody or immunoconjugate for use in a method of treatment is provided. In certain embodiments, an anti-mesothelin antibody or immunoconjugate for use in treating mesothelin-positive cancer is provided. In certain embodiments, the invention provides an anti-mesothelin antibody or immunoconjugate for use in a method of treating an individual having a mesothelin-positive cancer, the method comprising administering to the individual an effective amount of the anti-mesothelin antibody or immunoconjugate. In one such embodiment, the method further comprises administering to the individual an effective amount of at least one additional therapeutic agent, e.g., as described below.

In a further aspect, the invention provides for the use of an anti-mesothelin antibody or immunoconjugate in the manufacture or preparation of a medicament. In one embodiment, the medicament is for treatment of mesothelin-positive cancer. In a further embodiment, the medicament is for use in a method of treating mesothelin-positive cancer, the method comprising administering to an individual having mesothelin-positive cancer an effective amount of the medicament. In one such embodiment, the method further comprises administering to the individual an effective amount of at least one additional therapeutic agent, e.g., as described below.

In a further aspect, the invention provides a method for treating mesothelin-positive cancer. In one embodiment, the method comprises administering to an individual having such mesothelin-positive cancer an effective amount of an anti-mesothelin antibody or immunoconjugate. In one such embodiment, the method further comprises administering to the individual an effective amount of at least one additional therapeutic agent, as described below.

A mesothelin-positive cancer according to any of the above embodiments may be, e.g., mesothelin-positive pancreatic cancer (including pancreatic ductal adenocarcinoma), mesothelin-positive ovarian cancer (including ovarian serous adenocarcinoma), mesothelin-positive lung cancer (including non-small cell lung carcinoma (NSCLC)), mesothelioma, and mesothelin-positive endometrial cancer. In one embodiment, a mesothelin-positive cancer is a cancer that receives an anti-mesothelin immunohistochemistry (IHC) score greater than "0," which corresponds to very weak or no staining in >90% of tumor cells, under the conditions described herein in Example J. In another embodiment, a mesothelin-positive cancer expresses mesothelin at a 1+, 2+ or 3+ level, as defined under the conditions described herein in Example J. A mesothelin-positive cancer according to any of the above embodiments may be a dual-positive cancer.

An "individual" according to any of the above embodiments may be a human.

In a further aspect, the invention provides pharmaceutical formulations comprising any of the anti-mesothelin antibodies or immunoconjugate provided herein, e.g., for use in any of the above therapeutic methods. In one embodiment, a pharmaceutical formulation comprises any of the anti-mesothelin antibodies or immunoconjugates provided herein and a pharmaceutically acceptable carrier. In another embodiment, a pharmaceutical formulation comprises any of the anti-mesothelin antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is gemcitabine. In certain embodiments, an additional therapeutic agent is an anti-MUC16 antibody conjugated to a cytotoxic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-mesothelin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

I. Deposit of Biological Material

The following biological material has been deposited with the American Type Culture Collection, 10801 University Boulevard, Manassas, Va. 20110-2209, USA (ATCC):

| Hybridoma Designation | ATCC No. | Deposit Date |
|---|---|---|
| MPF: 3542 (19C3.1.2) | PTA-11464 | Nov. 9, 2010 |

The above-referenced deposited hybridoma produces the 19C3 antibody referred to herein.

This deposit was made under the provisions of the Budapest Treaty on the International Recognition of the Deposit of Microorganisms for the Purpose of Patent Procedure and the Regulations thereunder (Budapest Treaty). This assures the maintenance of a viable culture of the deposit for 30 years from the date of deposit and for at least five (5) years after the most recent request for furnishing of a sample of the deposit. The deposit will be made available by the ATCC under the terms of the Budapest Treaty, and subject to an agreement between Genentech, Inc., and the ATCC, which assures that all restrictions imposed by the depositor on the availability to the public of the deposited material will be irrevocably removed upon the granting of the pertinent U.S. patent, assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. § 122 and the Commissioner's rules pursuant thereto (including 37 C.F.R. § 1.14 with particular reference to 886 OG 638).

III. Examples

The following are examples of methods and compositions of the invention. It is understood that various other embodiments may be practiced, given the general description provided above.

A. Human Mesothelin Gene Expression

Figure 2:
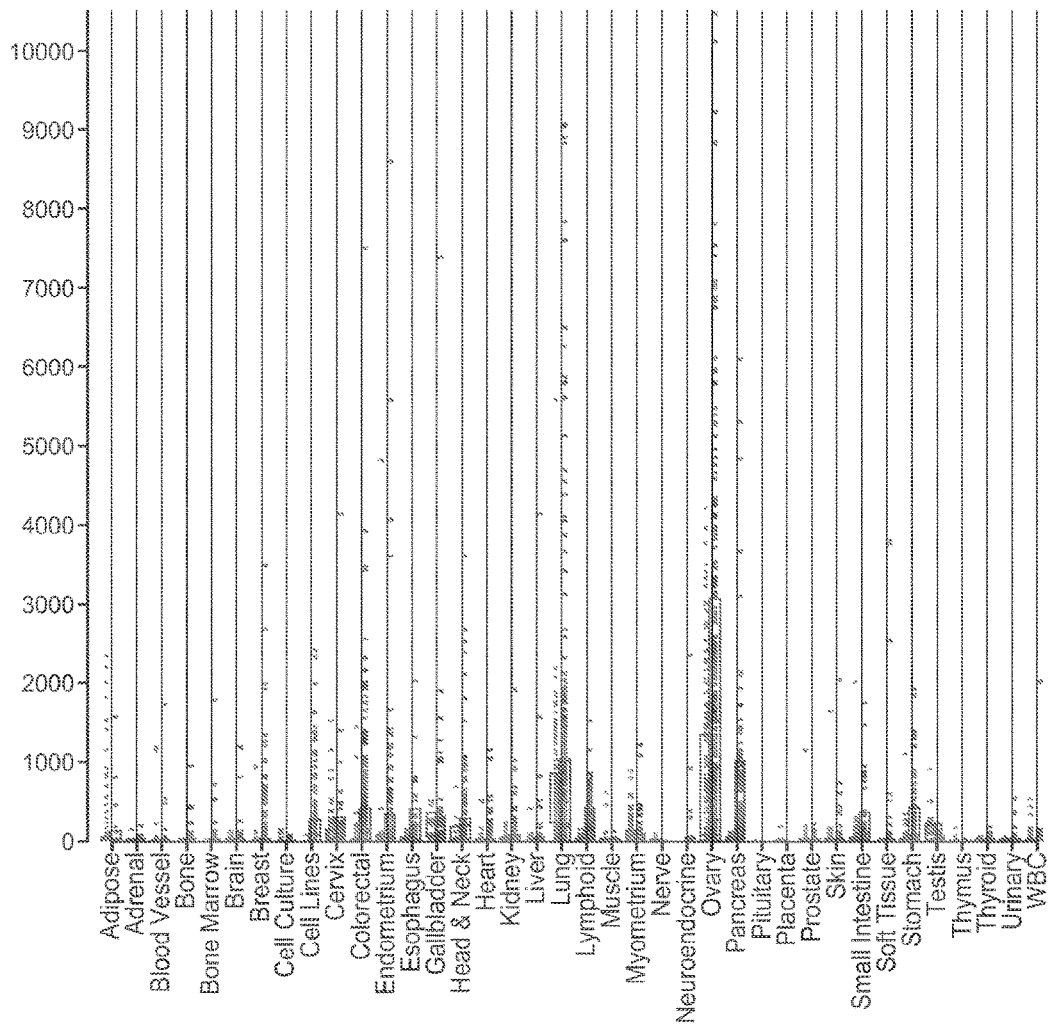
FIG. 2 shows a graphic representation of the levels of human mesothelin gene expression in various tissues, as described in Example A.

Human mesothelin gene expression was analyzed using a proprietary database containing gene expression information (GeneExpress®, Gene Logic Inc., Gaithersburg, Md.). Graphical analysis of the GeneExpress® database was conducted using a microarray profile viewer. FIG. 2 is a graphic representation of human mesothelin gene expression in various tissues, which are listed on the left. The scale across the top of the graph indicates gene expression levels based on hybridization signal intensity. Dots appear both above and below the line adjacent to each listed tissue. The dots appearing above the line represent gene expression in normal tissue, and the dots appearing below the line represent gene expression in tumor and diseased tissue. FIG. 2 shows increased mesothelin gene expression in certain tumor or diseased tissues relative to their normal counterparts. In particular, mesothelin shows substantial overexpression in ovarian, pancreatic, endometrial and lung tumors, including adenocarcinomas and mesotheliomas. Human mesothelin expression is essentially absent in normal tissues except for normal mesothelia (peritoneum, pericardium, and pleura).

B. Antibody Generation

Monoclonal antibodies against human mesothelin were generated using the following procedures. Either human MPF:mesothelin (amino acids 34-580 of SEQ ID NO:42) or human mesothelin (SEQ ID NO:43, corresponding to amino acids 296-580 of SEQ ID NO:42), each fused to an N-terminal unizyme His (HQ)-tag, was expressed in E. Coli 58F3 and purified on a Ni-NTA column (Qiagen), followed by gel filtration on a SUPERDEX™ 200 column in 20 mM MES pH 6.0, 6M GdnHCl as previously described (Kirchhofer et al., 2003) and dialysis into 1 mM HCl for storage at −80° C.

Five Balb/c mice (Charles River Laboratories, Hollister, Calif.) were hyperimmunized six times with a 2 µg mixture of the two antigens in Ribi adjuvant (Ribi Immunochem Research, Inc., Hamilton, Mo.). The two best mice were chosen based on high antibody titers by direct ELISA and their B-cells were pooled and fused with mouse myeloma cells (X63.Ag8.653; American Type Culture Collection, Manassas, Va.) using a modified protocol analogous to one previously described (Koehler and Milstein, 1975; Hongo et al., 1995). After 10-12 days, supernatants were harvested from hybridomas and screened for binding to both antigens (separately) by direct ELISA. To verify recognition of properly folded, glycosylated cell surface expressed mesothelin, ELISA-positive supernatants were further screened by fluorescence-activated cell sorting (FACS) on gD-mesothelin transfected SVT2 cells (gD is an N-terminal epitope tag used as a positive control with anti-gD antibodies). Positive hybridomas were subcloned twice by limiting dilution and eleven were scaled up and antibodies purified by protein A chromatography.

FIG. 3 shows the isolated monoclonal antibodies, along with certain properties to be described in further detail below.

C. Humanization of 7D9 and 22A10

Monoclonal antibodies 7D9 and 22A10 were humanized as described below. Residue numbers are according to Kabat et al., Sequences of proteins of immunological interest, 5th Ed., Public Health Service, National Institutes of Health, Bethesda, Md. (1991).

1. Humanization of 7D9 a) Cloning of Murine 7D9 Variable Domains

Figure 4:
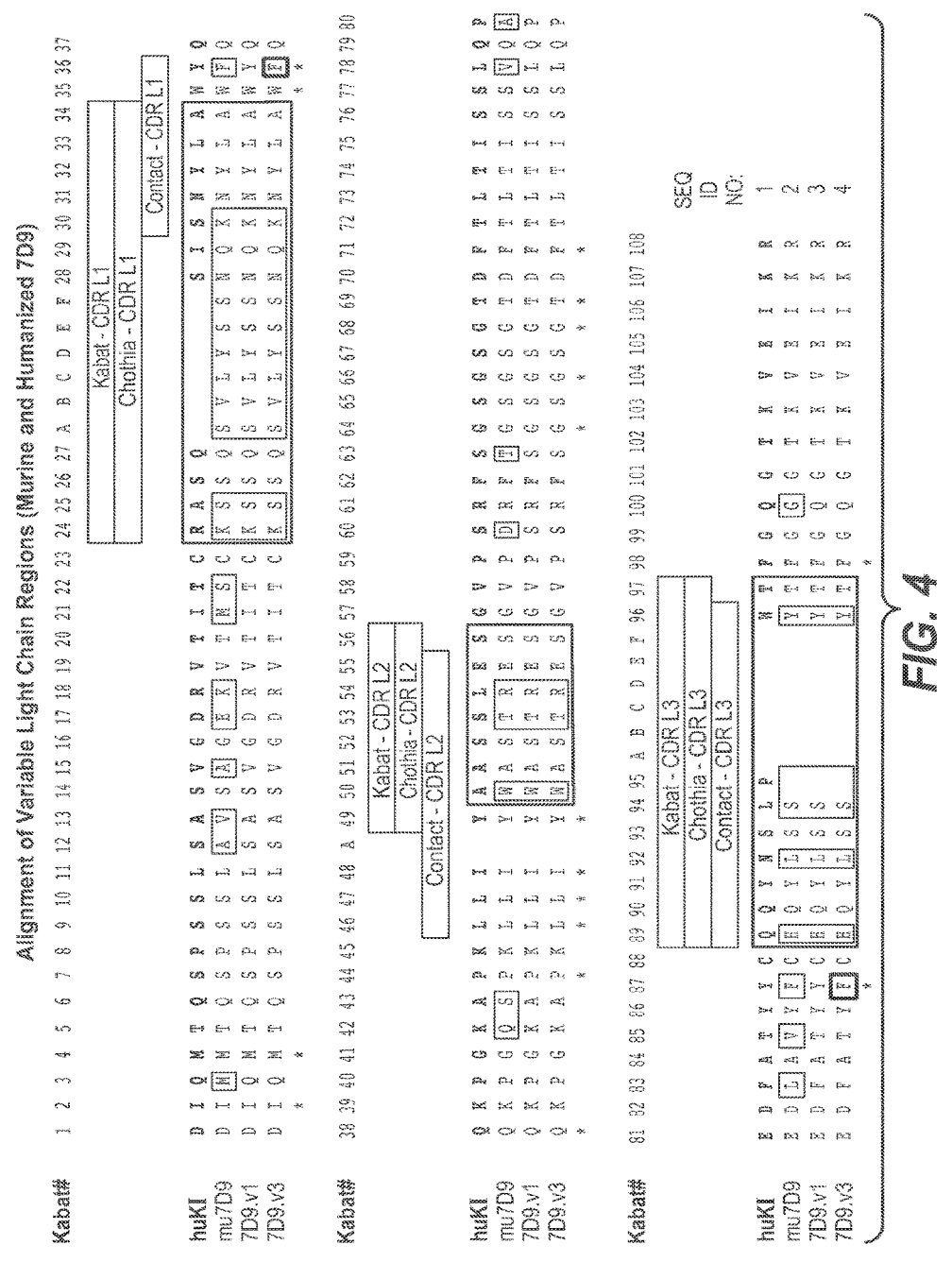
Figure 5:
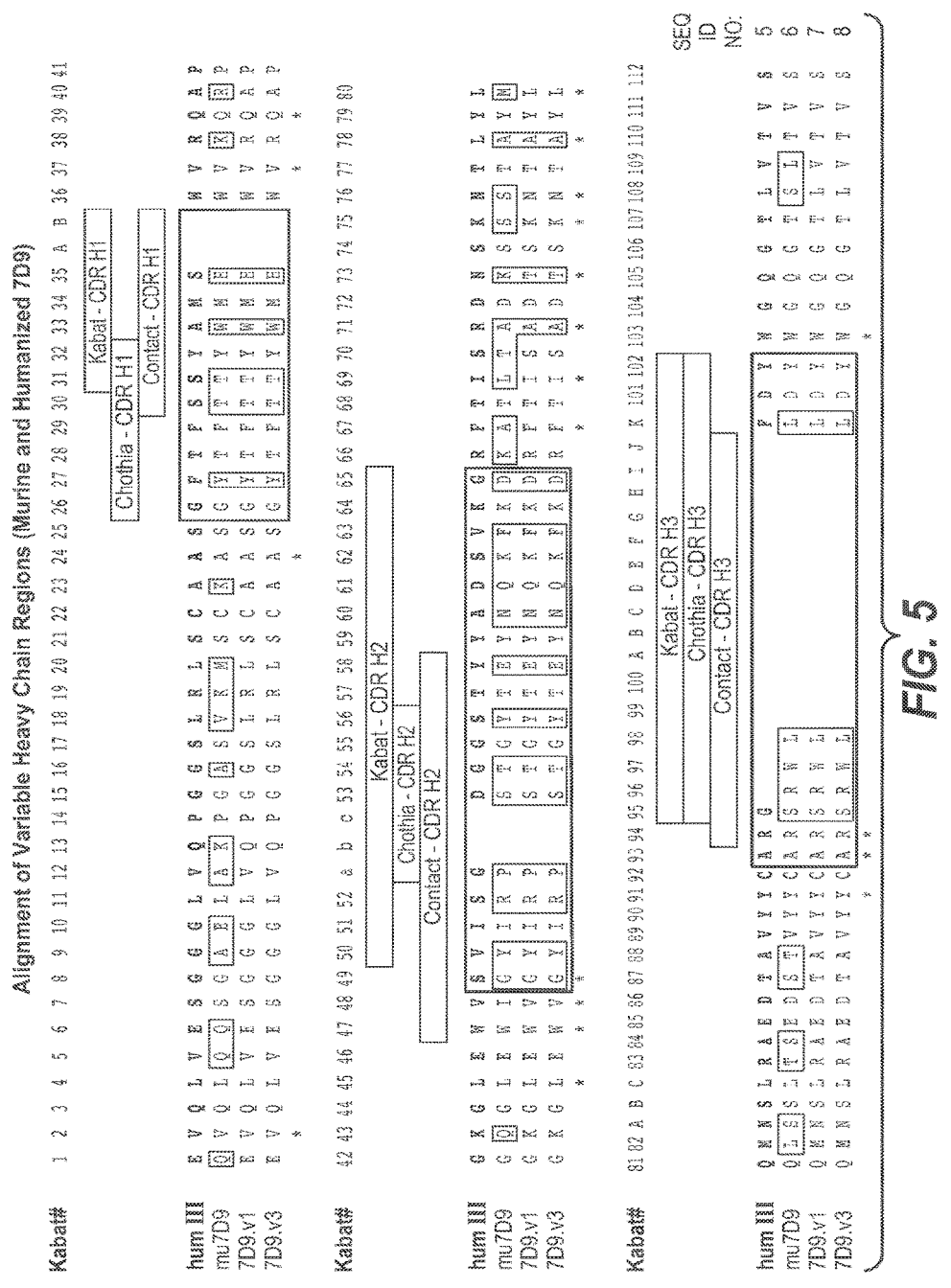

Total RNA was extracted from hybridoma cells producing murine 7D9 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The 7D9 VL and VH amino acid sequences are shown in FIGS. 4 and 5, respectively.

b) Direct Hypervariable Region Grafts onto the Acceptor Human Consensus Framework Variants constructed during the humanization of 7D9 were assessed in the form of an IgG. The VL and VH domains from murine 7D9 were aligned with the human VL kappa I ($VL_{KI}$) and human VH subgroup III ($VH_{III}$) consensus sequences. Hypervariable regions from the murine 7D9 (mu7D9) antibody were engineered into $VL_{KI}$ and $VH_{ATA}$ acceptor frameworks to generate 7D9.v1. The acceptor VH framework $VH_{ATA}$ differs from $VH_{III}$ at 3 positions: R71A, N73T, and L78A (Carter et al., Proc. Natl. Acad. Sci. USA 89:4285 (1992)). From the mu7D9 VL domain, positions 24-34 (L1), 50-56 (L2) and 89-97 (L3) were grafted into $VL_{KI}$. From the mu7D9 VH domain, positions 26-35 (H1), 49-65 (H2) and 95-102 (H3) were grafted into $VH_{ATA}$ (FIGS. 1 and 2). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. J. Mol. Biol. 262: 732-745 (1996)).

The direct-graft, 7D9.v1, was generated by Kunkel mutagenesis using a separate oligonucleotide for each hypervariable region. Three phosphorylated oligonucleotides for either heavy chain or light chain were added to 571 ng Kunkel template in 50 mM Tris pH 7.5, 10 mM MgCl$_2$ in a final volume of 40 µl. The mixture was annealed at 90° C. for 2 min, 50° C. for 5 min and then cooled on ice. 10 µl annealed template was then filled in by adding 0.5 µl 100 mM ATP, 0.5 µl 25 mM dNTPs (25 mM each of dATP, dCTP, dGTP and dTTP), 1 µl 100 mM DTT, 1 µl 10×TM buffer (0.5 M Tris pH 7.5, 0.1 M MgCl$_2$), 80 U T4 ligase, and 4 U T7 polymerase in a total volume of 13.6 µl for 2 hours at room temperature. 10 µl of the filled in and ligated product was then transformed into XL1-blue cells (Stratagene). Correct clones were identified by DNA sequencing and expressed as an IgG.

c) Assessment of Variants

7D9 variants were expressed as IgG by CHO transient transfection. IgG was purified with protein G affinity chromatography. The affinity of each 7D9 IgG variant for human mesothelin was determined by surface plasmon resonance using a BIACORE™-2000. BIACORE™ research grade CM5 chips were immobilized with approximately 110 RU of *E. coli* derived recombinant human mesothelin using the amine coupling kit from BIACORE™. Serial 2-fold dilutions of each 7D9 variant (0.488 to 1000 nM in PBS containing 0.05% TWEEN™ 20) were injected at a flow rate of 30 µl/min. Each sample was analyzed with 5-minute association and 3.5-minute dissociation. After each injection the chip was regenerated using 10 mM Glycine pH 1.7. Binding response was corrected by subtracting the RU from a flow cell with an irrelevant IgG immobilized at similar density. A 1:1 Languir model of simultaneous fitting of $k_{on}$ and $k_{off}$ was used for kinetics analysis.

d) Results

The human acceptor framework used for humanization of 7D9 is based on the human VL kappa I consensus ($VL_{KI}$) and the acceptor VH framework $VH_{ATA}$, which differs from the human VH subgroup III consensus ($VH_{III}$) at 3 positions: R71A, N73T, and L78A (Carter et al., *Proc. Natl. Acad. Sci. USA* 89:4285 (1992)). The VL and VH domains of murine 7D9 were aligned with the human $VL_{KI}$ and $VH_{III}$ domains; hypervariable regions were identified and grafted into the human acceptor framework to generate 7D9.v1 (FIGS. 4 and 5). As an IgG, the affinity of 7D9.v1 is decreased ~2-fold relative to mu7D9 (formatted as a chimeric 7D9) as assessed by Biacore (FIG. 6).

To improve the binding affinity of 7D9.v1, positions 36 and 87 in the light chain and positions of 48, 67, 69, 71, 73, 75, 76, 78 and 80 in the heavy chain were changed to residues found at these positions in mu7D9. Combinations of these altered light and heavy chains with chains from 7D9.v1 were transfected into CHO, expressed as IgG and purified, and assessed for binding to human mesothelin by Biacore (FIG. 6).

Variants 7D9.v2 and 7D9.v3, both of which contain the altered light chain, had an affinity comparable to chimeric 7D9. Variant 7D9.v3 differs from 7D9.v1 at 2 positions in the light chain. Neither change alone was sufficient to improve binding comparable to that of mu7D9 (FIG. 6).

Summary of Changes for Humanized 7D9.v3:

The 6 murine 7D9 CDRs (defined as positions 24-34 (L1), 50-56 (L2) and 89-97 (L3), 26-35 (H1), 49-65 (H2) and 93-102 (H3)) were grafted into the human consensus $VL_{KI}$ and $VH_{ATA}$ acceptor domains. Two additional framework residues, 36 and 87 of the light chain were changed back to murine residues leading to 7D9.v3 with comparable affinity to mu7D9.

2. Humanization of 22A10 a) Cloning of Murine 22A10 Variable Domains

Figure 7:
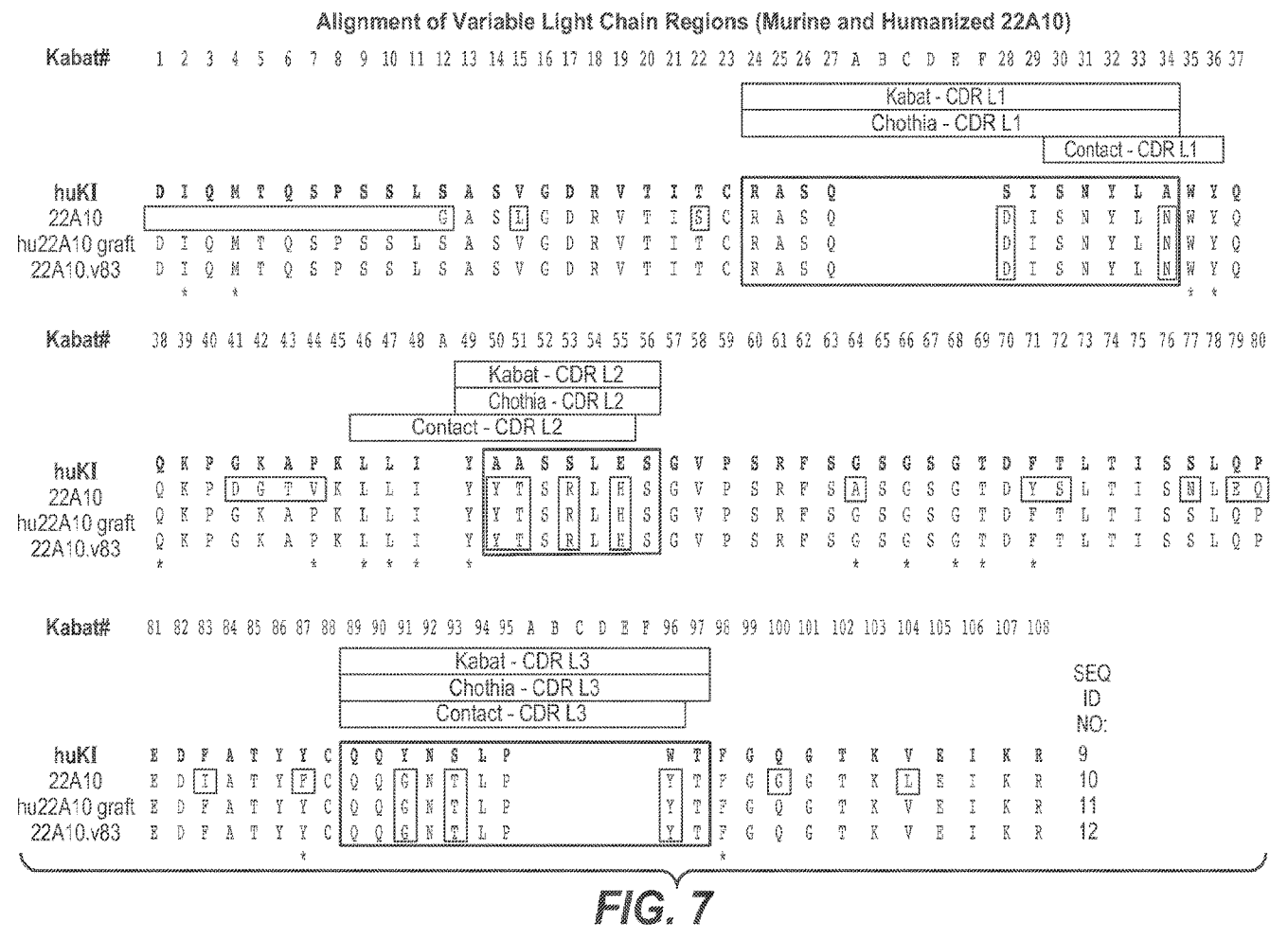
Figure 8:
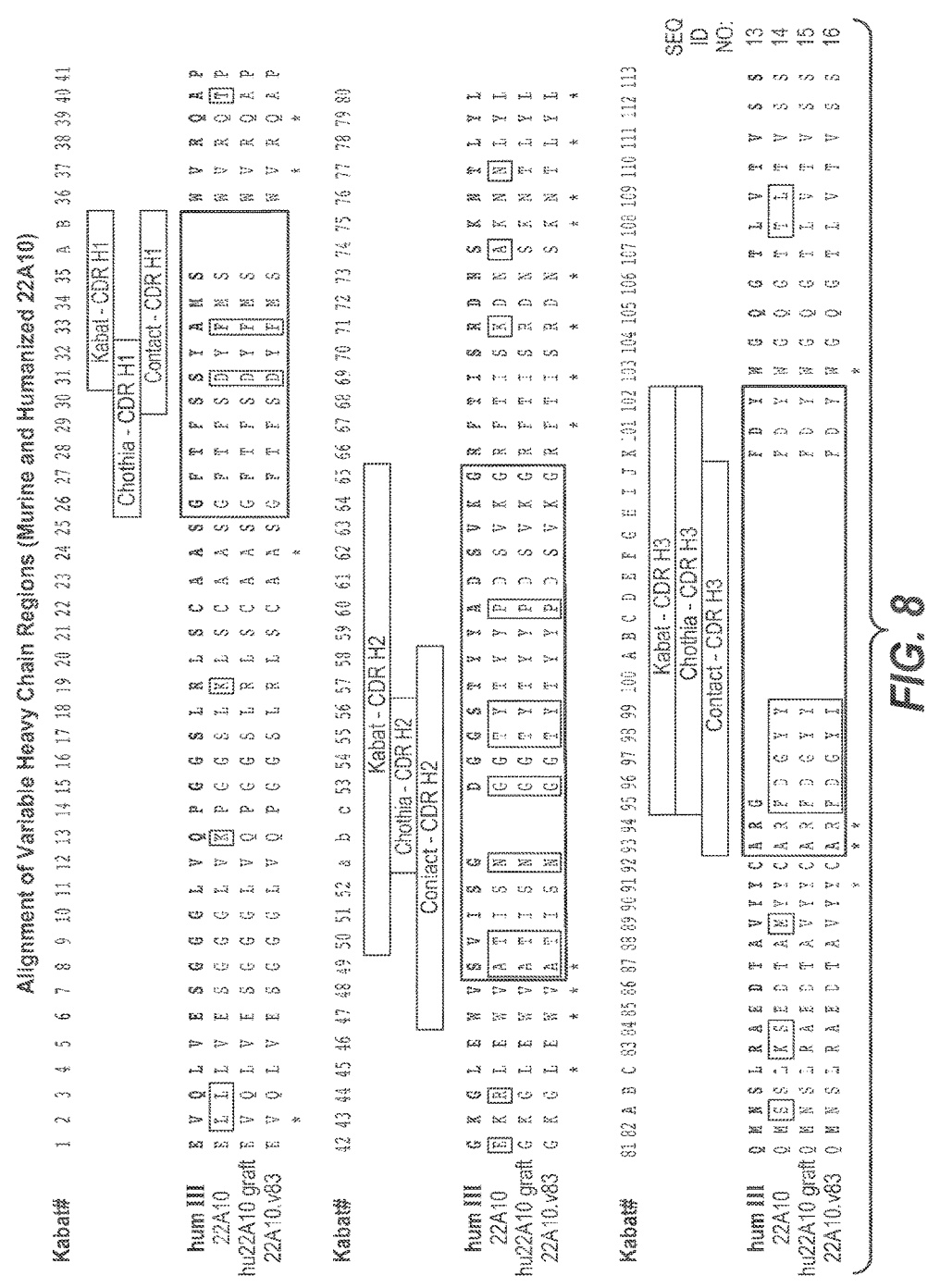

Total RNA was extracted from hybridoma cells producing murine 22A10 using standard methods. The variable light (VL) and variable heavy (VH) domains were amplified using RT-PCR with degenerate primers to the heavy chain (HC) and light chain (LC). The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The 22A10 VL and VH amino acid sequences are shown in FIGS. 7 and 8, respectively.

b) Direct Hypervariable Region Grafts onto the Acceptor Human Consensus Framework Variants constructed during the humanization of 22A10 were assessed in the form of an IgG or displayed monovalently as Fab on phage. The phagemid used for this work was a monovalent Fab-g3 display vector, which consists of two open reading frames under control of a single phoA promoter. The first open reading frame consists of the stII signal sequence fused to the VL and CH1 domains of the acceptor light chain, and the second consists of the stII signal sequence fused to the VH and CH1 domains of the acceptor heavy chain followed by the minor phage coat protein P3.

The VL and VH domains from murine 22A10 were aligned with the human VL kappa I ($VL_{KI}$) and human VH subgroup III ($VH_{III}$) consensus sequences. Hypervariable regions from the murine 22A10 (mu22A10) antibody were engineered into $VL_{KI}$ and $VH_{III}$ acceptor frameworks to generate the 22A10 graft. From the mu22A10 VL domain, positions 24-34 (L1), 50-56 (L2) and 89-97 (L3) were grafted into $VL_{KI}$. From the mu22A10 VH domain, positions 26-35 (H1), 49-65 (H2) and 95-102 (H3) were grafted into $VH_{III}$ (FIGS. 7 and 8). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. *J. Mol. Biol.* 262: 732-745 (1996)).

The 22A10 graft was generated by Kunkel mutagenesis using a separate oligonucleotide for each hypervariable region. Three phosphorylated oligonucleotides for either heavy chain or light chain were added to 571 ng Kunkel template in 50 mM Tris pH 7.5, 10 mM MgCl2 in a final volume of 40 µl. The mixture was annealed at 90° C. for 2 min, 50° C. for 5 min and then cooled on ice. 10 µl annealed template was then filled in by adding 0.5 µl 100 mM ATP, 0.5 µl 25 mM dNTPs (25 mM each of dATP, dCTP, dGTP and dTTP), 1 µl 100 mM DTT, 1 µl 10×TM buffer (0.5 M Tris pH 7.5, 0.1 M MgCl2), 80 U T4 ligase, and 4 U T7 polymerase in a total volume of 13.6 µl for 2 hours at room temperature. 10 µl of the filled in and ligated product was then transformed into XL1-blue cells (Stratagene). Correct clones were identified by DNA sequencing and expressed as an IgG.

c) Soft Randomization of the Hypervariable Regions

The 22A10 graft was affinity matured using a soft randomization strategy. Sequence diversity was introduced separately into each hypervariable region such that a bias towards the murine hypervariable region sequence was maintained using a poisoned oligonucleotide synthesis strategy (Gallop et al., *J Med Chem* 37:1233-51 (1994)). For each diversified position, the codon encoding the wild-type amino acid is poisoned with a 70-10-10-10 mixture of nucleotides resulting in an average 50 percent mutation rate at each position. Sequence diversity was introduced in the hypervariable regions of the 22A10-graft using Kunkel mutagenesis to generate six soft randomized phage libraries that were sorted separately. Six libraries were made each consisting of a single soft randomized hypervariable region.

d) Generation of Phage Libraries

Oligonucleotides designed to introduce diversity into each hypervariable region were phosphorylated separately in 20 µl reactions containing 660 ng of oligonucleotide, 50 mM Tris pH 7.5, 10 mM $MgCl_2$, 1 mM ATP, 20 mM DTT, and 5 U polynucleotide kinase for 1 h at 37° C.

For each library, 2 µl of phosphorylated oligonucleotide was added to 300 ng Kunkel template in 50 mM Tris pH 7.5, 10 mM $MgCl_2$ in a final volume of 10 µl. The mixture was annealed at 90° C. for 2 min, 50° C. for 5 min and then cooled on ice. The annealed template was then filled in by adding 0.5 µl 10 mM ATP, 0.5 µl 10 mM dNTPs (10 mM each of dATP, dCTP, dGTP and dTTP), 1 µl 100 mM DTT, 1 µl 10×TM buffer (0.5 M Tris pH 7.5, 0.1 M $MgCl_2$), 80 U T4 ligase, and 4 U T7 polymerase in a total volume of 20 µl for 2 hours at room temperature. These filled-in and ligated products were then each transformed into XL1-blue cells, grown in 0.5 ml of 2YT containing 5 µg/ml of tetracycline and M13/KO7 helper phage (MOI 10) for 2 hr at 37° C. and then pooled and transferred to 500 ml 2YT containing 50 µg/ml carbenacillin and grown 16 h at 37° C.

e) Phage Selections

For solid phase phage selections, 293-derived human or cynomolgus monkey mesothelin was immobilized in 50 mM sodium bicarbonate pH 9.6 on MAXISORP® microtiter plates (Nunc, Rochester, N.Y.) overnight at 4° C. Plates were blocked for at least 1 hour using Casein Blocker (Pierce, Rockford, Ill.).

Phage were harvested from the culture supernatant and suspended in PBS containing 5% powdered milk and 0.05% TWEEN™ 20 (PBSBT). Following addition of the phage library and a 1 hour incubation, microtiter wells were washed extensively with PBS containing 0.05% TWEEN™ 20 (PBST) and bound phage were eluted by incubating the wells with 20 mM HCl, 500 mM KCl for 30 minutes. Eluted phage were neutralized with 1 M Tris, pH 8 and amplified using XL1-Blue cells and M13/KO7 helper phage and grown overnight at 37° C. in 2YT, 50 µg/ml carbencillin. The titers of phage eluted from a target-containing well were compared to titers of phage recovered from a non-target-containing well to assess enrichment.

For solution phase phage selections, biotinylated 293-derived human or biotinylated cynomolgus monkey mesothelin was added to phage suspended in PBS containing 5% powdered milk and 0.05% TWEEN™ 20 (PBSBT). Following incubation, phage bound to biotinylated mesothelin were captured on a microtiter plate coated with streptavidin for 5 minutes. Microtiter wells were washed extensively with PBS containing 0.05% TWEEN™ 20 (PBST) and bound phage were eluted by incubating the wells with 20 mM HCl, 500 mM KCl for 30 minutes. Eluted phage were neutralized with 1 M Tris, pH 8 and amplified using XL1-Blue cells and M13/KO7 helper phage and grown overnight at 37° C. in 2YT, 50 µg/ml carbencillin. The titers of phage eluted from a target-containing well were compared to titers of phage recovered from a non-target-containing well to assess enrichment.

For the solution phase phage selections, the selection stringency was gradually increased both by capturing phage that bound to decreasing concentrations of biotinylated mesothelin in solution followed by capture on neutravidin for 10 minutes (on rate selection) and by increasing the washing time and temperature to allow weak binding phage to be washed away (off rate selection) (Fuh et al., *J. Mol. Biol.* 340:1073-1093 (2004)).

J) IgG Production

For screening purposes, IgG variants were initially produced in 293 cells. Vectors coding for VL and VH (25 µg) were transfected into 293 cells using the FUGENE system (Roche, Basel, Switzerland). 500 µl of FuGene was mixed with 4.5 ml of DMEM media containing no FBS and incubated at room temperature for 5 minutes. Each chain (25 µg) was added to this mixture and incubated at room temperature for 20 minutes and then transferred to five T-150 flasks for transfection overnight at 37° C. in 5% $CO_2$. The following day the media containing the transfection mixture was removed and replaced with 23 ml PS04 media with 0.1 ml/L trace elements (A0934) and 10 mg/L insulin (A0940). Cells were incubated for an additional 5 days after which the media was harvested at 1000 rpm for 5 minutes and sterile filtered using a 0.22 µm low protein-binding filter. Samples could be stored at 4° C. after addition of 2.5 ml 0.1% PMSF for every 125 ml of media. IgG was purified with protein G affinity chromatography.

g) Affinity Determinations

The affinity of 22A10 IgG variants for human or cynomolgus monkey mesothelin was determined by surface plasmon resonance using a BIACORE™-2000. BIACORE™ research grade CM5 chips were immobilized with approximately 110 RU of *E. coli* derived recombinant human or cynomolgus monkey mesothelin using the amine coupling kit from BIACORE™. Serial 2-fold dilutions of each 22A10 variant (0.488 to 1000 nM in PBS containing 0.05% TWEEN™ 20) were injected at a flow rate of 30 µl/min. Each sample was analyzed with 5-minute association and 3.5-minute dissociation. After each injection the chip was regenerated using 10 mM Glycine pH 1.7. Binding response was corrected by subtracting the RU from a flow cell with an irrelevant IgG immobilized at similar density. A 1:1 Languir model of simultaneous fitting of $k_{on}$ and $k_{off}$ was used for kinetics analysis.

h) Results

The human acceptor framework used for humanization of 22A10 was based on the consensus human kappa I VL domain and the consensus human subgroup III VH domain. The VL and VH domains of mu22A10 were aligned with the human kappa I and subgroup III domains; each complementarity determining region (CDR) was identified and grafted into the human acceptor framework to generate a CDR graft that could be expressed as an IgG or displayed as an Fab on phage (FIGS. 7 and 8).

Six soft randomization libraries were generated in which diversity was introduced separately into each CDR of the 22A10 CDR graft. Libraries were panned against human and cynomolgus monkey mesothelin (derived from 293 cells, with the aim of improving binding to glysosylated forms of cynomolgus monkey or human mesothelin) using both solid phase and solution sorting strategies. The solution sorting method allows high affinity clones to be selected through manipulation of the biotinylated target concentration and phage capture time while the addition of unlabeled target can be used to eliminate clones with faster off rates (Fuh et al. *J. Mol. Biol.* 340:1073-1093 (2004)). Clones from the last round for each library were picked for DNA sequence analysis and revealed sequence changes targeted at each CDR except CDR-L2 and CDR-H2, suggesting many possible variations to improve antigen binding. Several clones selected on either human or cynomolgus monkey mesothelin had changes in CDR-H3, the most abundant having a tyrosine to isoleucine change at position 99. This variant, along with several others, was expressed as an IgG and characterized for binding to mesothelin by Biacore and by Scatchard analysis (FIG. 9A). Several clones exceeded the affinity of the graft of 22A10.

Humanized 22A10 variants were used to immunoprecipitate mesothelin from a cell line stably expressing mesothelin. BJAB cells stably expressing gD-tagged mesothelin of different species were immunoprecipitated with the humanized 22A10 variants, as shown in FIG. 9B (Gr, graft; vi (1), v17 (17) and v83 (83)) or h7D9.v3, h5B6 anti-gD or hIgG negative control for comparison. Immunoprecipitates were washed and Western blotted with murine anti-gD antibodies to detect gD-mesothelin. h2210.v83 was the best of the h22A10 variants in its ability to immunoprecipitate all three species of mesothelin (cynomolgus monkey, upper; human, middle; and rat, lower blot). The right-most lane shows 20% input lysate (without immunoprecipitation) for comparison of total expression levels. Molecular weight markers (kDa) are indicated on the left.

Summary of Changes for Humanized 22A10.v83:

Starting from a graft of the six murine 22A10 CDRs (defined as positions 24-34 (L1), 50-56 (L2), 89-97 (L3), 26-35 (H1), 49-65 (H2) and 95-102 (H3)) into the human consensus Kappa I VL and subgroup III VH, CDR soft randomization was used to identified a change in CDR H3 (Y99I) that improved binding to human and cynomologus monkey mesothelin. 22A10.v83 showed high affinity binding, and also showed the ability to recognize more binding sites, relative to the other humanized variants.

Throughout this application, mouse monoclonal antibodies 7D9 and 22A10 are referred to in the alternative as 7D9, m7D9 or mu7D9; and 22A10, m22A10 or mu22A10, respectively. Humanized monoclonal antibodies 7D9.v3 and 22A10.v83 are referred to in the alternative as 7D9.v3, h7D9.v3 or hu7D9.v3; and 22A10.v83, h22A10.v83 or hu22A10.v83, respectively, unless otherwise indicated.

D. Species Cross-Reactivity

Figure 11:
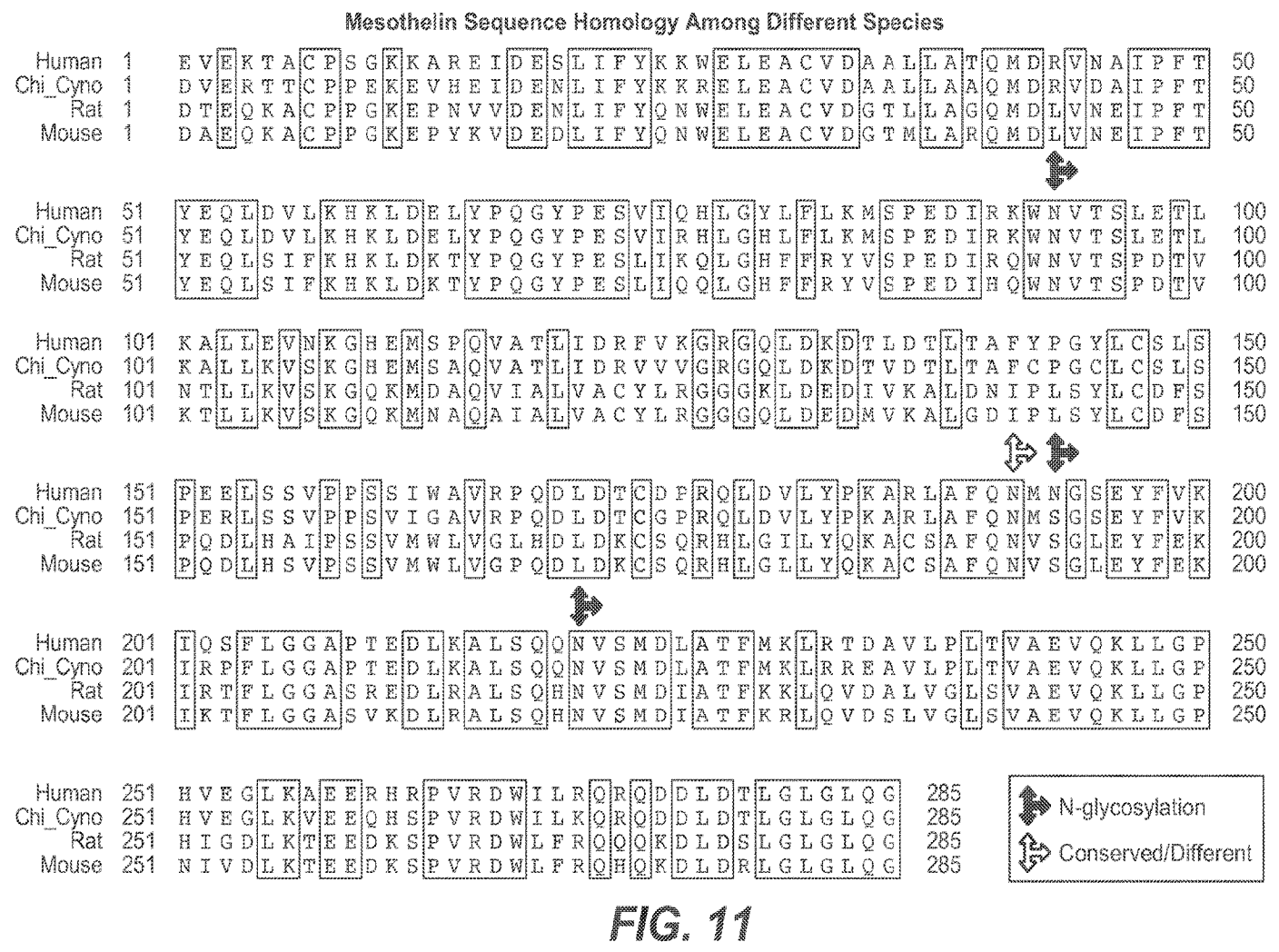
Figures 12, 13:
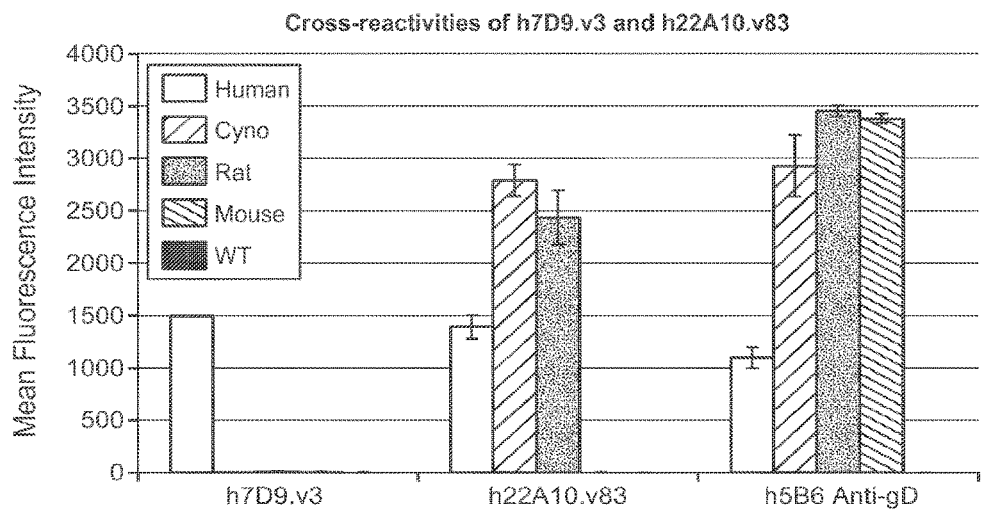
FIG. 12 shows cross-reactivities of h7D9.v3 and h22A10.v83 with mesothelin from different species, as described in Example D.
FIG. 13 shows the affinities of humanized anti-mesothelin antibodies as determined by Scatchard analysis of transfected cell lines stably expressing mesothelin and cell lines expressing endogenous mesothelin, as described in Example E.

Monoclonal antibodies were tested to determine if they cross-react with mesothelin from species other than human. FIG. 11 shows the sequence homology between human (SEQ ID NO:43), cynomolgus monkey (SEQ ID NO:46), rat (SEQ ID NO:47) and mouse (SEQ ID NO:48) mesothelin. Shaded residues are identical between at least two species. Unshaded residues differ between at least two of the four species. FIG. 12 shows the results of FACS analysis of 293 cells stably transfected with gD epitope-tagged mesothelin (human, cyno, rat or mouse mesothelin); stained with 10 µg/ml h7D9.v3, h22A10.v83 or anti-gD h5B6; and detected with ALEXA FLUOR® 647 anti-human antibody. Untransfected 293 cells do not normally express mesothelin ("WT"). h7D9.v3 is specific for human mesothelin, while h22A10.v83 binds to human, cyno and rat mesothelin, but not mouse mesothelin. Anti-gD staining verified that mouse mesothelin was indeed expressed.

E. Antibody Affinities

To determine the relative binding affinities of h7D9.v3 and h22A10.v83, Scatchard analysis was performed following standard procedures (Holmes et al., Science 256:1205-1210 (1992)), briefly by incubating detached cells with [$I^{125}$] labeled h7D9.v3 or h22A10.v83 for 2 hours at room temperature in the presence of increasing concentrations of unlabeled antibody, washing and quantitating the cell-bound radioactivity by scintillation counting. The data was analyzed with non-linear regression curve fitting in the New Ligand program (Genentech, Inc., South San Francisco, Calif.) to estimate Kd values (Munson et al., *Anal. Biochem.,* 107 220-239 (1980)).

As shown in FIG. 13, h7D9.v3 bound to gD-tagged human mesothelin expressed on stably transfected 293, BJAB and HT1080 cell lines (all of which do not express endogenous mesothelin) with affinities of 0.2, 0.25 and 0.97 nM, respectively. These Kd values encompass the range seen for endogenous mesothelin in four pancreatic and two ovarian cell lines (0.41-1 nM). h22A10.v83 affinities for human mesothelin expressed on the same stable cell lines were 2.7, 1.8 and 6.2 nM respectively, in accordance with its affinity for endogenous human mesothelin (~9-10 nM). h22A10.v83 bound to rat mesothelin expressed on stably transfected 293 cells and BJAB cells with affinities of 7.3 nM and 2.7 nM, respectively, which is in line with the Kd of 6.2 nM observed for endogenous rat mesothelin on a normal pleural cell line, 4/4-RM4 (Aronson et al., *In Vitro* 17: 61-70 (1981)).

F. Epitope Groups

In order to determine if 7D9 and 22A10 share the same epitope as other anti-mesothelin antibodies listed in FIG. 3, epitope mapping of the monoclonal antibodies was performed by a standard cross-blocking ELISA. Ninety-six well NUNC-IMMUNO™ sorp plates (Nalge Nunc, USA) were coated overnight at 4° C. with 100 µL of 1 µg/mL human mesothelin extracellular domain in coating buffer (50 mM sodium carbonate, pH 9.5). All the following steps were performed at room temperature. After washing three times in 200 µL washing buffer (PBS containing 0.05% TWEEN™ 20, pH 7.4), plates were blocked with ELISA buffer (PBS containing 0.5% bovine serum albumin (BSA) and 0.05% TWEEN™ 20, pH 7.4) for 60 minutes. Murine monoclonal antibodies 7D9 or 22A10 were then added at 20 µg/mL in ELISA buffer for 2 hours (100 µL per well). Without washing, biotinylated versions of all the test anti-mesothelin antibodies were also added (100 µL of 2 µg/mL) to a final concentration of 1 µg/mL for 30 minutes. After washing three times in 200 µL washing buffer, any biotinylated antibody binding was detected by adding streptavidin-horseradish peroxidase (HRP) (Zymed; Carlsbad, Calif.) at a dilution of 1:5000 for 30 minutes. After three washes as above, 100 µL chromogenic 3,3',5,5'-tetramethylbenzidine (TMB) substrate was added (BioFX Laboratories; Owings Mills, Md.) for 5 minutes. The chromogenic reaction was terminated by addition of 100 µL stop reagent (BioFX Laboratories), and the absorbance was read at 620 nm on an Ultramicroplate Reader (Biotek Instruments; Winooski, Vt.). The maximal extent of possible binding of each of the biotinylated antibodies was determined in parallel by incubating them with mesothelin in the absence of the non-biotinylated antibodies 7D9 and 22A10.

Figure 14:
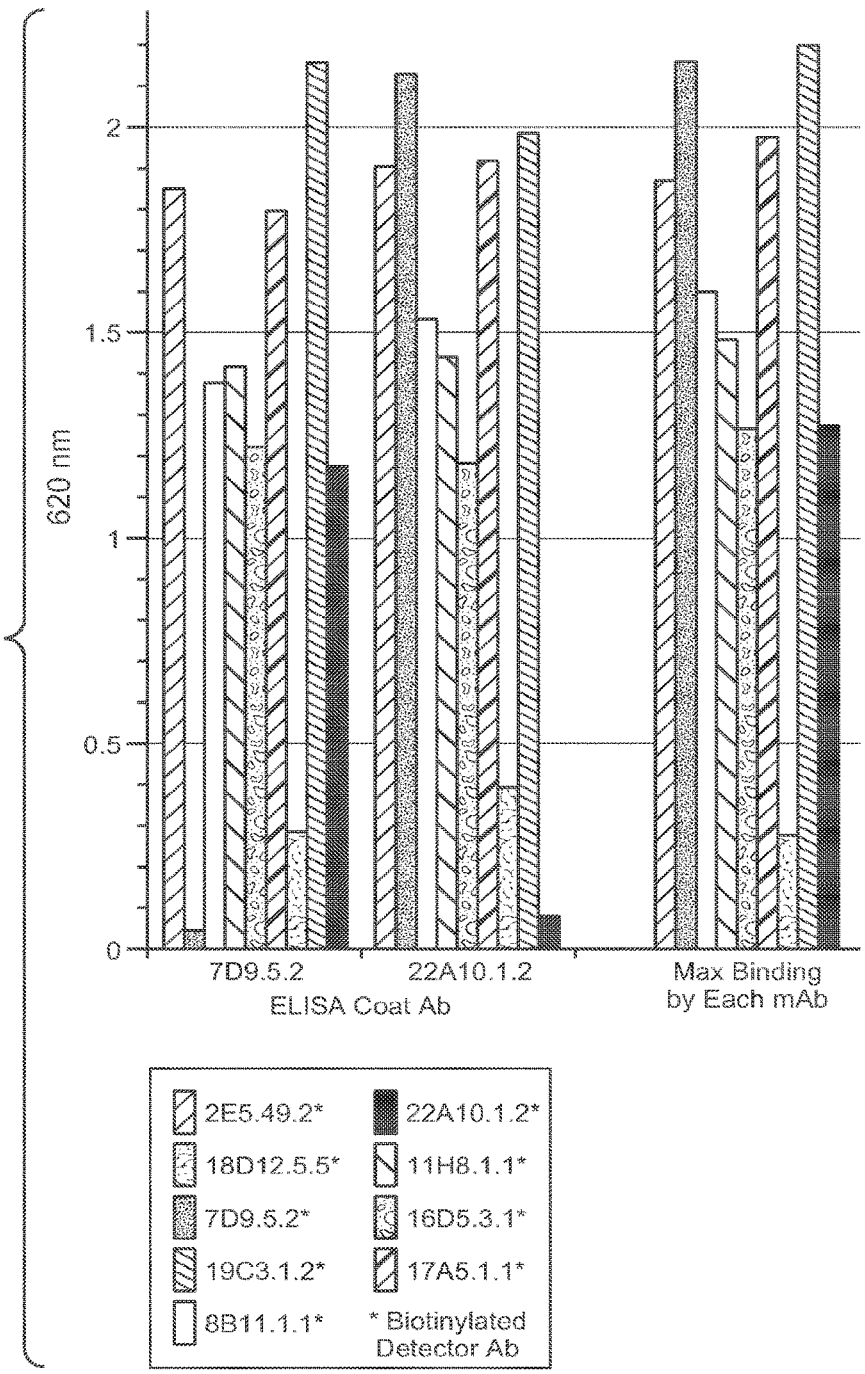
FIG. 14 shows the results of competition assays between antibody 7D9 or 22A10 and the other monoclonal antibodies listed in FIG. 3, as described in Example F.

The results are shown in FIG. 14. A signal by any of the nine biotinylated anti-mesothelin antibodies (*) indicates lack of competition for the first antibody (the maximal binding by each biotinylated antibody in the absence of the first antibody for comparison is also shown in the right group). 7D9 (referred to as 7D9.5.2 in FIG. 14) is the only antibody that cannot bind when 7D9 is present (i.e., it competes with itself, second bar from left), whereas 22A10 (referred to as 22A10.1.2 in FIG. 14) binds normally (black bar in left group). Conversely, when 22A10 is pre-bound, 22A10 cannot bind (last bar of middle group), whereas 7D9 and the other antibodies can. Thus not only do 7D9 and 22A10 not compete with each other, but also each binds an epitope distinct from the other seven antibodies. 7D9 was competed by itself, but not by any other antibody (compare each bar to the maximal signal for each antibody binding to mesothelin on the plate in the absence of ELISA coat antibody 7D9 or 22A10). Similarly, 22A10 only competed itself and not other antibodies, including 7D9. Thus, 7D9 and 22A10 have distinct epitopes relative to each other and to the other isolated monoclonal antibodies.

G. Epitope Mapping Using Human:Mouse and Cyno: Human Mesothelin Chimerae and Mutational Analysis Tryptic peptide mapping experiments were performed in which h7D9.v3 was bound to immobilized human mesothelin, which was then incubated with trypsin, and the remaining antibody-protected peptides were eluted and identified by mass spectrometry. Those experiments implicated amino acids 133-183 of SEQ ID NO:43 as the h7D9.v3 binding site. To confirm this region, we took advantage of 7D9 reacting with human (construct #387 shown in FIG. 15), but not mouse (construct #385) or cyno (construct #383) mesothelin to generate chimerae, which we predicted should fold better than truncation mutants. We constructed human: mouse mesothelin chimerae (#398 and #399) using a silent MfeI site (encoding QL) at amino acid 131 and a silent BglII site (encoding DL) at amino acid 213 for introducing human sequences into the mouse construct. Additionally, a cyno construct (#400) was created in which amino acids 131-178 were replaced by those of human mesothelin via MfeI sites. Each construct had an N-terminal gD tag (not shown) to verify expression.

Figure 15:
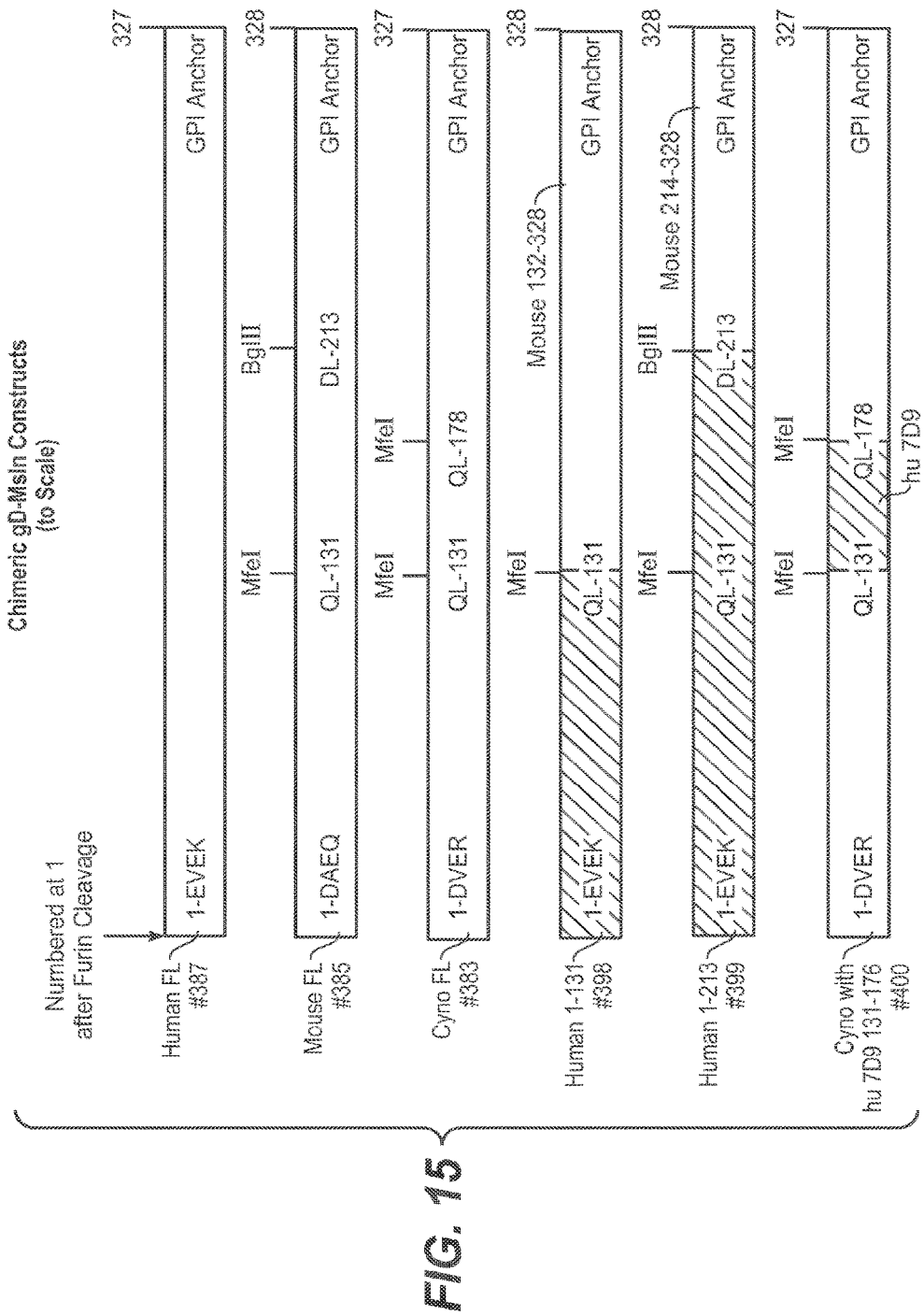
FIG. 15 shows chimeric mesothelin constructs used for epitope mapping (drawn to scale), as described in Example G.
Figure 16:
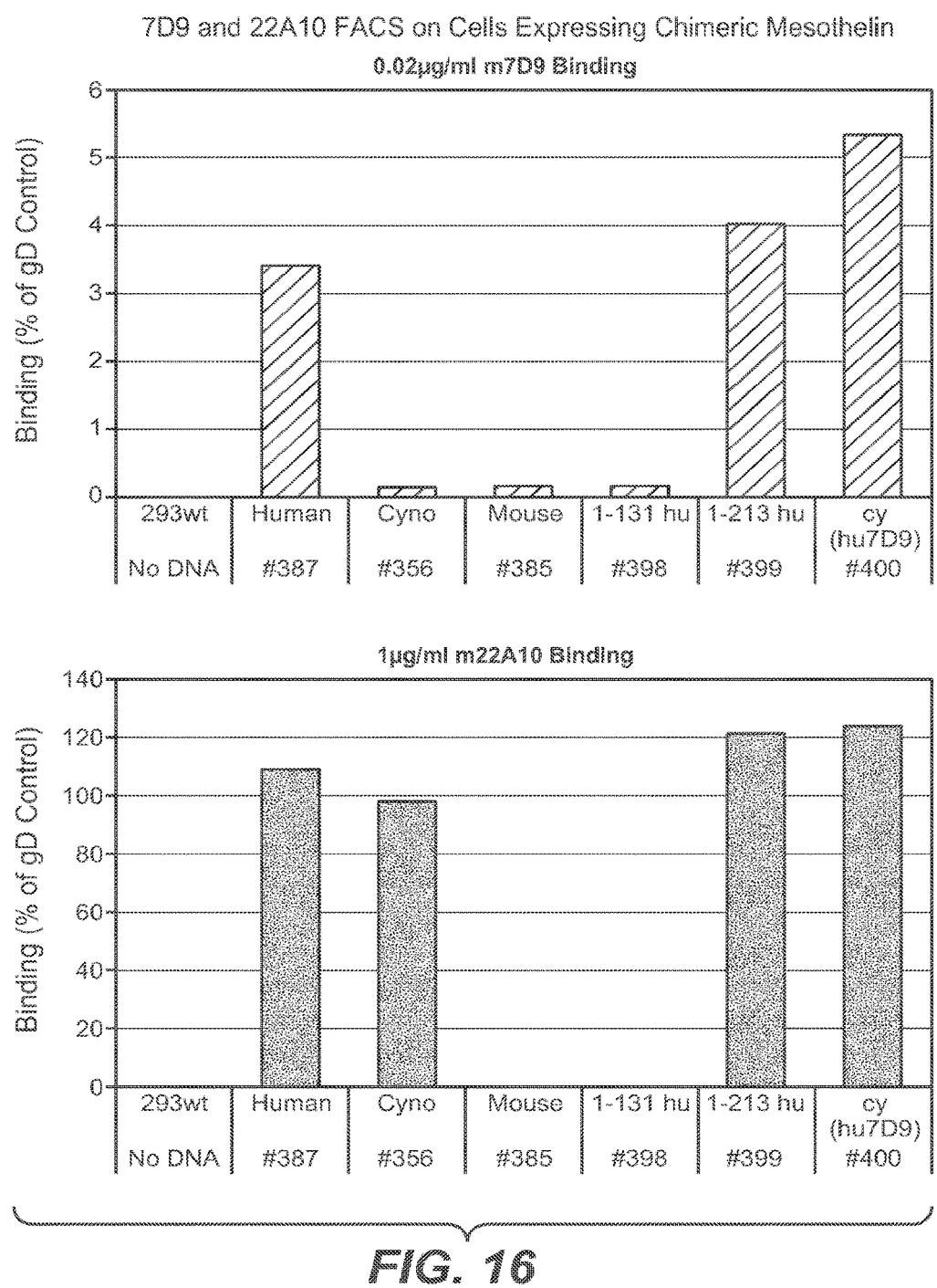
FIG. 16 shows the results of FACS to assess binding of 7D9 and 22A10 to cells expressing chimeric mesothelin, as described in Example G.

The gD-tagged, GPI anchored mesothelin constructs shown in FIG. 15 were transiently expressed in 293 cells and stained with 0.02 µg/ml murine 7D9, 1 µg/ml murine 22A10, or 1 µg/ml anti-gD tag (to normalize for differential expression levels). After detection with ALEXA FLUOR® 488 anti-mouse antibody, samples were washed and analyzed by FACS, and the fluorescence intensity data were normalized to the anti-gD signal after subtraction of any background staining on wild type 293 negative control cells. As shown in FIG. 16, 7D9 binds to the human:mouse chimera #399 (having human amino acids 1-213), but not to either full length mouse mesothelin #385 or #398 (having human amino acids only from 1-131), indicating that 7D9 binds to an epitope between aa 131 and 213. Its ability to bind the cyno:human chimera #400 (having human amino acids 131-178), but not full length cyno (#383), narrowed the epitope to between amino acids 131 and 178. (Note that the relatively lower % binding seen with 7D9 than 22A10 is due to use of 50× lower antibody concentration for 7D9).

The same chimerae were used to map the rat, cyno and human (but not mouse)-reactive 22A10 epitope. Binding was observed on cells expressing chimera #399, but not #398. Thus, 22A10 binds to an epitope with a critical residue between amino acids 131-213. (FIG. 16.)

Figure 17:
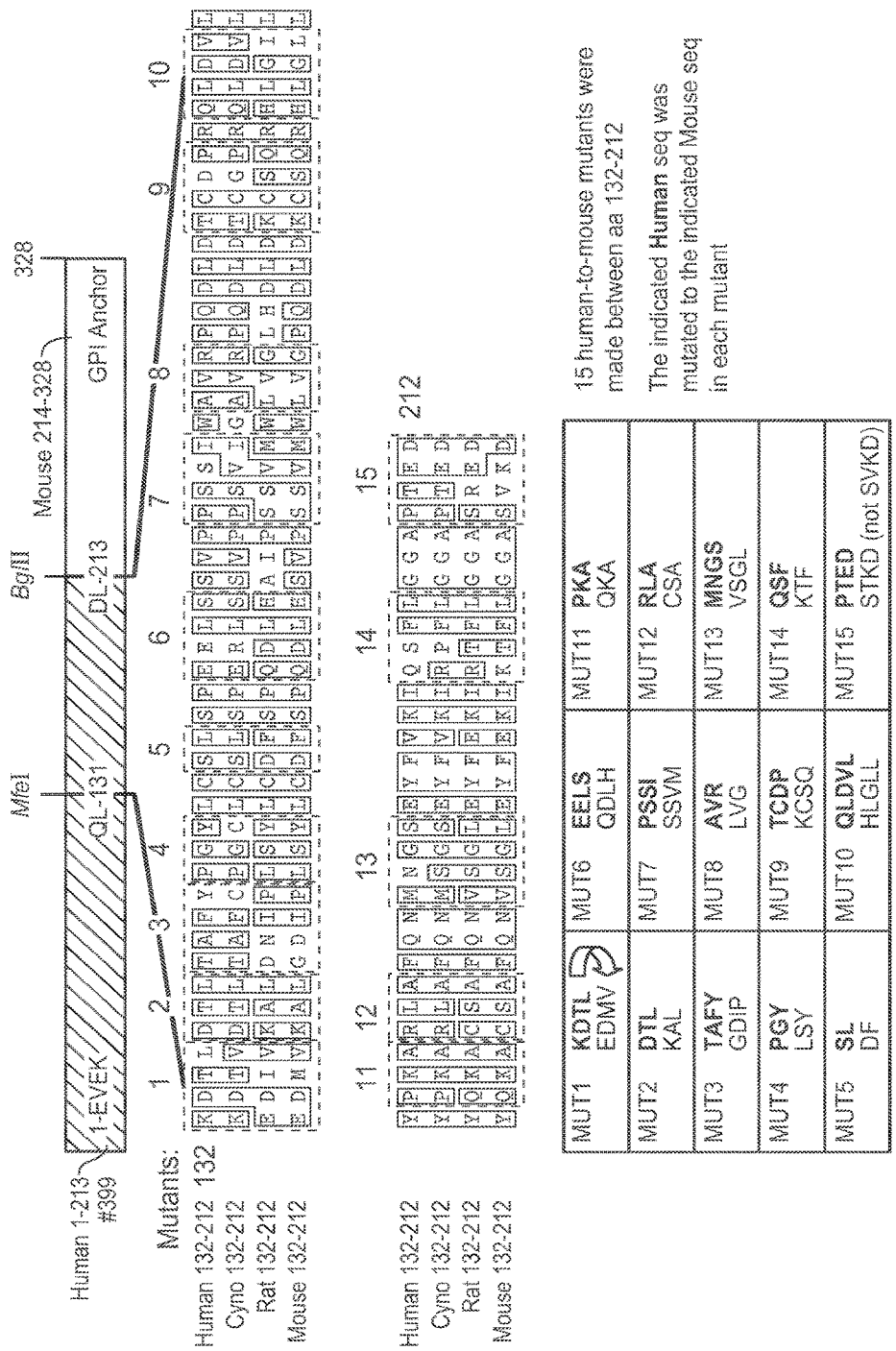
FIG. 17 shows a mutational strategy for identifying the amino acids to which h7D9.v3 and h22A10.v83 bind, as described in Example G.

Because 7D9 and 22A10 do not compete with each other (FIG. 13), they presumably bind to distinct epitopes within amino acids 131-213. To identify those distinct epitopes, 2-4 amino acid stretches of human mesothelin were mutated to the corresponding mouse amino acids in the #399 chimera background. An alignment of amino acids 132-212 among the four species is shown in FIG. 17, with numbered boxes indicating the position of the 15 mutants. For each of the 15 mutants listed in the table at the bottom of FIG. 17, the human sequences (above), which were mutated to mouse sequences (below), are shown. (Note: mutant #11 was not successfully generated.)

Figure 18A:
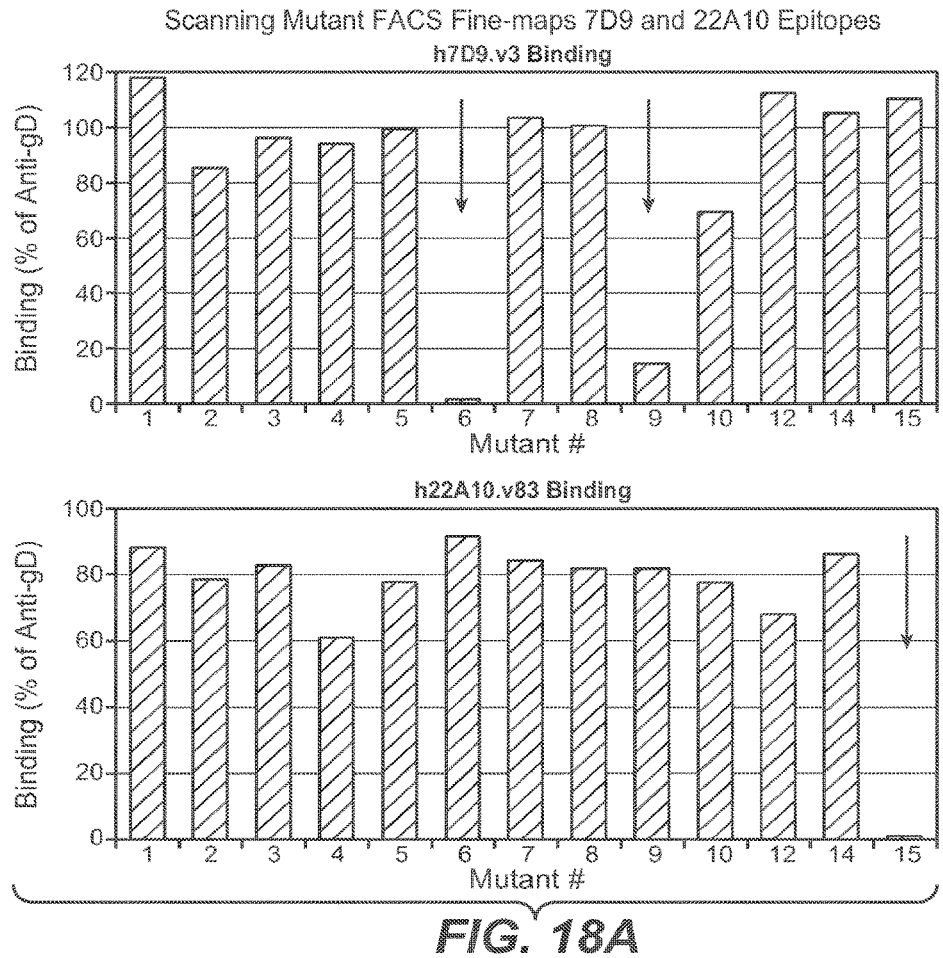
FIG. 18A shows the results of FACS to assess binding of h7D9.v3 and h22A10.v83 to cells expressing human mesothelin mutants, as described in Example G.

All mutants except mutant #11 from FIG. 17 were expressed in 293 cells and subjected to FACS analysis as in FIG. 16, except that 5 µg/ml humanized versions of each antibody (i.e., h7D9.v3, h22A10.v83 and h5B6 anti-gD tag (positive control)) were used, with Alexa488 anti-human antibody used for detection. Results are shown in FIG. 18A, with fluorescence data shown as a percent of the anti-gD signal to normalize for expression levels. (Note: mutant #13 did not express in 293 cells and so is omitted from the dataset). h7D9.v3 bound to all mutants except #6 and #9, while h22A10.v83 bound all mutants except mutant #15 (arrows).

Figure 18B:
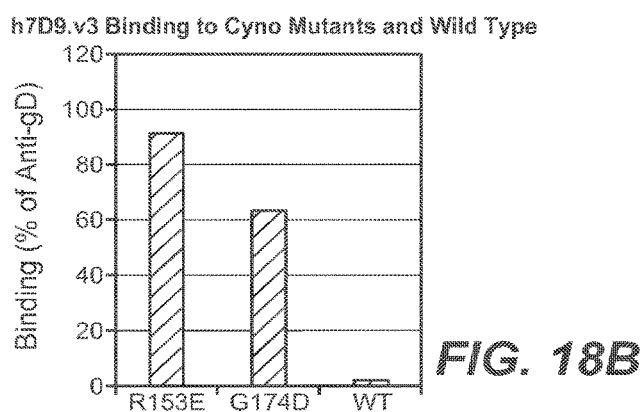
FIG. 18B shows the results of FACS to assess binding of h7D9.v3 to cells expressing cynomolgus monkey mesothelin mutants, as described in Example G.
Figure 19:
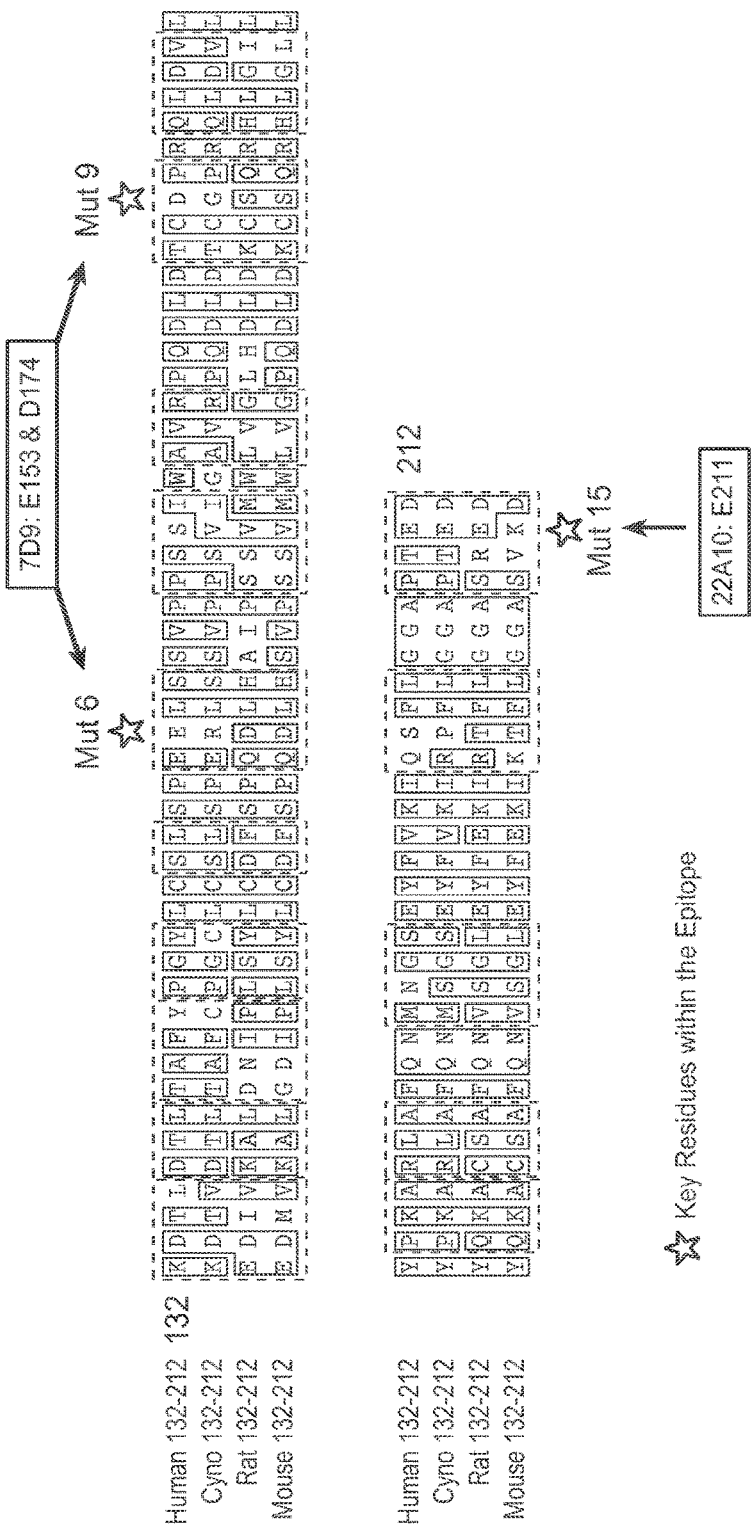
FIG. 19 shows the key amino acid residues within the epitopes to which 7D9/h7D9.v3 and 22A10/h22A10.v83 bind, as described in Example G.
Figure 20:
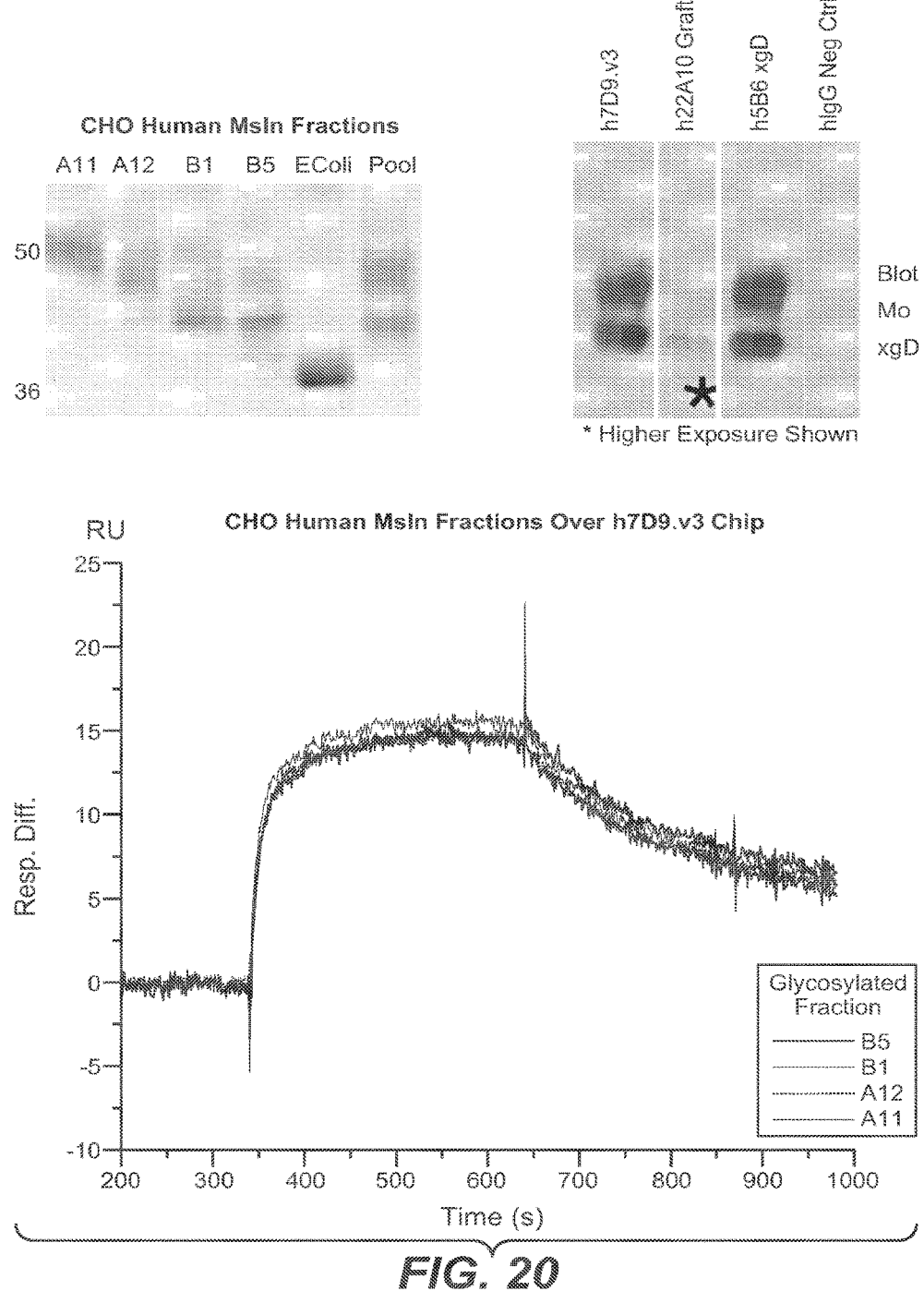
FIG. 20 shows binding of h7D9.v3 to glycosylated mesothelin, as described in Example H.
Figure 21:
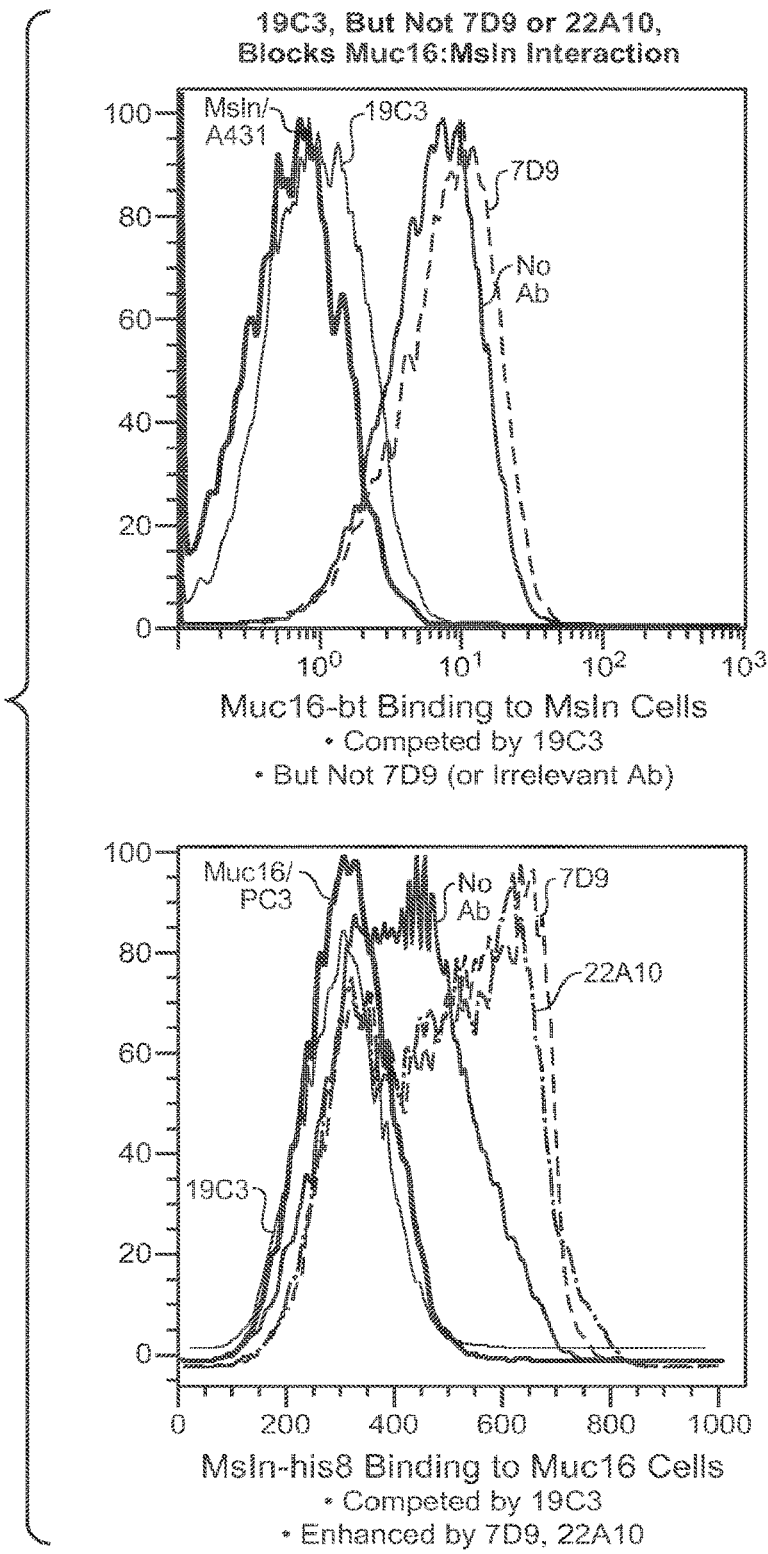
FIG. 21 shows the results of two assays to determine whether antibodies 19C3, 7D9 and 22A10 block binding of mesothelin to MUC16 and vice versa, as described in Example I.

By alignment of the different mesothelin species, key residues in the h7D9.v3 epitope were pinpointed to two single amino acid residues that differ between human and non-cross-reactive cyno sequences: E153 in mutant #6 and D174 in mutant #9. The importance of those residues for antibody binding was confirmed by mutating the equivalent residues in cyno mesothelin to the corresponding human residues (i.e., R153 to E and G174 to D). h7D9.v3, which does not otherwise bind to cyno mesothelin, was able to bind the cyno mesothelin mutants (FIG. 18B). Further studies in which residue E152 of the human mesothelin sequence was mutated to Q resulted in inhibition of h7D9.v3 binding, suggesting that residue E152 also plays a role in antibody binding.

Based on the recently predicted armadillo-like repeat structure of mesothelin (Sathyanarayana et al., *BMC Structural Biology* 9:1 (2009)), the 7D9 antibody likely bridges inner helix 4 and outer helix 5 of mesothelin. Similarly, since h22A10.v83 cross-reacts with rat but not mouse, residue E211 in mutant #15 (in outer helix 6 of Sathyanarayana et al., supra) is likely a critical determinant of its epitope. FIG. 19 depicts the residues bound by h7D9.v3 and h22A10.v83.

H. Binding of h7D9.v3 is not Inhibited by Glycosylation

To determine whether h7D9.v3 binds to glycosylated mesothelin, C-terminally his-tagged human mesothelin was expressed in CHO cells, purified and further separated according to charge on a Mono S column into fractions with high (fraction A11), medium (A12), low (B1) and low-to-none (B5) glycosylation of mesothelin, as shown by Coomassie Blue staining on an SDS-PAGE gel. (FIG. 20, top left). Each fraction was flowed over a chip with prebound h7D9.v3, and the on- and off-rates were measured to reveal identical affinities (1.5 nM) for each fraction (FIG. 20, bottom left), indicating that binding of h7D9.v3 is not inhibited by glycosylation. These data were confirmed by showing that h7D9.v3 could immunoprecipitate all of the same bands as humanized anti-gD h5B6 antibody from HT1080 cells stably expressing gD-human mesothelin (the gD epitope tag of which lacks glycosylation sites), indicating that h7D9.v3 can immunoprecipitate human mesothelin regardless of glycosylation state. In contrast, humanized 22A10 preferentially immunoprecipitated the lower molecular weight (least glycosylated) species, indicating that 22A10 binding may be affected by glycosylation. (FIG. 20, right).

To assess the ability of a test antibody to bind glycosylated mesothelin compared to h7D9.v3, a FACS assay is performed in which binding of the test antibody to OVCAR3 cells is compared to binding of h7D9.v3 to OVCAR3 cells. Suitable secondary antibodies are used to detect binding of h7D9.v3 and the test antibody to OVCAR3 cells (e.g., ALEXA FLUOR® 647 anti-human antibody is used to detect binding of h7D9.v3).

I. Monoclonal Antibody 19C3 Blocks Interaction of MUC16 to Mesothelin Monoclonal antibodies were tested to determine whether they were capable of blocking binding of MUC16 to mesothelin. Binding of a purified biotinylated fragment of MUC16 (Muc16-Bt, having three mucin repeats) to mesothelin stably expressed on A431 cells (which normally do not express mesothelin) is shown in FIG. 21 ('no Ab"), left panel. Preincubation of cells with 5-fold molar ratio of 19C3, but not 7D9, inhibited the binding of MUC16-Bt to mesothelin, as detected by FACS with streptavidin-PE, as shown in FIG. 21, left panel. Conversely, binding of recombinant C-terminally his8-tagged mesothelin (purified from 293 cells) to PC3 cells stably expressing MUC16 was assessed in the absence or presence of 5-fold molar excess of the indicated anti-mesothelin antibodies (FIG. 21 right panel), which were detected by FACS with Alexa647-anti-his6 antibody. Preincubation of mesothelin with 19C3 but not 7D9 or 22A10 inhibits the binding of mesothelin to MUC16-expressing cells (FIG. 21, right panel). In fact, 7D9 and 22A10 appear to enhance binding of mesothelin to MUC16 in this assay.

J. Prevalence of Human Mesothelin in Various Cancer Types

The expression of human mesothelin in various cancers was analyzed using immunohistochemistry. Formalin-fixed paraffin embedded (FFPE) tumor microarrays (with one 1 mm core per tumor) of pancreatic ductal adenocarcinoma (FIG. 22), ovarian serous adenocarcinoma (FIG. 23) and non-small cell lung adenocarcinoma (FIG. 24) were sectioned onto microscope slides, deparaffinized and rehydrated through a diluted alcohol series. Slides were pretreated for antigen retrieval using Target Retrieval Solution (Dako, Glostrup, Denmark), quenched, blocked and stained with 10 µg/ml mouse anti-human mesothelin monoclonal antibody 19C3 for 60 minutes on a Dako autostainer. After washing, 19C3 was detected with biotinylated anti-mouse antibody, followed by ABC complex (VECTASTAIN ABC Elite Kit, Vector Laboratories, Burlingame, Calif.) and visualized using DAB (Pierce Laboratories) as a chromogen. Slides were then counterstained with Meyers Hematoxylin and dehydrated with series of alcohols and xylenes followed by coverslipping using organic mounting medium (PER-MOUNT™ PermaMount, Fisher Scientific, Pittsburgh, Pa.).

Mesothelin staining (brown) was scored by a trained pathologist according to the scheme below, taking into account the intensity (darkness of the brown staining) as well as breadth of staining. A representative example of each mesothelin score is shown in the FIGS. 22-24 for each tumor type.

0 (negative): very weak or no staining in >90% of tumor cells

1+ (mild): predominant staining pattern is weak

Figure 22:
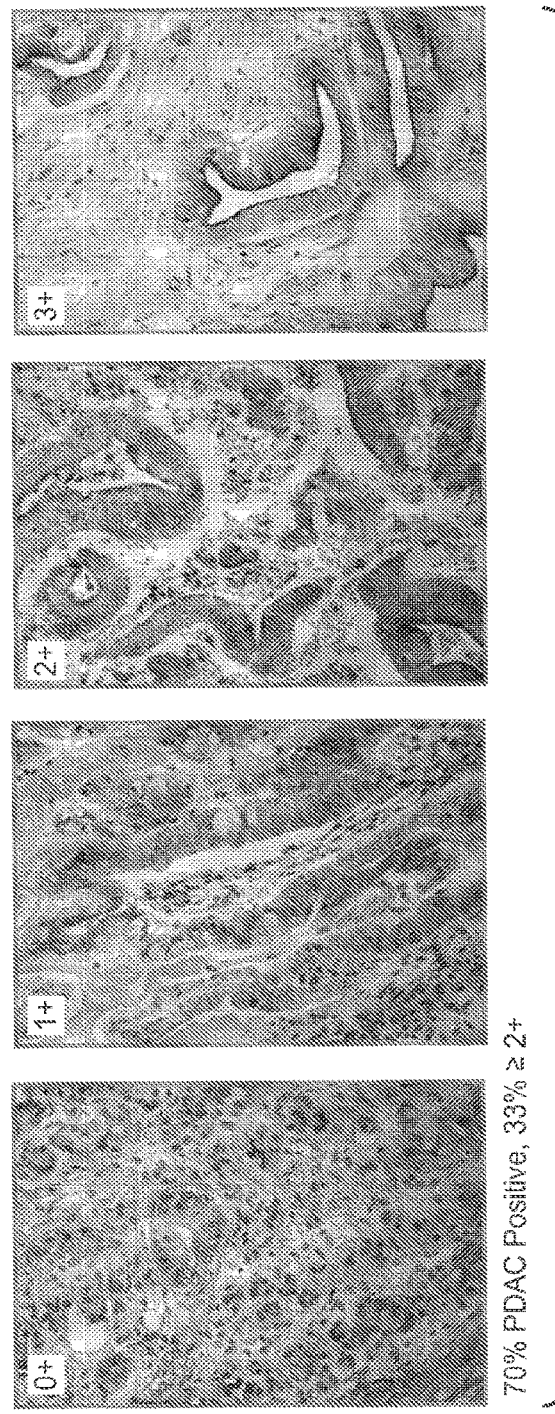
FIG. 22 shows expression of mesothelin in pancreatic ductal adenocarcinoma by immunohistochemistry (IHC), as described in Example J.
Figure 23:
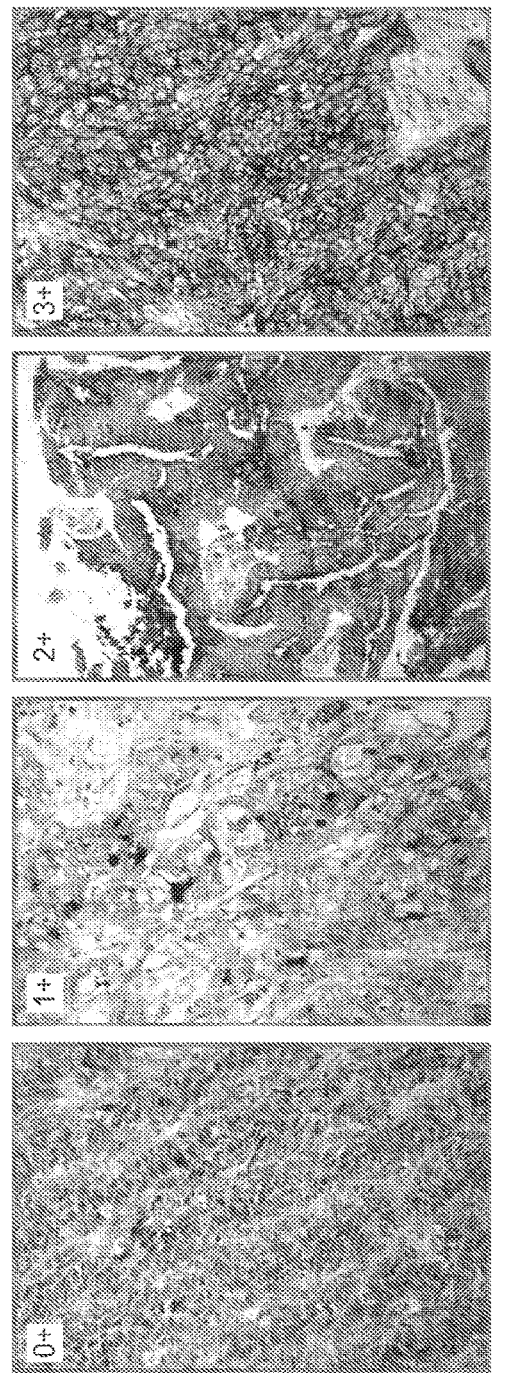
FIG. 23 shows expression of mesothelin in ovarian serous adenocarcinoma tumors by immunohistochemistry (IHC), as described in Example J.
Figure 24:
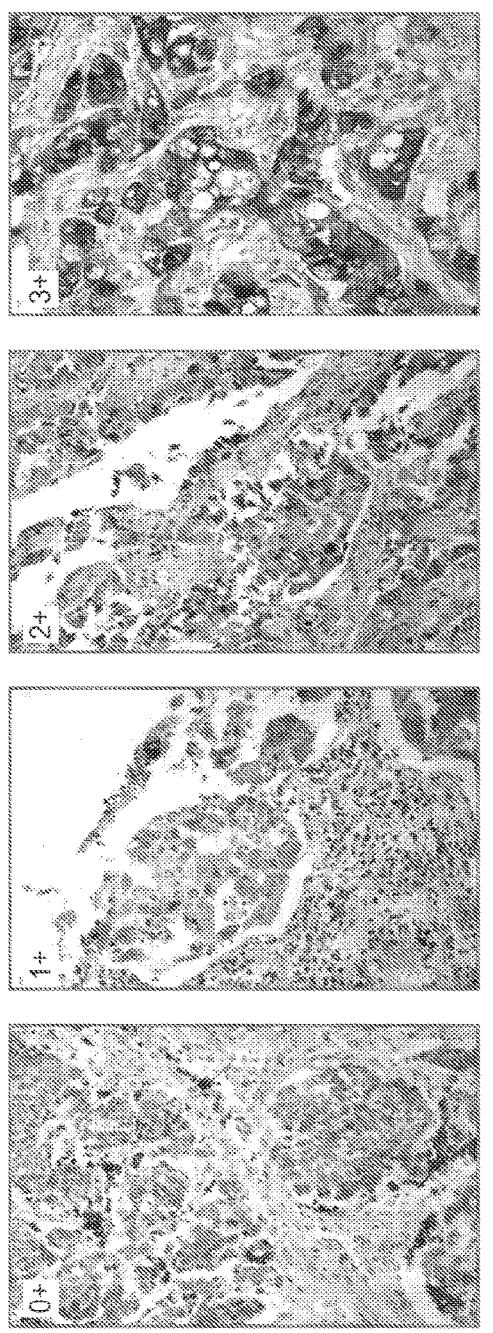
FIG. 24 shows expression of mesothelin in non-small cell lung cancer (NSCLC) adenocarcinoma by immunohistochemistry (IHC), as described in Example J.

2+ (moderate): predominant staining pattern is moderately strong in the majority (>50%) of neoplastic cells 3+ (strong): predominant staining pattern is strong in the majority (>50%) of neoplastic cells FIG. 22 shows that 70% of pancreatic ductal adenocarcinomas were mesothelin-positive, showing staining at the 1+, 2+, or 3+ levels, with 33% showing 2+ or 3+ staining. FIG. 23 shows that 98% of ovarian serous adenocarcinomas were mesothelin-positive, with 74% showing staining at the 2+ or 3+ level. Additionally, all of eight tested metastases from ovarian serous adenocarcinomas were mesothelin-positive, suggesting that primary ovarian tumors do not lose mesothelin expression following metastasis. FIG. 24 shows that 44% of non small cell lung carcinomas (NSCLC, adenocarcinoma subtype) were mesothelin-positive, with 26% showing staining at the 2+ or 3+ level. Additionally, three of eight (38%) tested matched metastases from mesothelin-positive primary NSCLC patient tumors retained mesothelin-positive staining.

Mesothelin is also expressed in mesotheliomas and in endometrial cancer, as determined by IHC using the 19C3 antibody.

Figure 25:
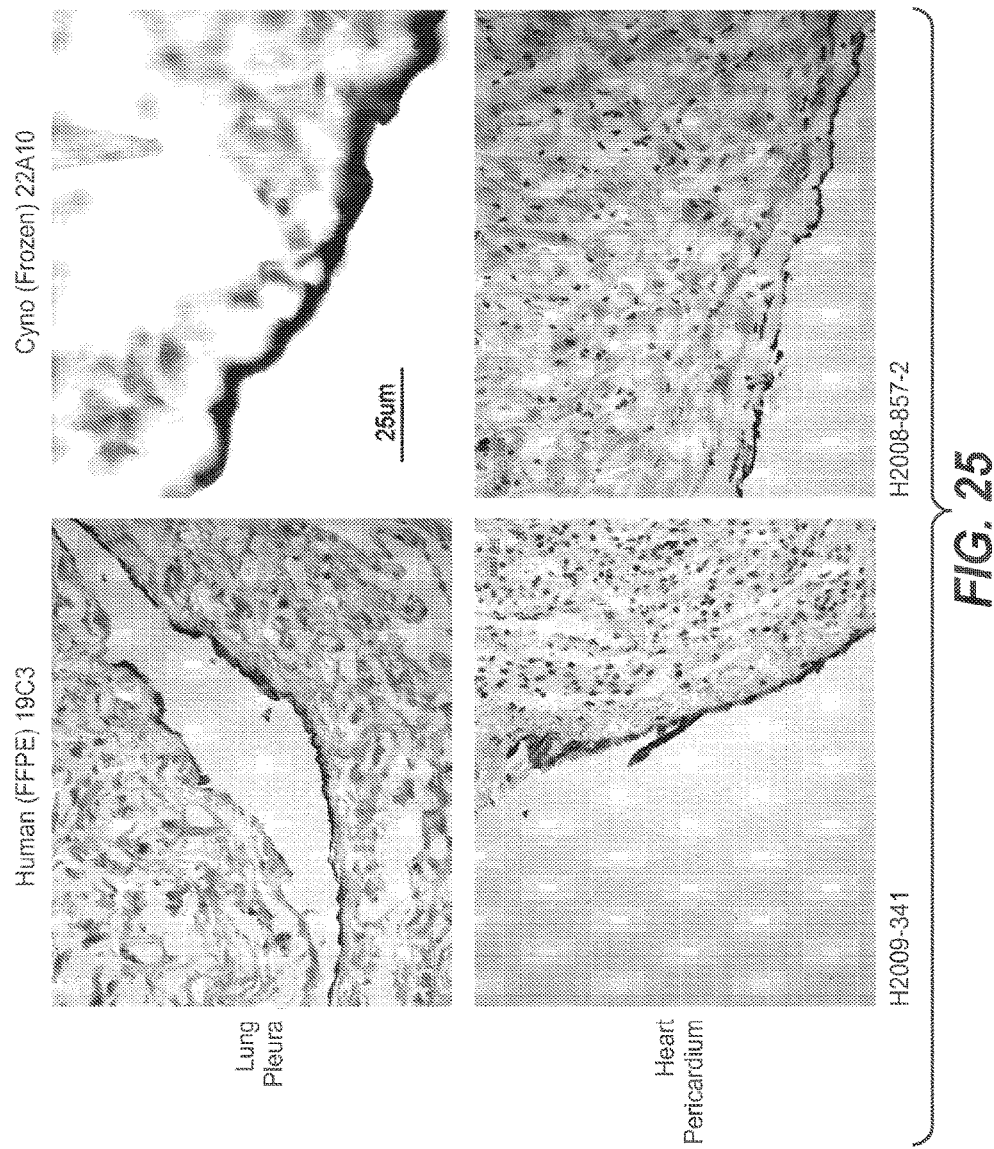
FIG. 25 shows expression of mesothelin in tissues from cynomolgus monkey (right panels) by immunohistochemistry (IHC), as described in Example J.

The expression of mesothelin in cynomolgous monkey was also examined. Lung pleural and heart pericardial mesothelia sections from human (formalin fixed paraffin embedded sections) and cynomolgus monkey (frozen sections) were sectioned and stained with 19C3 monoclonal antibody or 22A10 monoclonal antibody, respectively. Human mesothelia specifically stained with 19C3 (FIG. 25, left), and cynomolgus monkey mesothelia specifically stained with 22A10 (FIG. 25, right). These results demonstrate that 22A10 can recognize endogenous cynomolgus monkey mesothelin, which has a distribution similar to that in human.

K. Production of Anti-Mesothelin Antibody Drug Conjugates

Anti-mesothelin antibody-drug conjugates (ADCs) were produced by conjugating h7D9.v3 and h22A10.v83 to the drug-linker moiety MC-vc-PAB-MMAE, which is depicted above in Section II.D. For convenience, the drug-linker moiety MC-vc-PAB-MMAE is otherwise referred to in these Examples and in the Figures as "vcMMAE" or "VCE." (For example, h7D9.v3-MC-vc-PAB-MMAE is referred to in these Examples and in the Figures as h7D9.v3-vcMMAE or h7D9.v3-VCE.) Prior to conjugation, the antibodies were partially reduced with TCEP using standard methods in accordance with the methodology described in WO 2004/010957 A2. The partially reduced antibodies were conjugated to the drug-linker moiety using standard methods in accordance with the methodology described in Doronina et al. (2003) *Nat. Biotechnol.* 21:778-784 and US 2005/0238649 A1. Briefly, the partially reduced antibodies were combined with the drug-linker moiety to allow conjugation of the moiety to cysteine residues. The conjugation reactions were quenched, and the ADCs were purified. The drug load (average number of drug moieties per antibody) for each ADC was determined and was between 3.33 and 4.0 in all cases.

L. Efficacy of h7D9.v3-vcMMAE in In Vivo HPAC Model

Figure 26:
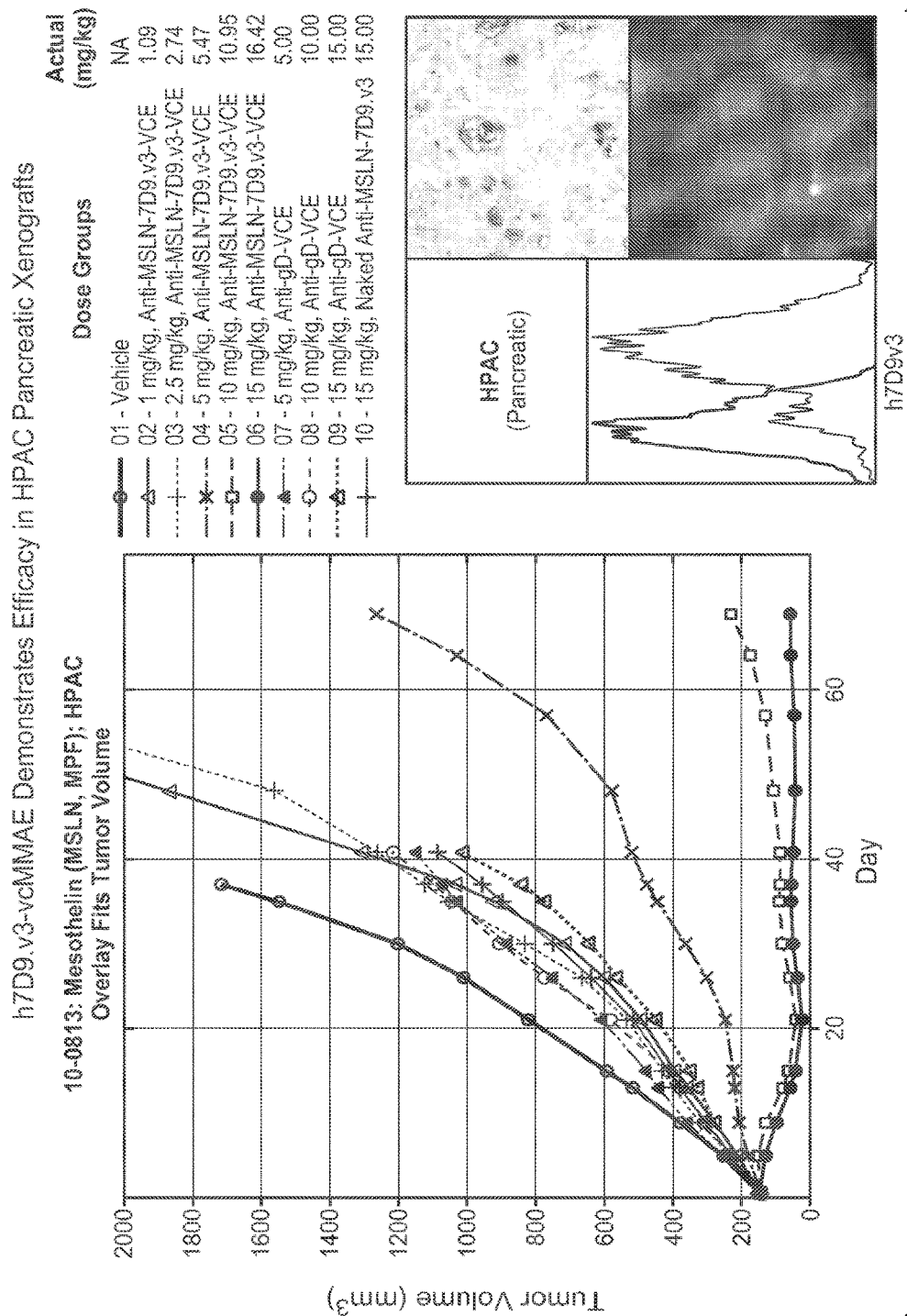
FIG. 26 shows that the immunoconjugate h7D9.v3-vcM-MAE demonstrates efficacy in HPAC pancreatic xenografts, as described in Example L.

The efficacy of h7D9.v3-vcMMAE was investigated using a pancreatic adenocarcinoma xenograft model. Five million HPAC cells (mesothelin-positive (2+) by IHC with 19C3) in HBSS were injected subcutaneously into SCID beige mice and tumors were dosed at 1.1, 2.7, 5.5, 11, and 16.4 mg/kg h7D9.v3-vcMMAE (at 3.5 MMAE/antibody), or 5, 10 and 15 mg/kg h5B6 anti-gD-vcMMAE (with 3.3 MMAE per antibody), or with 15 mg/kg naked h7D9.v3 (no MMAE). As shown in FIG. 26, substantial tumor growth inhibition was achieved at 5.5 mg/kg of h7D9.v3-vcMMAE, and regressions were achieved at 11-16 mg/kg h7D9.v3-vcMMAE, but no significant effect was observed with the naked antibody or with gD-vcMMAE control at 15 mg/kg. Modeled curve fits based on overall growth rates are shown. The lower right hand panel of FIG. 26 shows FACS analysis and internalization of h7D9.v3 in HPAC cells and IHC.

M. Efficacy of h7D9.v3-vcMMAE in Primary Pancreatic Adenocarcinoma Model

Figure 27:
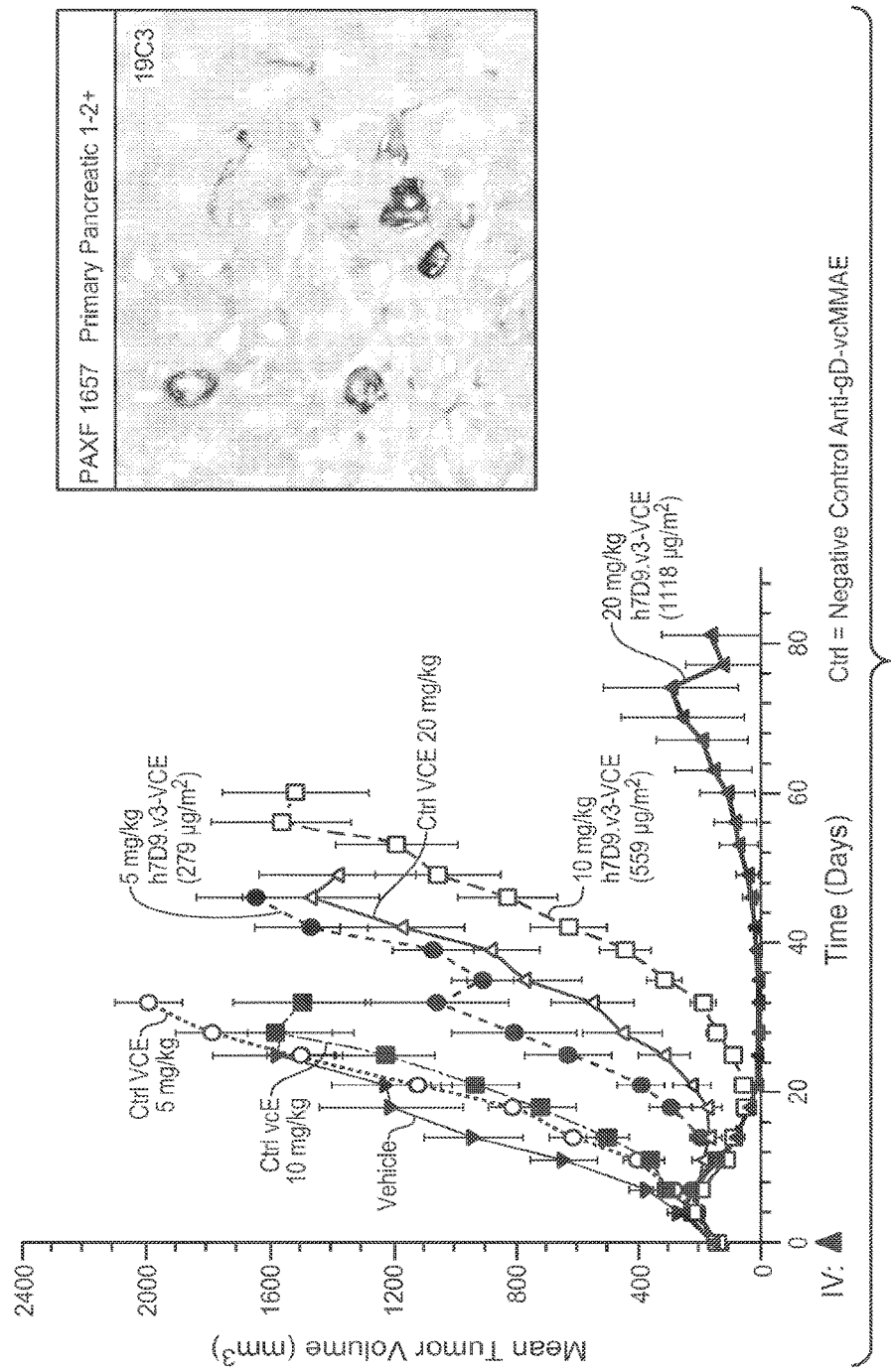
FIG. 27 shows that the immunoconjugate h7D9.v3-vcM-MAE demonstrates efficacy in a primary pancreatic xenograft, as described in Example M.

The efficacy of h7D9.v3-vcMMAE was investigated in a primary pancreatic adenocarcinoma model (Oncotest, GMBH, Germany). Chunks of primary human mesothelin-positive pancreatic tumors (expressing mesothelin at 1-2+ by IHC) were implanted subcutaneously into female NMRI nude mice, which were dosed at 5, 10 and 20 mg/kg h7D9.v3-vcMMAE (3.5 MMAE/antibody). Mean tumor volumes±standard deviations are plotted in FIG. 27. Significant tumor growth inhibition was found at all doses of h7D9.v3-vcMMAE. IHC of the primary pancreatic tumor is shown at right.

N. Efficacy of h7D9.v3-vcMMAE in Ovarian Cancer Model

Figure 28:
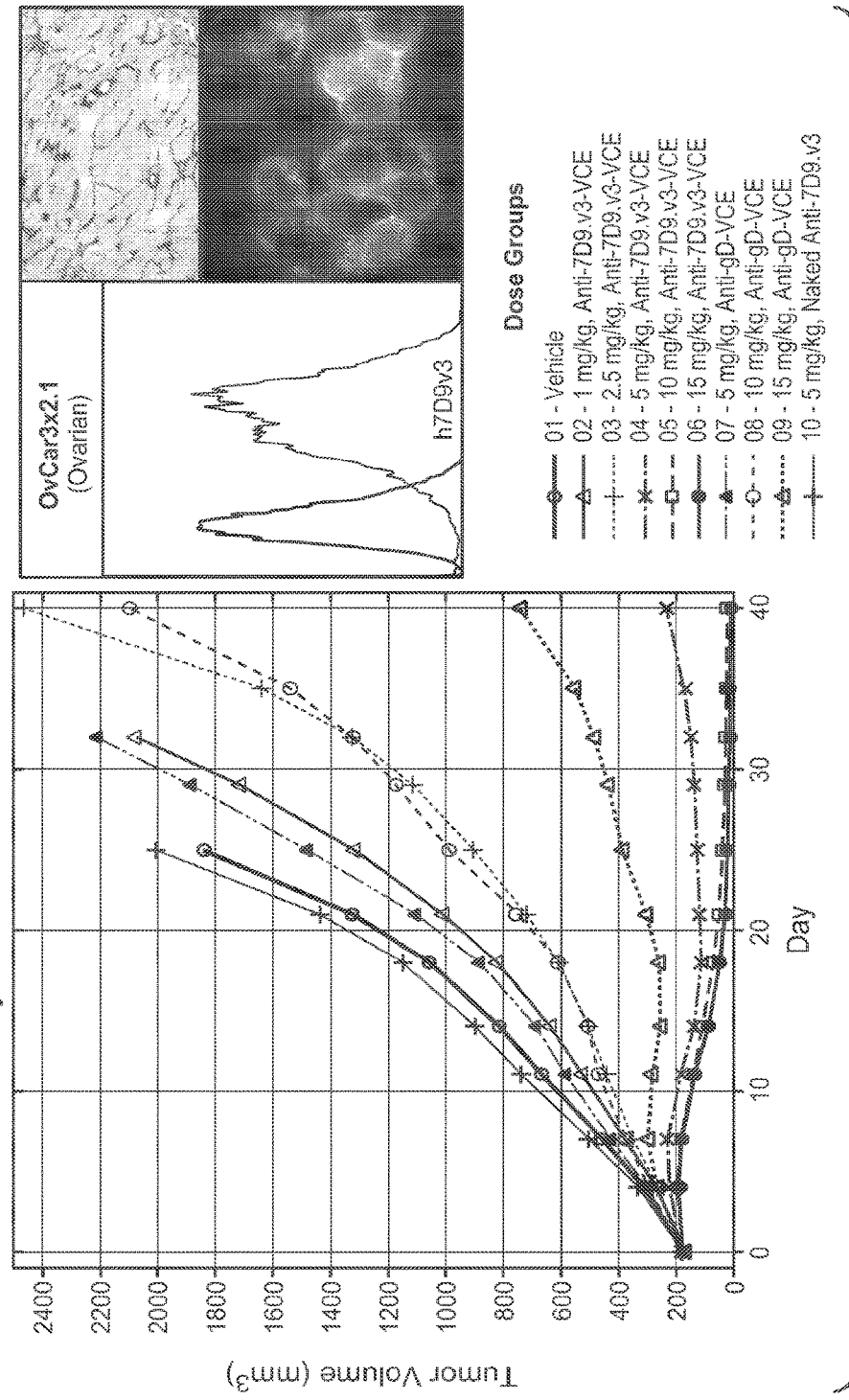
FIG. 28 shows that the immunoconjugate h7D9.v3-vcM-MAE demonstrates efficacy in an ovarian tumor xenograft model, as described in Example N.

The efficacy of h7D9.v3-vcMMAE was investigated using an ovarian cancer xenograft model. Ten million OvCar3x2.1 cells (Mesothelin-positive (2-3+) by IHC with 19C3) were injected into the mammary fat pad of CB17 SCID beige mice, which were subsequently dosed with 1, 2.5, 5, 10 and 15 mg/kg h7D9.v3-vcMMAE (3.5 MMAE/antibody) or h5B6 anti-gD-vcMMAE (3.3 MMAE/antibody). As shown in FIG. 28, modest activity was seen at 2.5 mg/kg h7D9.v3-vcMMAE and regressions at 5 mg/kg and higher, while anti-gD-vcMMAE did not exhibit activity below 5 mg/kg (only modest activity at 10 mg/kg and tumor stasis at 15 mg/kg). Modeled curve fits based on overall growth rates are shown. The right hand panel of FIG. 28 shows FACS analysis and internalization of h7D9.v3 in OvCar3x2.1 cells and IHC.

O. Efficacy of h7D9.v30-vcMMAE in a Lung Cancer Model

The efficacy of h7D9.v3-vcMMAE was investigated using a lung cancer (squamous cell carcinoma) xenograft model. Five million H226x2 cells (mesothelin-positive (3+) by IHC) were injected in a 50:50 mix of Matrigel:HBSS into the flank of CB17 SCID mice. Mean tumor volumes±standard deviations are plotted in FIG. 29. h7D9v3-vcMMAE (3.5 MMAE/antibody) showed modest activity at 5 mg/kg and tumor stasis at 10 mg/kg, while there was no significant activity with the control anti-gD-vcMMAE conjugate (3.97 MMAE/antibody) at either dose. The right hand panel of FIG. 29 shows FACS analysis and internalization of h7D9.v3 in H226x2 cells and IHC.

P. h7D9.v3-vcMMAE and h22A10.v83-vcMMAE have Similar Efficacy

Figure 30:
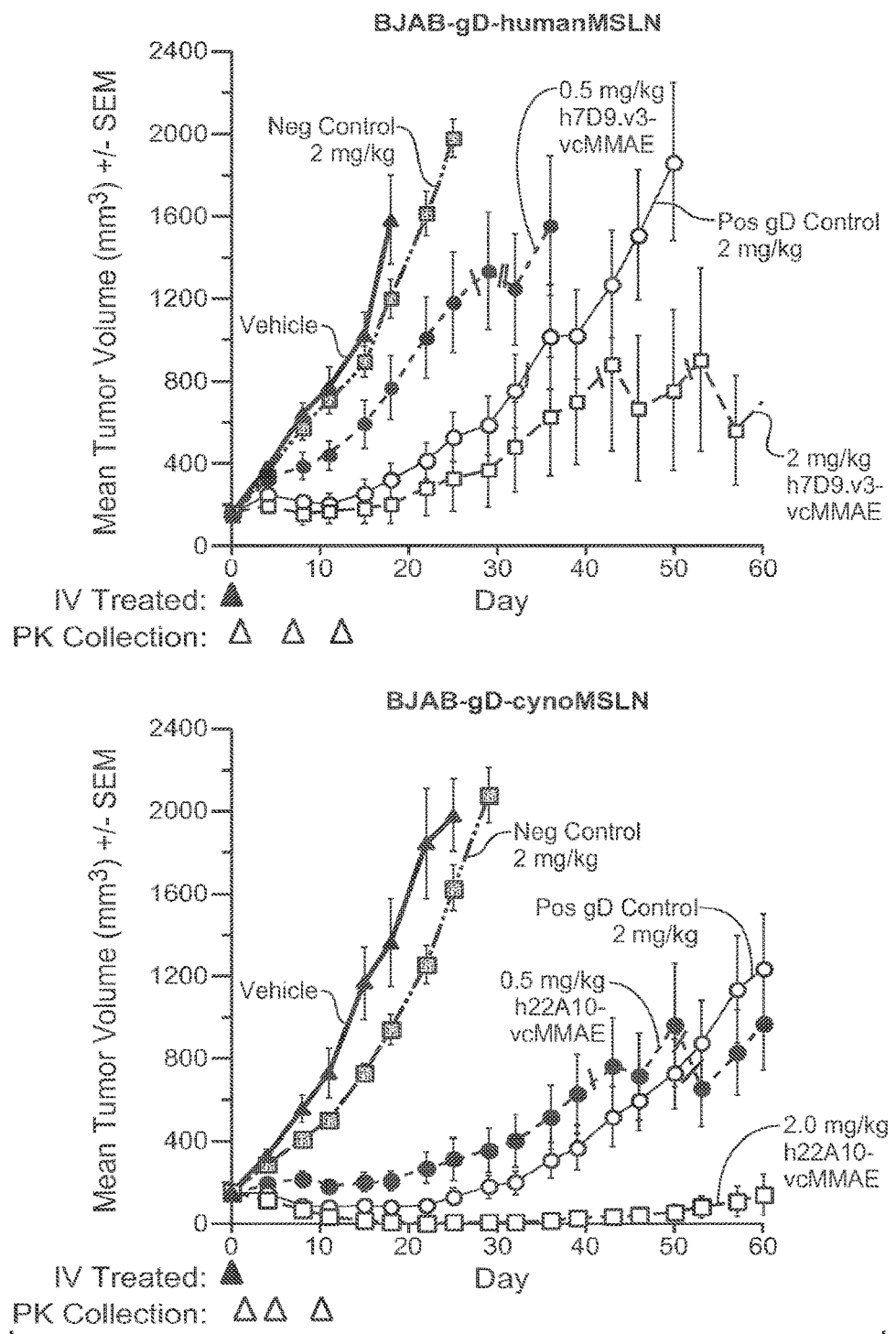
FIG. 30 shows that the efficacy of the immunoconjugate h7D9.v3-vcMMAE against human mesothelin is similar to that of the immunoconjugate h22A10.v83-vcMMAE against cynomolgus monkey mesothelin in transfected BJAB xenograft tumor models, as described in Example P.

The efficacy of h7D9.v3-vcMMAE compared to h22A10.v83-vcMMAE was investigated. Twenty million BJAB cells stably expressing either gD-human mesothelin (left) or gD-cynomolgus monkey mesothelin (right) were inoculated subcutaneously into CB17 SCID mice in HBSS buffer. Mice were dosed with 0.5 or 2 mg/kg h7D9.v3-vcMMAE (in mice inoculated with BJAB-gD-human mesothelin) or h22A10.v83-vcMMAE (in mice inoculated with BJAB-gD-cynomolgous monkey mesothelin), or with anti-gD-vcMMAE at 2 mg/kg used as a positive control and as a normalizer for any differences in expression between the two species of cell line. Mean tumor volumes±standard deviations are plotted in FIG. 30. Both h7D9.v3-vcMMAE and h22A10.v83-vcMMAE exhibited better activity at 2 mg/kg than the gD-vcMMAE control against BJAB-gD-human mesothelin and BJAB-gD-cynomolgous monkey mesothelin tumors, respectively. The negative control in this experiment was an irrelevant antibody conjugated to vcMMAE, which displayed no significant activity.

Figure 29:
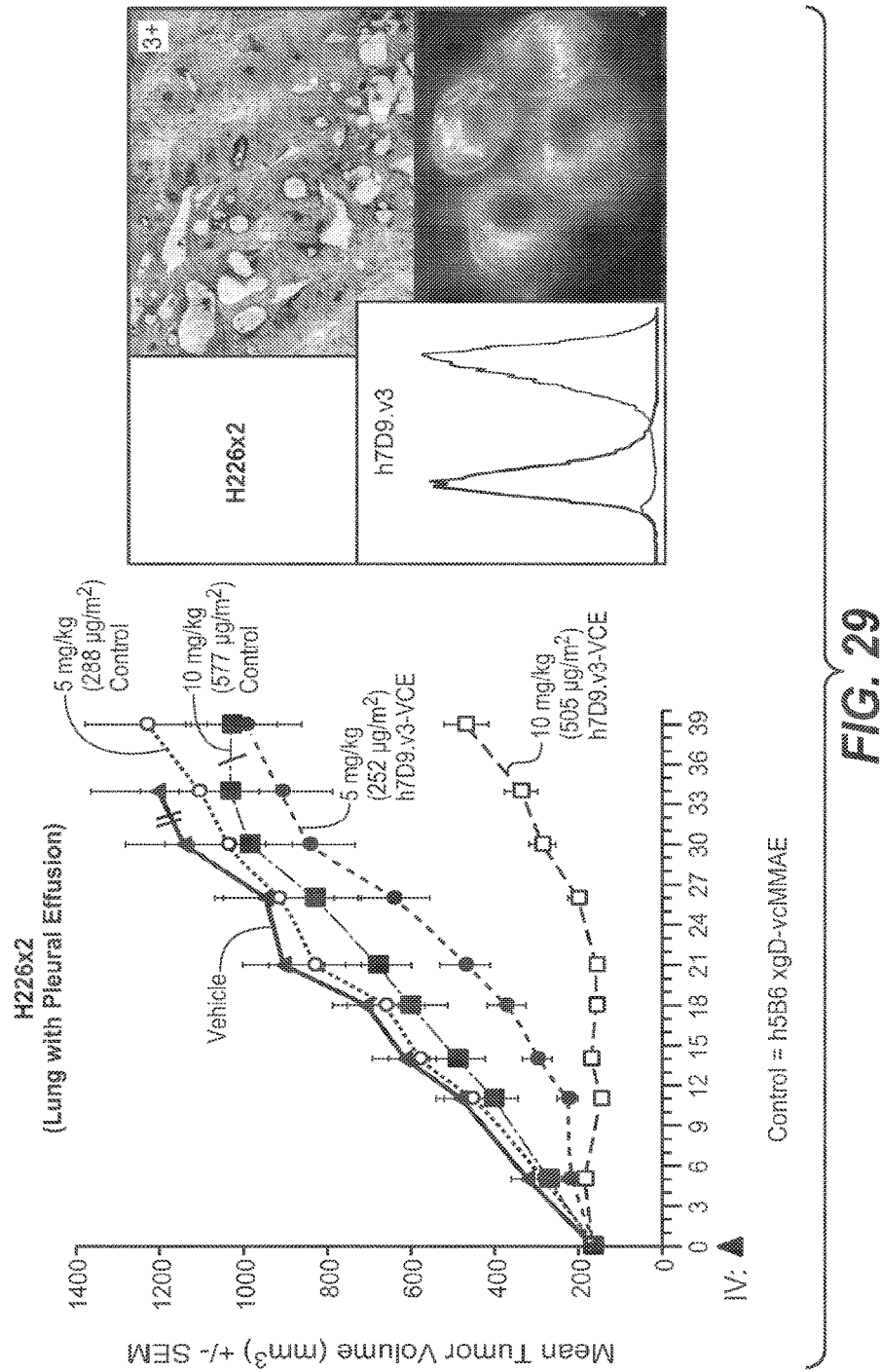
FIG. 29 shows that the immunoconjugate h7D9.v3-vcM-MAE demonstrates efficacy in a lung squamous cell carcinoma xenograft model, as described in Example O.

To further assess the activity of h22A10.v83-vcMMAE, the H226x2 tumors of FIG. 29 and OvCar3x2.1 tumors grown as described in FIG. 28 were dosed with the indicated concentrations of h7D9.v3-vcMMAE and h22A10.v83-vcMMAE (3.53 MMAE/antibody), or anti-gD-vcMMAE as a negative control. Mean tumor volumes±standard deviations are plotted in FIG. 31. Despite significantly weaker binding of naked h22A10.v83 compared to h7D9.v3 to both of these cell lines by FACS, h22A10.v83-vcMMAE was similarly effective as h7D9.v3-vcMMAE in the H226x2 model (upper left panel), and only slightly less active in the OvCar3x2.1 model (upper right panel), as indicated by the faster regression of the tumors after the 6 mg/kg dose.

Q. MUC16 and Mesothelin Form a Complex on "Dual-Positive" Cell Lines

Figure 32:
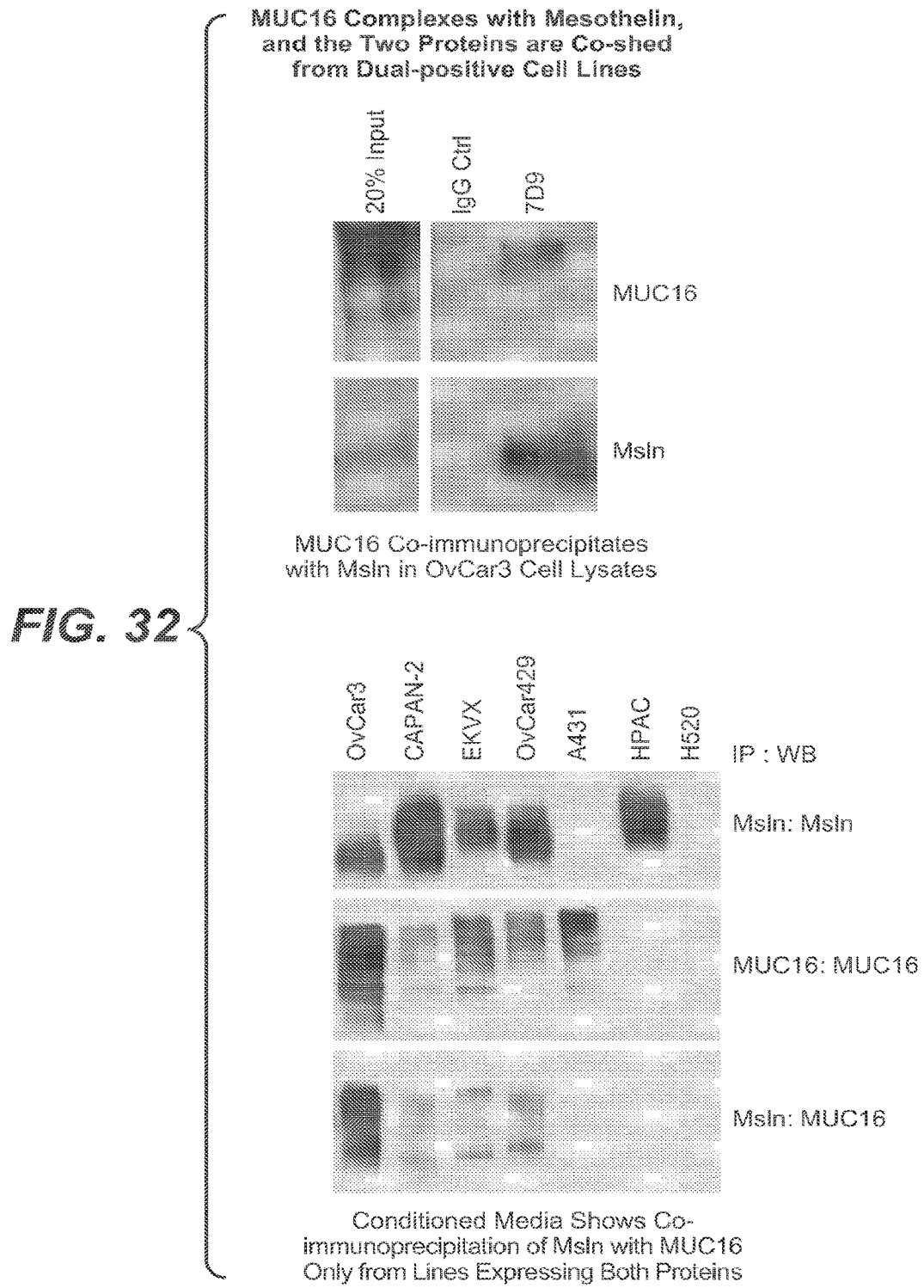
FIG. 32 shows that MUC16 forms a complex with mesothelin, and the two proteins are co-shed from dual-positive cell lines, as described in Example Q.

The interaction of MUC16 and mesothelin on cell lines was investigated. OvCar3 cells, which express both mesothelin and MUC16, were lysed in 1% NP40 buffer. As shown in FIG. 32, left panel, lysates were immunoprecipitated with m7D9 or isotype control IgG and western blotted with an anti-MUC16 antibody (upper blot) or h7D9 (lower blot) to detect mesothelin:MUC16 complexes or total mesothelin, respectively. (20% non-immunoprecipitated input is shown in the left lane.) m7D9 was able to co-immunoprecipitate MUC16 with mesothelin from OvCar3 cell lysates. That result demonstrates that MUC16 forms a complex with mesothelin in cell lines that express both mesothelin and MUC16 (i.e., "dual-positive" cell lines).

As shown in FIG. 32, right panel, antibodies to either mesothelin or MUC16 were used to immunoprecipitate (IP) those proteins from conditioned media in which the indicated cell lines were grown. The cell lines express mesothelin only (HPAC), MUC16 only (A431), neither (H520), or both (OvCar3, CAPAN-2, EKVX and OvCar429 cells). Either anti-mesothelin chimeric antibody ch7D9 (top and bottom panels) or an anti-MUC16 antibody (middle panel) was used for immunoprecipitations. The washed immunoprecipitates were Western blotted (WB) with murine anti-mesothelin antibody 2E5 (top) or murine anti-MUC16 B-domain (M11-like) antibody 1.B.823 (US Biological, Swampscott, Mass.; middle and bottom panels). Accordingly, the upper panel shows immunoprecipitated mesothelin from cell lines that express mesothelin, the middle panel shows immunoprecipitated MUC16 from cell lines that express MUC16, and the bottom panel shows co-immunoprecipitated mesothelin:MUC16 complexes, which are specific to cell lines expressing both proteins (dual-positive cell lines). These results indicate that mesothelin can be shed into the media while bound to MUC16. Accordingly, antibodies and immunoconjugates of the invention are useful for treating mesothelin-positive cancer, including dual-positive cancers.

R. 19C3, but not 7D9, Displaces Pre-Bound MUC16 from Mesothelin

Figure 33:
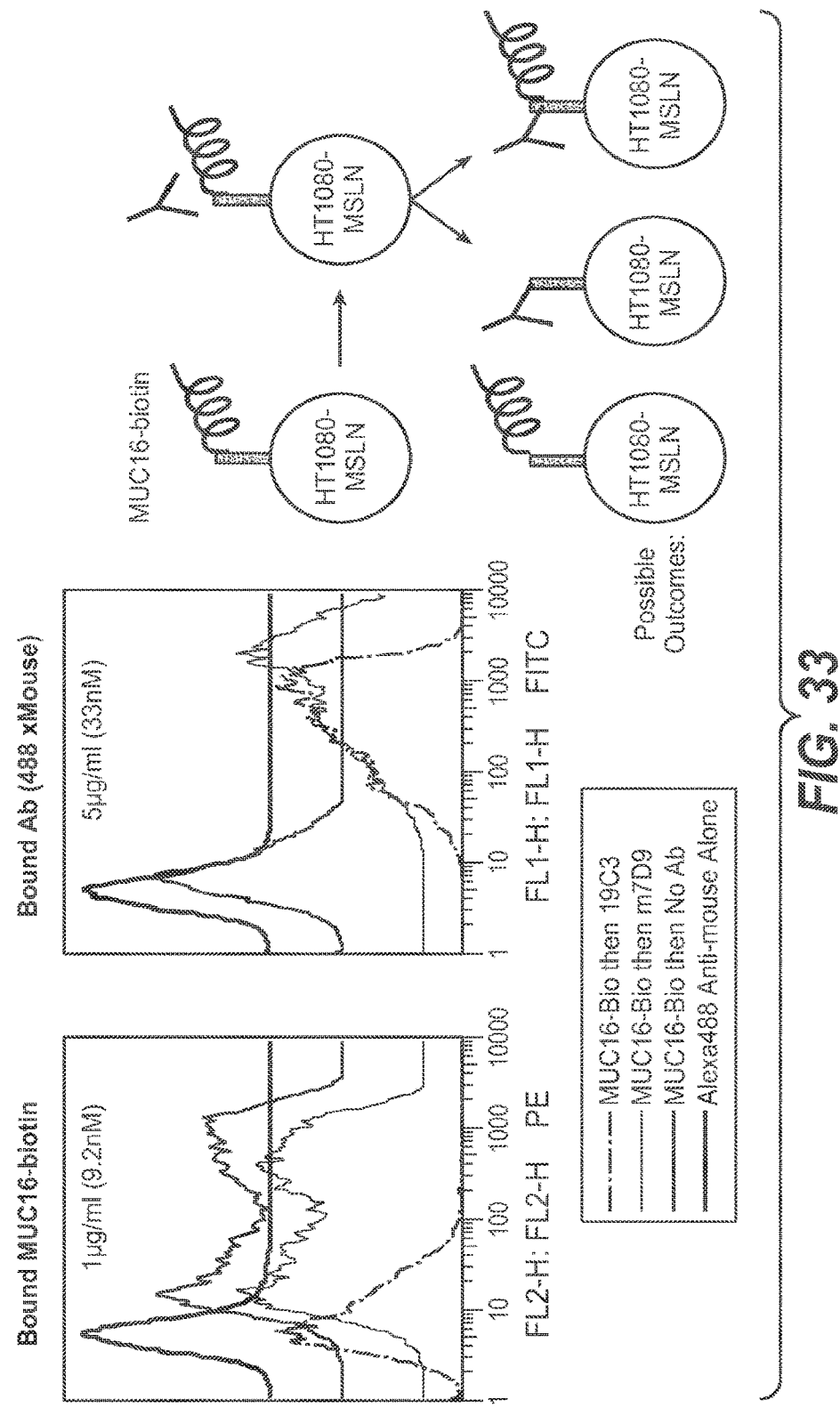
FIG. 33 shows that 19C3, but not 7D9, displaces prebound MUC16 from mesothelin.

The binding of 19C3 to mesothelin in the presence of MUC16 was investigated. MUC16-biotin (1 ug/ml, or 9.2 nM) was pre-bound to HT1080 cells expressing mesothelin. 19C3 (5 ug/ml) was added to determine if it could displace the pre-bound MUC16. MUC16-biotin was detected with SAPE detection reagent, and bound antibody was detected with Alexa488 anti-mouse antibody. FIG. 33 shows that 19C3 was indeed able to displace MUC16 and bind to mesothelin. Antibody 7D9 (33 nM), which binds to a region of mesothelin outside the MUC16 binding site, was used as a negative control and as expected was not able to displace the pre-bound MUC16. Additional experiments demonstrated that 19C3 also displaces MUC16 at 0.1 ug/ml, whereas antibody 2E5 can displace MUC16 only at ≥5 ug/ml (data not shown).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to mesothelin, wherein the antibody comprises (i) HVR-H1 comprising the amino acid sequence of SEQ ID NO:36, (ii) HVR-H2 comprising the amino acid sequence of SEQ ID NO:37, (iii) HVR-H3 comprising the amino acid sequence of SEQ ID NO:39, (iv) HVR-L1 comprising the amino acid sequence of SEQ ID NO:33, (v) HVR-L2 comprising the amino acid sequence of SEQ ID NO:34, and (vi) HVR-L3 comprising the amino acid sequence of SEQ ID NO:35.

2. The antibody of claim 1, which is a monoclonal antibody.

3. The antibody of claim 1, which is a human, humanized, or chimeric antibody.

4. The antibody of claim 1, which is an antibody fragment that binds mesothelin.

5. The antibody of claim 1, wherein mesothelin is human mesothelin of SEQ ID NO:43.

6. The antibody of claim 1, wherein the antibody binds an epitope of SEQ ID NO:43, wherein the epitope comprises E211 according to the numbering of SEQ ID NO:43, and that optionally has one or more of the following characteristics:

(a) does not block binding of mesothelin to Mucin 16 (MUC16); and/or
(b) binds mesothelin with an affinity of less than or equal to 5 nM.

7. The antibody of claim 6, wherein the antibody does not block binding of mesothelin to MUC16.

8. The antibody of claim 1, wherein the antibody comprises
(a) a VH sequence having at least 95% sequence identity to the amino acid sequence of SEQ ID NO:16;
(b) a VL sequence having at least 95% sequence identity to the amino acid sequence of SEQ ID NO:12; or
(c) a VH sequence as in (a) and a VL sequence as in (b).

9. The antibody of claim 1, comprising a VH sequence of SEQ ID NO:16.

10. The antibody of claim 1, comprising a VL sequence of SEQ ID NO:12.

11. The antibody of claim 1, which is an IgG1, IgG2a or IgG2b antibody.

12. The antibody of claim 1 conjugated to a label.

13. The antibody of claim 12, wherein the label is a positron emitter.

14. The antibody of claim 13, wherein the positron emitter is $^{89}$Zr.

15. An antibody comprising a VH sequence of SEQ ID NO:16 and a VL sequence of SEQ ID NO:12.

16. An immunoconjugate having the formula Ab-(L-D)p, wherein:
(a) Ab is the antibody of claim 1;
(b) L is a linker;
(c) D is a drug of formula $D_E$

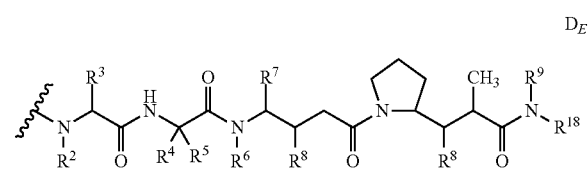

and wherein $R^2$ and $R^6$ are each methyl, $R^3$ and $R^4$ are each isopropyl, $R^5$ is H, $R^7$ is sec-butyl, each $R^8$ is independently selected from $CH_3$, O—$CH_3$, OH, and H; $R^9$ is H; and $R^{18}$ is $C(R^8)_2$—$C(R^8)_2$-aryl; and
(d) p ranges from 1-8.

17. The immunoconjugate of claim 16, wherein the drug is an auristatin.

18. The immunoconjugate of claim 17, wherein the drug is monomethyl auristatin E (MMAE).

19. The immunoconjugate of claim 16, wherein the linker is cleavable by a protease.

20. The immunoconjugate of claim 19, wherein the linker comprises a val-cit dipeptide.

21. The immunoconjugate of claim 16 having the formula:

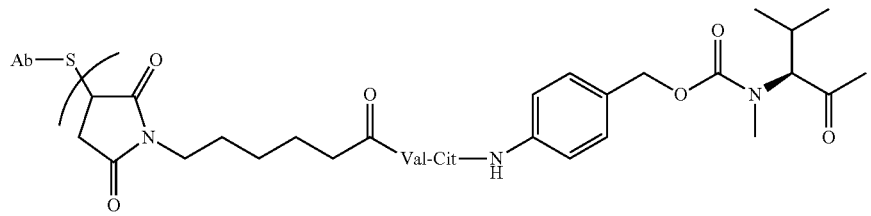

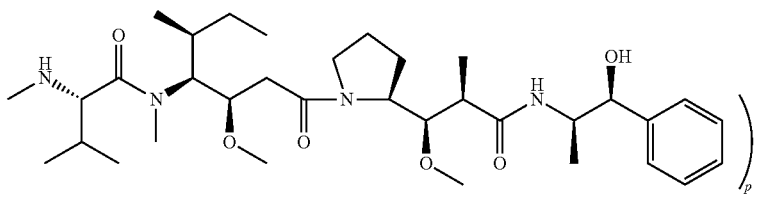

wherein S is a sulfur atom.

22. The immunoconjugate of claim 21, wherein p ranges from 2-5.

23. A pharmaceutical formulation comprising the immunoconjugate of claim 16 and a pharmaceutically acceptable carrier.

24. The pharmaceutical formulation of claim 23, further comprising an additional therapeutic agent.

25. The pharmaceutical formulation of claim 24, wherein the additional therapeutic agent is gemcitabine.

26. The pharmaceutical formulation of claim 24, wherein the additional therapeutic agent is an anti-MUC16 antibody conjugated to a cytotoxic agent.

* * * * *

SEQUENCE LISTING

<160> NUMBER OF SEQ ID NOS: 74

<210> SEQ ID NO 1
<211> LENGTH: 108
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys Arg
            100                 105

<210> SEQ ID NO 2
<211> LENGTH: 113
<212> TYPE: PRT
<213> ORGANISM: Mus sp.

<400> SEQUENCE: 2

Asp Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Phe Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys His Gln
                85                  90                  95

Tyr Leu Ser Ser Tyr Thr Phe Gly Gly Gly Thr Lys Val Glu Ile Lys
            100                 105                 110

Arg

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Val Leu Tyr Ser
            20                  25                  30

-continued

Ser Asn Gln Lys Asn Tyr Leu Ala Trp Tyr Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys His Gln
                85                  90                  95

Tyr Leu Ser Ser Tyr Thr Phe Gly Gln Gly Thr Lys Val Glu Ile Lys
                100                 105                 110

Arg

<210> SEQ ID NO 4
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
 1               5                  10                  15

Asp Arg Val Thr Ile Thr Cys Lys Ser Ser Gln Ser Val Leu Tyr Ser
                20                  25                  30

Ser Asn Gln Lys Asn Tyr Leu Ala Trp Phe Gln Gln Lys Pro Gly Lys
            35                  40                  45

Ala Pro Lys Leu Leu Ile Tyr Trp Ala Ser Thr Arg Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Phe Cys His Gln
                85                  90                  95

Tyr Leu Ser Ser Tyr Thr Phe Gly Gln Gly Thr Lys Val Glu Ile Lys
                100                 105                 110

Arg

<210> SEQ ID NO 5
<211> LENGTH: 112
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Val Ile Ser Gly Asp Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
                100                 105                 110

```
<210> SEQ ID NO 6
<211> LENGTH: 115
<212> TYPE: PRT
<213> ORGANISM: Mus sp.

<400> SEQUENCE: 6

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Thr Tyr
            20                  25                  30

Trp Met His Trp Val Lys Gln Arg Pro Gly Gln Gly Leu Glu Trp Ile
        35                  40                  45

Gly Tyr Ile Arg Pro Ser Thr Gly Tyr Thr Glu Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Thr Val Tyr Tyr Cys
                85                  90                  95

Ala Arg Ser Arg Trp Leu Leu Asp Tyr Trp Gly Gln Gly Thr Ser Leu
            100                 105                 110

Thr Val Ser
        115

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Thr Tyr
            20                  25                  30

Trp Met His Trp Val Arg Gln Ala Pro Gly Lys Gly Leu Glu Trp Val
        35                  40                  45

Gly Tyr Ile Arg Pro Ser Thr Gly Tyr Thr Glu Tyr Asn Gln Lys Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Arg Trp Leu Leu Asp Tyr Trp Gly Gln Gly Thr Leu Val
            100                 105                 110

Thr Val Ser
        115

<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Thr Tyr
            20                  25                  30

Trp Met His Trp Val Arg Gln Ala Pro Gly Lys Gly Leu Glu Trp Val
        35                  40                  45

Gly Tyr Ile Arg Pro Ser Thr Gly Tyr Thr Glu Tyr Asn Gln Lys Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Ser Arg Trp Leu Leu Asp Tyr Trp Gly Gln Gly Thr Leu Val
        100                 105                 110

Thr Val Ser
        115

<210> SEQ ID NO 9
<211> LENGTH: 108
<212> TYPE: PRT
<213> ORGANISM: Homo sapiens

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
            85                  90                  95

Thr Phe Gly Gln Gly Thr Lys Val Glu Ile Lys Arg
        100                 105

<210> SEQ ID NO 10
<211> LENGTH: 97
<212> TYPE: PRT
<213> ORGANISM: Mus sp.

<400> SEQUENCE: 10

Gly Ala Ser Leu Gly Asp Arg Val Thr Ile Ser Cys Arg Ala Ser Gln
1               5                   10                  15

Asp Ile Ser Asn Tyr Leu Asn Trp Tyr Gln Gln Lys Pro Asp Gly Thr
            20                  25                  30

Val Lys Leu Leu Ile Tyr Tyr Thr Ser Arg Leu His Ser Gly Val Pro
        35                  40                  45

Ser Arg Phe Ser Ala Ser Gly Ser Gly Thr Asp Tyr Ser Leu Thr Ile
    50                  55                  60

Ser Asn Leu Glu Gln Glu Asp Ile Ala Thr Tyr Phe Cys Gln Gln Gly
65                  70                  75                  80

Asn Thr Leu Pro Tyr Thr Phe Gly Gly Gly Thr Lys Leu Glu Ile Lys
            85                  90                  95

Arg

<210> SEQ ID NO 11
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Arg
            100                 105

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Arg
            100                 105

<210> SEQ ID NO 13
<211> LENGTH: 113
<212> TYPE: PRT
<213> ORGANISM: Homo sapiens

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Asp Tyr Trp Gly Gln Gly Thr Leu Val Thr Val Ser
            100                 105                 110

Ser

<210> SEQ ID NO 14
<211> LENGTH: 117
<212> TYPE: PRT
<213> ORGANISM: Mus sp.

<400> SEQUENCE: 14

Glu Leu Leu Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Phe Met Ser Trp Val Arg Gln Thr Pro Glu Lys Arg Leu Glu Trp Val
            35                  40                  45

Ala Thr Ile Ser Asn Gly Gly Thr Tyr Thr Tyr Tyr Pro Asp Ser Val
    50                  55                  60

Lys Gly Arg Phe Thr Ile Ser Lys Asp Asn Ala Lys Asn Asn Leu Tyr
65                  70                  75                  80

Leu Gln Met Ser Ser Leu Lys Ser Glu Asp Thr Ala Met Tyr Tyr Cys
                85                  90                  95

Ala Arg Phe Asp Gly Tyr Tyr Phe Asp Tyr Trp Gly Gln Gly Thr Thr
            100                 105                 110

Leu Thr Val Ser Ser
        115

<210> SEQ ID NO 15
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Val Arg Gln Ala Pro Gly Lys Gly Leu Glu Trp Val
            35                  40                  45

Ala Thr Ile Ser Asn Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Gly Tyr Tyr Phe Asp Tyr Trp Gly Gln Gly Thr Leu
            100                 105                 110

Val Thr Val Ser Ser
        115

<210> SEQ ID NO 16
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Phe Met Ser Trp Val Arg Gln Ala Pro Gly Lys Gly Leu Glu Trp Val
        35                  40                  45

Ala Thr Ile Ser Asn Gly Gly Thr Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Phe Asp Gly Tyr Ile Phe Asp Tyr Trp Gly Gln Gly Thr Leu
            100                 105                 110

Val Thr Val Ser Ser
        115

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ser Ser Gln Ser Val Leu Tyr Ser Ser Asn Gln Lys Asn Tyr Leu
1               5                   10                  15

Ala

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Ala Ser Thr Arg Glu Ser
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

His Gln Tyr Leu Ser Ser Tyr Thr
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Tyr Thr Phe Thr Thr Tyr Trp Met His
1               5                   10

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Ile Arg Pro Ser Thr Gly Tyr Thr Glu Tyr Asn Gln Lys Phe
1               5                   10                  15

Lys Asp

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Arg Ser Arg Trp Leu Leu Asp Tyr
1               5

<210> SEQ ID NO 23
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Trp Tyr Gln Gln Lys Pro Gly Lys Ala Pro Lys Leu Leu Ile Tyr

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Phe Gln Gln Lys Pro Gly Lys Ala Pro Lys Leu Leu Ile Tyr
1               5                   10                  15

<210> SEQ ID NO 26
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 27
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Gly Gln Gly Thr Lys Val Glu Ile Lys Arg
1               5                   10

<210> SEQ ID NO 29
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser

```
            20                  25
```

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

```
Trp Val Arg Gln Ala Pro Gly Lys Gly Leu Glu Trp Val
1               5                   10
```

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Trp Gly Gln Gly Thr Leu Val Thr Val Ser
1               5                   10
```

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

```
Arg Ala Ser Gln Asp Ile Ser Asn Tyr Leu Asn
1               5                   10
```

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

```
Tyr Thr Ser Arg Leu His Ser
1               5
```

<210> SEQ ID NO 35
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 35

Gln Gln Gly Asn Thr Leu Pro Tyr Thr
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Ser Asp Tyr Phe Met Ser
1               5                   10

<210> SEQ ID NO 37
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Thr Ile Ser Asn Gly Gly Thr Tyr Thr Tyr Tyr Pro Asp Ser Val
1               5                   10                  15

Lys Gly

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Arg Phe Asp Gly Tyr Tyr Phe Asp Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Arg Phe Asp Gly Tyr Ile Phe Asp Tyr
1               5                   10

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Gly Gln Gly Thr Leu Val Thr Val Ser Ser
1               5                   10

<210> SEQ ID NO 42
<211> LENGTH: 622
<212> TYPE: PRT
<213> ORGANISM: Homo sapiens

<400> SEQUENCE: 42

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270
```

```
Gln Arg Ser Ser Arg Asp Pro Ser Trp Arg Gln Pro Glu Arg Thr Ile
        275                 280                 285

Leu Arg Pro Arg Phe Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Ala Ser Thr Leu Ala
610                 615                 620

<210> SEQ ID NO 43
<211> LENGTH: 285
<212> TYPE: PRT
<213> ORGANISM: Homo sapiens

<400> SEQUENCE: 43

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30
```

```
Asp Ala Ala Leu Leu Ala Thr Gln Met Asp Arg Val Asn Ala Ile Pro
            35                  40                  45

Phe Thr Tyr Glu Gln Leu Asp Val Leu Lys His Lys Leu Asp Glu Leu
 50                  55                  60

Tyr Pro Gln Gly Tyr Pro Glu Ser Val Ile Gln His Leu Gly Tyr Leu
 65                  70                  75                  80

Phe Leu Lys Met Ser Pro Glu Asp Ile Arg Lys Trp Asn Val Thr Ser
                 85                  90                  95

Leu Glu Thr Leu Lys Ala Leu Leu Glu Val Asn Lys Gly His Glu Met
                100                 105                 110

Ser Pro Gln Val Ala Thr Leu Ile Asp Arg Phe Val Lys Gly Arg Gly
            115                 120                 125

Gln Leu Asp Lys Asp Thr Leu Asp Thr Leu Thr Ala Phe Tyr Pro Gly
130                 135                 140

Tyr Leu Cys Ser Leu Ser Pro Glu Glu Leu Ser Ser Val Pro Pro Ser
145                 150                 155                 160

Ser Ile Trp Ala Val Arg Pro Gln Asp Leu Asp Thr Cys Asp Pro Arg
                165                 170                 175

Gln Leu Asp Val Leu Tyr Pro Lys Ala Arg Leu Ala Phe Gln Asn Met
            180                 185                 190

Asn Gly Ser Glu Tyr Phe Val Lys Ile Gln Ser Phe Leu Gly Gly Ala
            195                 200                 205

Pro Thr Glu Asp Leu Lys Ala Leu Ser Gln Gln Asn Val Ser Met Asp
210                 215                 220

Leu Ala Thr Phe Met Lys Leu Arg Thr Asp Ala Val Leu Pro Leu Thr
225                 230                 235                 240

Val Ala Glu Val Gln Lys Leu Leu Gly Pro His Val Glu Gly Leu Lys
                245                 250                 255

Ala Glu Glu Arg His Arg Pro Val Arg Asp Trp Ile Leu Arg Gln Arg
            260                 265                 270

Gln Asp Asp Leu Asp Thr Leu Gly Leu Gly Leu Gln Gly
            275                 280                 285

<210> SEQ ID NO 44
<211> LENGTH: 630
<212> TYPE: PRT
<213> ORGANISM: Homo sapiens

<400> SEQUENCE: 44

Met Ala Leu Pro Thr Ala Arg Pro Leu Leu Gly Ser Cys Gly Thr Pro
 1               5                  10                  15

Ala Leu Gly Ser Leu Leu Phe Leu Leu Phe Ser Leu Gly Trp Val Gln
                20                  25                  30

Pro Ser Arg Thr Leu Ala Gly Glu Thr Gly Gln Glu Ala Ala Pro Leu
            35                  40                  45

Asp Gly Val Leu Ala Asn Pro Pro Asn Ile Ser Ser Leu Ser Pro Arg
 50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Leu Phe Leu Asn Pro
```

```
            115                 120                 125
Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                    165                 170                 175

Leu Ser Glu Ala Asp Val Arg Ala Leu Gly Gly Leu Ala Cys Asp Leu
                180                 185                 190

Pro Gly Arg Phe Val Ala Glu Ser Ala Glu Val Leu Leu Pro Arg Leu
            195                 200                 205

Val Ser Cys Pro Gly Pro Leu Asp Gln Asp Gln Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
                260                 265                 270

Gln Arg Ser Ser Arg Asp Pro Ser Trp Arg Gln Pro Glu Arg Thr Ile
            275                 280                 285

Leu Arg Pro Arg Phe Arg Arg Glu Val Glu Lys Thr Ala Cys Pro Ser
290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
                340                 345                 350

Lys His Lys Leu Asp Glu Leu Tyr Pro Gln Gly Tyr Pro Glu Ser Val
            355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
                420                 425                 430

Leu Asp Lys Asp Thr Leu Asp Thr Leu Thr Ala Phe Tyr Pro Gly Tyr
            435                 440                 445

Leu Cys Ser Leu Ser Pro Glu Leu Ser Ser Pro Pro Ser Ser
            450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
                500                 505                 510

Thr Glu Asp Leu Lys Ala Leu Ser Gln Gln Asn Val Ser Met Asp Leu
            515                 520                 525

Ala Thr Phe Met Lys Leu Arg Thr Asp Ala Val Leu Pro Leu Thr Val
            530                 535                 540
```

Ala Glu Val Gln Lys Leu Leu Gly Pro His Val Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630

<210> SEQ ID NO 45
<211> LENGTH: 293
<212> TYPE: PRT
<213> ORGANISM: Homo sapiens

<400> SEQUENCE: 45

Glu Val Glu Lys Thr Ala Cys Pro Ser Gly Lys Lys Ala Arg Glu Ile
1               5                   10                  15

Asp Glu Ser Leu Ile Phe Tyr Lys Lys Trp Glu Leu Glu Ala Cys Val
            20                  25                  30

Asp Ala Ala Leu Leu Ala Thr Gln Met Asp Arg Val Asn Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Gln His Leu Gly Tyr Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Glu Val Asn Lys Gly His Glu Met
            100                 105                 110

Ser Pro Gln Ala Pro Arg Arg Pro Leu Pro Gln Val Ala Thr Leu Ile
        115                 120                 125

Asp Arg Phe Val Lys Gly Arg Gly Gln Leu Asp Lys Asp Thr Leu Asp
    130                 135                 140

Thr Leu Thr Ala Phe Tyr Pro Gly Tyr Leu Cys Ser Leu Ser Pro Glu
145                 150                 155                 160

Glu Leu Ser Ser Val Pro Pro Ser Ser Ile Trp Ala Val Arg Pro Gln
                165                 170                 175

Asp Leu Asp Thr Cys Asp Pro Arg Gln Leu Asp Val Leu Tyr Pro Lys
            180                 185                 190

Ala Arg Leu Ala Phe Gln Asn Met Asn Gly Ser Glu Tyr Phe Val Lys
        195                 200                 205

Ile Gln Ser Phe Leu Gly Gly Ala Pro Thr Glu Asp Leu Lys Ala Leu
    210                 215                 220

Ser Gln Gln Asn Val Ser Met Asp Leu Ala Thr Phe Met Lys Leu Arg
225                 230                 235                 240

Thr Asp Ala Val Leu Pro Leu Thr Val Ala Glu Val Gln Lys Leu Leu
                245                 250                 255

Gly Pro His Val Glu Gly Leu Lys Ala Glu Glu Arg His Arg Pro Val
            260                 265                 270

Arg Asp Trp Ile Leu Arg Gln Arg Gln Asp Asp Leu Asp Thr Leu Gly

```
                275                 280                 285

Leu Gly Leu Gln Gly
        290

<210> SEQ ID NO 46
<211> LENGTH: 285
<212> TYPE: PRT
<213> ORGANISM: Macaca fascicularis

<400> SEQUENCE: 46

Asp Val Glu Arg Thr Thr Cys Pro Pro Glu Lys Glu Val His Glu Ile
1               5                   10                  15

Asp Glu Asn Leu Ile Phe Tyr Lys Lys Arg Glu Leu Glu Ala Cys Val
            20                  25                  30

Asp Ala Ala Leu Leu Ala Ala Gln Met Asp Arg Val Asp Ala Ile Pro
        35                  40                  45

Phe Thr Tyr Glu Gln Leu Asp Val Leu Lys His Lys Leu Asp Glu Leu
    50                  55                  60

Tyr Pro Gln Gly Tyr Pro Glu Ser Val Ile Arg His Leu Gly His Leu
65                  70                  75                  80

Phe Leu Lys Met Ser Pro Glu Asp Ile Arg Lys Trp Asn Val Thr Ser
                85                  90                  95

Leu Glu Thr Leu Lys Ala Leu Leu Lys Val Ser Lys Gly His Glu Met
            100                 105                 110

Ser Ala Gln Val Ala Thr Leu Ile Asp Arg Val Val Gly Arg Gly
        115                 120                 125

Gln Leu Asp Lys Asp Thr Val Asp Thr Leu Thr Ala Phe Cys Pro Gly
    130                 135                 140

Cys Leu Cys Ser Leu Ser Pro Glu Arg Leu Ser Ser Val Pro Pro Ser
145                 150                 155                 160

Val Ile Gly Ala Val Arg Pro Gln Asp Leu Asp Thr Cys Gly Pro Arg
                165                 170                 175

Gln Leu Asp Val Leu Tyr Pro Lys Ala Arg Leu Ala Phe Gln Asn Met
            180                 185                 190

Ser Gly Ser Glu Tyr Phe Val Lys Ile Arg Pro Phe Leu Gly Gly Ala
        195                 200                 205

Pro Thr Glu Asp Leu Lys Ala Leu Ser Gln Gln Asn Val Ser Met Asp
    210                 215                 220

Leu Ala Thr Phe Met Lys Leu Arg Arg Glu Ala Val Leu Pro Leu Thr
225                 230                 235                 240

Val Ala Glu Val Gln Lys Leu Leu Gly Pro His Val Glu Gly Leu Lys
                245                 250                 255

Val Glu Glu Gln His Ser Pro Val Arg Asp Trp Ile Leu Lys Gln Arg
            260                 265                 270

Gln Asp Asp Leu Asp Thr Leu Gly Leu Gly Leu Gln Gly
        275                 280                 285

<210> SEQ ID NO 47
<211> LENGTH: 285
<212> TYPE: PRT
<213> ORGANISM: Rattus sp.

<400> SEQUENCE: 47

Asp Thr Glu Gln Lys Ala Cys Pro Pro Gly Lys Glu Pro Asn Val Val
1               5                   10                  15

Asp Glu Asn Leu Ile Phe Tyr Gln Asn Trp Glu Leu Glu Ala Cys Val
```

```
                    20                  25                  30
Asp Gly Thr Leu Leu Ala Gly Gln Met Asp Leu Val Asn Glu Ile Pro
                35                  40                  45
Phe Thr Tyr Glu Gln Leu Ser Ile Phe Lys His Lys Leu Asp Lys Thr
 50                  55                  60
Tyr Pro Gln Gly Tyr Pro Glu Ser Leu Ile Lys Gln Leu Gly His Phe
 65                  70                  75                  80
Phe Arg Tyr Val Ser Pro Glu Asp Ile Arg Gln Trp Asn Val Thr Ser
                85                  90                  95
Pro Asp Thr Val Asn Thr Leu Leu Lys Val Ser Lys Gly Gln Lys Met
                100                 105                 110
Asp Ala Gln Val Ile Ala Leu Val Ala Cys Tyr Leu Arg Gly Gly Gly
            115                 120                 125
Lys Leu Asp Glu Asp Ile Val Lys Ala Leu Asp Asn Ile Pro Leu Ser
        130                 135                 140
Tyr Leu Cys Asp Phe Ser Pro Gln Asp Leu His Ala Ile Pro Ser Ser
145                 150                 155                 160
Val Met Trp Leu Val Gly Leu His Asp Leu Asp Lys Cys Ser Gln Arg
                165                 170                 175
His Leu Gly Ile Leu Tyr Gln Lys Ala Cys Ser Ala Phe Gln Asn Val
            180                 185                 190
Ser Gly Leu Glu Tyr Phe Glu Lys Ile Arg Thr Phe Leu Gly Gly Ala
        195                 200                 205
Ser Arg Glu Asp Leu Arg Ala Leu Ser Gln His Asn Val Ser Met Asp
    210                 215                 220
Ile Ala Thr Phe Lys Lys Leu Gln Val Asp Ala Leu Val Gly Leu Ser
225                 230                 235                 240
Val Ala Glu Val Gln Lys Leu Leu Gly Pro His Ile Gly Asp Leu Lys
                245                 250                 255
Thr Glu Glu Asp Lys Ser Pro Val Arg Asp Trp Leu Phe Arg Gln Gln
            260                 265                 270
Gln Lys Asp Leu Asp Ser Leu Gly Leu Gly Leu Gln Gly
        275                 280                 285

<210> SEQ ID NO 48
<211> LENGTH: 285
<212> TYPE: PRT
<213> ORGANISM: Mus sp.

<400> SEQUENCE: 48

Asp Ala Glu Gln Lys Ala Cys Pro Pro Gly Lys Glu Pro Tyr Lys Val
 1               5                  10                  15
Asp Glu Asp Leu Ile Phe Tyr Gln Asn Trp Glu Leu Glu Ala Cys Val
                20                  25                  30
Asp Gly Thr Met Leu Ala Arg Gln Met Asp Leu Val Asn Glu Ile Pro
                35                  40                  45
Phe Thr Tyr Glu Gln Leu Ser Ile Phe Lys His Lys Leu Asp Lys Thr
 50                  55                  60
Tyr Pro Gln Gly Tyr Pro Glu Ser Leu Ile Gln Gln Leu Gly His Phe
 65                  70                  75                  80
Phe Arg Tyr Val Ser Pro Glu Asp Ile His Gln Trp Asn Val Thr Ser
                85                  90                  95
Pro Asp Thr Val Lys Thr Leu Leu Lys Val Ser Lys Gly Gln Lys Met
                100                 105                 110
```

Asn Ala Gln Ala Ile Ala Leu Val Ala Cys Tyr Leu Arg Gly Gly
            115                 120                 125

Gln Leu Asp Glu Asp Met Val Lys Ala Leu Gly Asp Ile Pro Leu Ser
        130                 135                 140

Tyr Leu Cys Asp Phe Ser Pro Gln Asp Leu His Ser Val Pro Ser Ser
145                 150                 155                 160

Val Met Trp Leu Val Gly Pro Gln Asp Leu Asp Lys Cys Ser Gln Arg
                165                 170                 175

His Leu Gly Leu Leu Tyr Gln Lys Ala Cys Ser Ala Phe Gln Asn Val
            180                 185                 190

Ser Gly Leu Glu Tyr Phe Glu Lys Ile Lys Thr Phe Leu Gly Gly Ala
        195                 200                 205

Ser Val Lys Asp Leu Arg Ala Leu Ser Gln His Asn Val Ser Met Asp
    210                 215                 220

Ile Ala Thr Phe Lys Arg Leu Gln Val Asp Ser Leu Val Gly Leu Ser
225                 230                 235                 240

Val Ala Glu Val Gln Lys Leu Leu Gly Pro Asn Ile Val Asp Leu Lys
                245                 250                 255

Thr Glu Glu Asp Lys Ser Pro Val Arg Asp Trp Leu Phe Arg Gln His
            260                 265                 270

Gln Lys Asp Leu Asp Arg Leu Gly Leu Gly Leu Gln Gly
        275                 280                 285

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 49

His His His His His His His His
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 50

His His His His His His
1               5

<210> SEQ ID NO 51
<211> LENGTH: 4
<212> TYPE: PRT
<213> ORGANISM: Homo sapiens

<400> SEQUENCE: 51

Glu Val Glu Lys
1

<210> SEQ ID NO 52
<211> LENGTH: 4
<212> TYPE: PRT
<213> ORGANISM: Mus sp.

<400> SEQUENCE: 52

```
Asp Ala Glu Gln
1

<210> SEQ ID NO 53
<211> LENGTH: 4
<212> TYPE: PRT
<213> ORGANISM: Macaca fascicularis

<400> SEQUENCE: 53

Asp Val Glu Arg
1

<210> SEQ ID NO 54
<211> LENGTH: 81
<212> TYPE: PRT
<213> ORGANISM: Homo sapiens

<400> SEQUENCE: 54

Lys Asp Thr Leu Asp Thr Leu Thr Ala Phe Tyr Pro Gly Tyr Leu Cys
1               5                   10                  15

Ser Leu Ser Pro Glu Glu Leu Ser Ser Val Pro Pro Ser Ser Ile Trp
            20                  25                  30

Ala Val Arg Pro Gln Asp Leu Asp Thr Cys Asp Pro Arg Gln Leu Asp
        35                  40                  45

Val Leu Tyr Pro Lys Ala Arg Leu Ala Phe Gln Asn Met Asn Gly Ser
    50                  55                  60

Glu Tyr Phe Val Lys Ile Gln Ser Phe Leu Gly Gly Ala Pro Thr Glu
65                  70                  75                  80

Asp

<210> SEQ ID NO 55
<211> LENGTH: 81
<212> TYPE: PRT
<213> ORGANISM: Macaca fascicularis

<400> SEQUENCE: 55

Lys Asp Thr Val Asp Thr Leu Thr Ala Phe Cys Pro Gly Cys Leu Cys
1               5                   10                  15

Ser Leu Ser Pro Glu Arg Leu Ser Ser Val Pro Pro Ser Val Ile Gly
            20                  25                  30

Ala Val Arg Pro Gln Asp Leu Asp Thr Cys Gly Pro Arg Gln Leu Asp
        35                  40                  45

Val Leu Tyr Pro Lys Ala Arg Leu Ala Phe Gln Asn Met Ser Gly Ser
    50                  55                  60

Glu Tyr Phe Val Lys Ile Arg Pro Phe Leu Gly Gly Ala Pro Thr Glu
65                  70                  75                  80

Asp

<210> SEQ ID NO 56
<211> LENGTH: 81
<212> TYPE: PRT
<213> ORGANISM: Rattus sp.

<400> SEQUENCE: 56

Glu Asp Ile Val Lys Ala Leu Asp Asn Ile Pro Leu Ser Tyr Leu Cys
1               5                   10                  15

Asp Phe Ser Pro Gln Asp Leu His Ala Ile Pro Ser Ser Val Met Trp
            20                  25                  30
```

Leu Val Gly Leu His Asp Leu Asp Lys Cys Ser Gln Arg His Leu Gly
            35                  40                  45

Ile Leu Tyr Gln Lys Ala Cys Ser Ala Phe Gln Asn Val Ser Gly Leu
    50                  55                  60

Glu Tyr Phe Glu Lys Ile Arg Thr Phe Leu Gly Gly Ala Ser Arg Glu
65                  70                  75                  80

Asp

<210> SEQ ID NO 57
<211> LENGTH: 81
<212> TYPE: PRT
<213> ORGANISM: Mus sp.

<400> SEQUENCE: 57

Glu Asp Met Val Lys Ala Leu Gly Asp Ile Pro Leu Ser Tyr Leu Cys
1               5                   10                  15

Asp Phe Ser Pro Gln Asp Leu His Ser Val Pro Ser Ser Val Met Trp
            20                  25                  30

Leu Val Gly Pro Gln Asp Leu Asp Lys Cys Ser Gln Arg His Leu Gly
            35                  40                  45

Leu Leu Tyr Gln Lys Ala Cys Ser Ala Phe Gln Asn Val Ser Gly Leu
    50                  55                  60

Glu Tyr Phe Glu Lys Ile Lys Thr Phe Leu Gly Gly Ala Ser Val Lys
65                  70                  75                  80

Asp

<210> SEQ ID NO 58
<211> LENGTH: 4
<212> TYPE: PRT
<213> ORGANISM: Homo sapiens

<400> SEQUENCE: 58

Lys Asp Thr Leu
1

<210> SEQ ID NO 59
<211> LENGTH: 4
<212> TYPE: PRT
<213> ORGANISM: Mus sp.

<400> SEQUENCE: 59

Glu Asp Met Val
1

<210> SEQ ID NO 60
<211> LENGTH: 4
<212> TYPE: PRT
<213> ORGANISM: Homo sapiens

<400> SEQUENCE: 60

Thr Ala Phe Tyr
1

<210> SEQ ID NO 61
<211> LENGTH: 4
<212> TYPE: PRT
<213> ORGANISM: Mus sp.

<400> SEQUENCE: 61

Gly Asp Ile Pro
1

```
<210> SEQ ID NO 62
<211> LENGTH: 4
<212> TYPE: PRT
<213> ORGANISM: Homo sapiens

<400> SEQUENCE: 62

Glu Glu Leu Ser
1

<210> SEQ ID NO 63
<211> LENGTH: 4
<212> TYPE: PRT
<213> ORGANISM: Mus sp.

<400> SEQUENCE: 63

Gln Asp Leu His
1

<210> SEQ ID NO 64
<211> LENGTH: 4
<212> TYPE: PRT
<213> ORGANISM: Homo sapiens

<400> SEQUENCE: 64

Pro Ser Ser Ile
1

<210> SEQ ID NO 65
<211> LENGTH: 4
<212> TYPE: PRT
<213> ORGANISM: Mus sp.

<400> SEQUENCE: 65

Ser Ser Val Met
1

<210> SEQ ID NO 66
<211> LENGTH: 4
<212> TYPE: PRT
<213> ORGANISM: Homo sapiens

<400> SEQUENCE: 66

Thr Cys Asp Pro
1

<210> SEQ ID NO 67
<211> LENGTH: 4
<212> TYPE: PRT
<213> ORGANISM: Mus sp.

<400> SEQUENCE: 67

Lys Cys Ser Gln
1

<210> SEQ ID NO 68
<211> LENGTH: 5
<212> TYPE: PRT
<213> ORGANISM: Homo sapiens

<400> SEQUENCE: 68

Gln Leu Asp Val Leu
1               5
```

```
<210> SEQ ID NO 69
<211> LENGTH: 5
<212> TYPE: PRT
<213> ORGANISM: Mus sp.

<400> SEQUENCE: 69

His Leu Gly Leu Leu
1               5

<210> SEQ ID NO 70
<211> LENGTH: 4
<212> TYPE: PRT
<213> ORGANISM: Homo sapiens

<400> SEQUENCE: 70

Met Asn Gly Ser
1

<210> SEQ ID NO 71
<211> LENGTH: 4
<212> TYPE: PRT
<213> ORGANISM: Mus sp.

<400> SEQUENCE: 71

Val Ser Gly Leu
1

<210> SEQ ID NO 72
<211> LENGTH: 4
<212> TYPE: PRT
<213> ORGANISM: Homo sapiens

<400> SEQUENCE: 72

Pro Thr Glu Asp
1

<210> SEQ ID NO 73
<211> LENGTH: 4
<212> TYPE: PRT
<213> ORGANISM: Mus sp.

<400> SEQUENCE: 73

Ser Thr Lys Asp
1

<210> SEQ ID NO 74
<211> LENGTH: 4
<212> TYPE: PRT
<213> ORGANISM: Mus sp.

<400> SEQUENCE: 74

Ser Val Lys Asp
1
```